(12) United States Patent
Cheruvallath et al.

(10) Patent No.: US 9,475,816 B2
(45) Date of Patent: Oct. 25, 2016

(54) SUBSTITUTED-1,4-DIHYDROPYRAZOLO[4,3-B]INDOLES

(71) Applicant: TAKEDA PHARMACEUTICAL COMPANY LIMITED, Chuo-ku, Osaka-shi, Osaka (JP)

(72) Inventors: Zacharia Cheruvallath, San Diego, CA (US); Mallareddy Komandla, San Diego, CA (US); John David Lawson, San Diego, CA (US); Christopher McBride, San Diego, CA (US); Mingnam Tang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 30 days.

(21) Appl. No.: 14/426,369

(22) PCT Filed: Sep. 6, 2013

(86) PCT No.: PCT/US2013/058527
§ 371 (c)(1),
(2) Date: Mar. 5, 2015

(87) PCT Pub. No.: WO2014/039831
PCT Pub. Date: Mar. 13, 2014

(65) Prior Publication Data
US 2015/0225405 A1    Aug. 13, 2015

Related U.S. Application Data

(60) Provisional application No. 61/698,369, filed on Sep. 7, 2012.

(51) Int. Cl.
| C07D 487/04 | (2006.01) |
| C07D 519/00 | (2006.01) |
| A61K 31/4439 | (2006.01) |
| A61K 31/4985 | (2006.01) |
| A61K 31/437 | (2006.01) |
| A61K 31/496 | (2006.01) |
| C07D 487/14 | (2006.01) |
| A61K 31/4162 | (2006.01) |
| A61K 31/506 | (2006.01) |

(52) U.S. Cl.
CPC ......... *C07D 487/04* (2013.01); *A61K 31/4162* (2013.01); *A61K 31/437* (2013.01); *A61K 31/4439* (2013.01); *A61K 31/496* (2013.01); *A61K 31/4985* (2013.01); *A61K 31/506* (2013.01); *C07D 487/14* (2013.01); *C07D 519/00* (2013.01)

(58) Field of Classification Search
None
See application file for complete search history.

(56) References Cited

U.S. PATENT DOCUMENTS

| 5,612,356 A | 3/1997 | Asada et al. |
| 6,297,238 B1 | 10/2001 | Arnold et al. |
| 6,462,036 B1 | 10/2002 | Arnold et al. |
| 6,849,644 B2 | 2/2005 | Bromidge et al. |
| 7,816,536 B2 | 10/2010 | Davies et al. |
| 2012/0004162 A1 | 1/2012 | Vath et al. |

FOREIGN PATENT DOCUMENTS

| WO | WO 00/07996 A2 | 2/2000 |
| WO | WO 00/27822 A2 | 5/2000 |
| WO | WO 02/089811 A1 | 11/2002 |
| WO | WO 03/097609 A1 | 11/2003 |
| WO | WO 2004/080973 A1 | 9/2004 |
| WO | WO 2005/095387 A1 | 10/2005 |
| WO | WO 2008/008650 A1 | 1/2008 |
| WO | WO 2008/092352 A1 | 8/2008 |
| WO | WO 2010/065883 A2 | 6/2010 |

OTHER PUBLICATIONS

Hou et al, Org. Biomol. Chem., 2013, 11, 3288-3296.*
A.P. Kudelka et al, N. Engl. J. Med. 338:991-92 (1998).
A.P. Kudelka et al., Clin. Cancer Res. 3:1501-05 (1997).
Arfin et al., Proc. Natl. Acad. Sci. USA 92:7714-18 (1995).
C.J. Logothetis et al., Clin. Cancer Res. 7:1198-1203 (2001).
E. Bråkenhielm, et al., Circulation Research 94(12):1579-88 (2004).
E.C. Griffith et al., Chemistry & Biology 4(6):461-471 (1997).
H.R. Lijnen et al., Obesity 18(12):2241-46 (2010).
Ingber et al., Nature 348:555-57 (1990).
Leszczyniecka et al., Oncogene 25:3471-78 (2006).
M.A. Rupnick et al., Proc. Natl. Acad. Sci. USA 99(16):10730-35 (2002).
P. Bhargava et al., Clin. Cancer Res. 5:1989-95 (1999).
R.S. Herbst et al., J. Clin. Oncology 20(22):4440-47 (2002).
W.M. Stadler et al., J. Clin. Oncology 17(8):2541-45 (1999).
Y.M. Kim, et al., J. Mol. Endocrinology, 38:455-65 (2007).
Z. Hou et al., Organic & Biomolecular Chem. V.11, N.20, 2013, p. 3288-96.

* cited by examiner

*Primary Examiner* — Kamal Saeed
(74) *Attorney, Agent, or Firm* — Matthew J. Russo

(57) ABSTRACT

Disclosed are compounds of Formula 1,

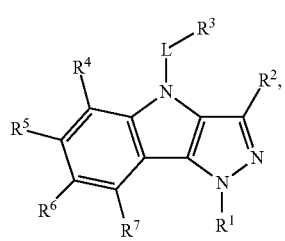

and pharmaceutically acceptable salts thereof, wherein L, $R^1$, $R^2$, $R^3$, $R^4$, $R^5$, $R^6$, and $R^7$ are defined in the specification. This disclosure also relates to materials and methods for preparing compounds of Formula 1, to pharmaceutical compositions which contain them, and to their use for treating obesity and related diseases, disorders, and conditions associated with MetAP2.

17 Claims, No Drawings

SUBSTITUTED-1,4-DIHYDROPYRAZOLO[4,3-B]INDOLES

CROSS-REFERENCE TO RELATED APPLICATIONS

This application is the U.S. National Stage entry under 35 U.S.C. §371(c) of International Application PCT/US2013/058527, filed Sep. 6, 2013, which claims the benefit of U.S. Provisional Application No. 61/698,369, filed Sep. 7, 2012, which is herein incorporated by reference.

FIELD OF THE INVENTION

This invention relates to substituted-1,4-dihydropyrazolo[4,3-b]indoles which are inhibitors of methionine aminopeptidase 2 (MetAP2), to pharmaceutical compositions which contain them, and to their use to treat diseases, disorders, and conditions associated with MetAP2, including obesity.

BACKGROUND OF THE INVENTION

Methionine aminopeptidases are enzymes that bind to cobalt and manganese ions. The metalloenzymes are widely found in prokaryotic and eukaryotic cells, and exist in three forms, MetAP1A, MetAP1D, and MetAP2. See M. Leszczyniecka et al., *Oncogene* 25:3471-78 (2006). They are responsible for the removal of the N-terminal methionine residue from nascent proteins, an important step in protein maturation and likely essential for proper functional regulation, intracellular targeting, and protein turnover. See S. M. Arfin et al., *Proc. Natl. Acad. Sci. USA* 92:7714-18 (1995). Known (irreversible) inhibitors of MetAP2 include the natural product fumagillin and its more potent semi-synthetic analog TNP-470 (AGM-1470). See D. Ingber et al., *Nature* 348:555-57 (1990); see also E. C. Griffith et al., *Chemistry & Biology* 4(6):461-471 (1997). Both compounds inhibit angiogenesis, and TNP-470 has been evaluated in numerous clinical trials as a treatment for cancer. See, e.g., R. S. Herbst et al., *J. Clin. Oncology* 20(22):4440-47 (2002) (non-small cell lung cancer); C. J. Logothetis et al., *Clin. Cancer Res.* 7:1198-1203 (2001) (progressive androgen-dependent prostate cancer); W. M. Stadler et al., *J. Clin. Oncology* 17(8): 2541-45 (1999) (metastatic renal carcinoma); A. P. Kudelka et al, *N. Engl. J. Med.* 338:991-92 (1998) (metastatic cervical cancer); A. P. Kudelka et al., *Clin. Cancer Res.* 3:1501-05 (1997) (squamous cell cancer of the cervix); and P. Bhargava et al., *Clin. Cancer Res.* 5:1989-95 (1999) (sarcoma, colorectal cancer, and melanoma).

Numerous studies also suggest MetAP2 inhibitors may be used to treat obesity. For example, TNP-470 was tested in various mice obesity models and showed dose-dependent, reversible weight reduction and adipose tissue loss. See M. A. Rupnick et al., *Proc. Natl. Acad. Sci. USA* 99(16):10730-35 (2002). TNP-470 has also been shown to prevent diet-induced obesity in mice. See E. Bråkenhielm, et al., *Circulation Research* 94(12):1579-88 (2004). Treatment with fumagillin has been shown to impair diet-induced obesity in mice, as evidenced by adipocyte hypotrophy, but without significantly affecting adipose tissue angiogenesis. See H. R. Lijnen et al., *Obesity* 18(12):2241-46 (2010). Furthermore, a MetAP2 inhibitor, CKD-732, was found to decrease food intake, body weight, fat mass, and the size of adipocytes in genetically and diet-induced obese mice. See Y. M. Kim, et al., *J. Mol. Endocrinology*, 38:455-65 (2007). Recently, CKD-732 (beloranib hemioxalate) has undergone early-phase clinical testing in adult obese patients (e.g., 30≤BMI≤45 kg/m$^2$).

Certain inhibitors of MetAP2 are described in US 2012/004162 A1 and WO 2010/065883 A2.

SUMMARY OF THE INVENTION

This invention provides substituted-1,4-dihydropyrazolo[4,3-b]indole derivatives and related compounds, and pharmaceutically acceptable salts thereof. This invention also provides pharmaceutical compositions that contain the substituted-1,4-dihydropyrazolo[4,3-b]indoles and provides for their use to treat diseases, disorders and conditions associated with MetAP2 inhibition, including obesity.

One aspect of the invention provides compounds of Formula 1:

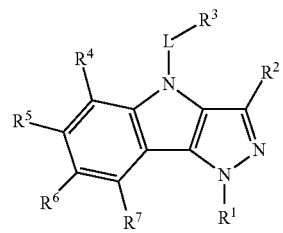

or a pharmaceutically acceptable salt thereof, wherein:
L is selected from a direct bond, $C_{1-4}$ alkanediyl, —C(O)—, —C(O)NH—, and —C(O)NHCH$_2$—;
$R^1$ is hydrogen;
$R^2$ is selected from hydrogen, —OH, chloro, fluoro, —CN, methyl, and hydroxymethyl;
$R^3$ is selected from $C_{6-14}$ aryl, $C_{1-9}$ heteroaryl, $C_{2-6}$ heterocyclyl, and $C_{3-8}$ cycloalkyl, each optionally substituted with from one to five substituents independently selected from halo, oxo, —CN, $R^8$, and $R^9$;
each $R^4$, $R^5$, $R^6$, and $R^7$ is independently selected from hydrogen, —OH, —NH$_2$, halo, $C_{1-4}$ alkyl, and $C_{1-4}$ haloalkyl;
each $R^8$ is independently selected from —OR$^{10}$, —N(R$^{10}$)R$^{11}$, —NR$^{10}$C(O)R$^{11}$, —NHC(O)NR$^{10}$R$^{11}$, —NR$^{10}$C(O)NHR$^{11}$, —C(O)R$^{10}$, —C(O)OR$^{10}$, —C(O)N(R$^{10}$)R$^{11}$, —C(O)N(R$^{10}$)R$^{11}$, —C(O)N(R$^{10}$)S(O)$_2$R$^9$, —N(R$^{10}$)S(O)$_2$R$^9$, —SR$^{10}$, —S(O)R$^9$, —S(O)$_2$R$^9$, and —S(O)$_2$N(R$^{10}$)R$^{11}$;
each $R^9$ is independently selected from
  (a) $C_{1-6}$ alkyl, $C_{2-6}$ alkenyl, and $C_{2-6}$ alkynyl, each optionally substituted with from one to five substituents independently selected from halo, oxo, —CN, and $R^{12}$; and
  (b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, $R^{12}$, and $C_{1-6}$ alkyl optionally substituted with from one to five substituents independently selected from halo, oxo, —CN, and $R^{12}$;
each $R^{10}$ and $R^{11}$ is independently selected from
  (a) hydrogen;
  (b) $C_{1-6}$ alkyl, $C_{2-6}$ alkenyl, and $C_{2-6}$ alkynyl, each optionally substituted with from one to five substituents independently selected from halo, oxo, —CN, and $R^{12}$; and (c) $C_{3-8}$ cycloalkyl-$(CH_2)_m$—, $C_{2-6}$ heterocyclyl-$(CH_2)_m$—, $C_{6-14}$ aryl-$(CH_2)_m$—, and $C_{1-9}$ heteroaryl-$(CH_2)_m$—, each optionally substituted with from one to five substituents independently selected from halo, oxo, —CN, $R^{12}$, and $C_{1-6}$ alkyl optionally substituted with from one to five substituents independently selected from halo, oxo, —CN, and $R^{12}$;

each $R^{12}$ is independently selected from —$OR^{13}$, —$N(R^{13})R^{14}$, —$N(R^{13})C(O)R^{14}$, —$NHC(O)NR^{13}R^{14}$, —$NR^{13}C(O)NHR^{14}$, —$C(O)R^{13}$, —$C(O)OR^{13}$, —$C(O)N(R^{13})R^{14}$, —$C(O)N(R^{13})OR^{14}$, —$C(O)N(R^{13})S(O)_2R^{15}$, —$NR^{13}S(O)_2R^{15}$, —$SR^{13}$, —$S(O)R^{15}$, —$S(O)_2R^{15}$, and —$S(O)_2N(R^{13})R^{14}$;

each $R^{13}$ and $R^{14}$ is independently selected from
(a) hydrogen; and
(b) $C_{1-6}$ alkyl, $C_{3-8}$ cycloalkyl-$(CH_2)_m$—, and $C_{2-6}$ heterocyclyl-$(CH_2)_m$—, each optionally substituted with from one to five substituents independently selected from halo, oxo, —CN, —OH, and —$NH_2$;

each $R^{15}$ is independently selected from $C_{1-6}$ alkyl, $C_{3-8}$ cycloalkyl-$(CH_2)_m$—, and $C_{2-6}$ heterocyclyl-$(CH_2)_m$—, each optionally substituted with from one to five substituents independently selected from halo, oxo, —CN, —OH, and —$NH_2$; and each m is independently selected from 0, 1, 2, 3, and 4;
wherein each heteroaryl and heterocyclyl moiety has from one to four heteroatoms independently selected from N, O, and S.

Another aspect of the invention provides a compound which is selected from the group of compounds described in the examples, their pharmaceutically acceptable salts, and stereoisomers of any of the compounds in the examples and their pharmaceutically acceptable salts.

A further aspect of the invention provides a pharmaceutical composition which includes: a compound of Formula 1 or a pharmaceutically acceptable salt as defined above, or a compound selected from the group of compounds and their pharmaceutically acceptable salts as defined in the preceding paragraph; and a pharmaceutically acceptable excipient.

An additional aspect of the invention provides a compound of Formula 1 or a pharmaceutically acceptable salt as defined above, or a compound selected from the group of compounds and their pharmaceutically acceptable salts as defined above, for use as a medicament.

Another aspect of the invention provides a compound of Formula 1 or pharmaceutically acceptable salt as defined above, or a compound selected from the group of compounds and their pharmaceutically acceptable salts as defined above, for treatment of a disease, disorder or condition selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, and atherosclerosis.

A further aspect of the invention provides a use of a compound of Formula 1 or a pharmaceutically acceptable salt as defined above, or a compound selected from the group of compounds and their pharmaceutically acceptable salts as defined above, for the manufacture of a medicament for the treatment of a disease, disorder or condition associated with MetAP2.

An additional aspect of the invention provides a method of treating a disease, disorder or condition associated with MetAP2, the method comprising administering to the subject an effective amount of a compound of Formula 1 or a pharmaceutically acceptable salt as defined above, or a compound selected from the group of compounds and their pharmaceutically acceptable salts as defined above.

Another aspect of the invention provides a method of treating a disease, disorder or condition in a subject, the method comprising administering to the subject an effective amount of a compound of Formula 1 or a pharmaceutically acceptable salt as defined above, or a compound selected from the group of compounds and their pharmaceutically acceptable salts as defined above, wherein the disease, disorder or condition is selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, and atherosclerosis.

A further aspect of the invention provides an effective amount of a compound of Formula 1 or a pharmaceutically acceptable salt as defined above, or a compound selected from the group of compounds and their pharmaceutically acceptable salts as defined above; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom and may include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings) and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with MetAP2" and similar phrases relate to a disease, disorder or condition in a subject for which inhibition of MetAP2 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexyl-carbodiimide); DCE (1,1-dichloroethane); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (half maximal effective concentration); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); PE (petroleum ether); Ph (phenyl); $pIC_{50}$ ($-\log_{10}(IC_{50})$, where $IC_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl) phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating obesity and other diseases, disorders or conditions associated with MetAP2.

In addition to the specific compounds in the examples, compounds of Formula 1 include those in which (a1) $R^3$ is $C_{6-14}$ aryl optionally substituted with from one to five substituents independently selected from halo, oxo, —CN, $R^8$, and $R^9$; (a2) $R^3$ is $C_{1-9}$ heteroaryl optionally substituted with from one to five substituents independently selected from halo, oxo, —CN, $R^8$, and $R^9$; (a3) $R^3$ is $C_{2-6}$ heterocyclyl optionally substituted with from one to five substituents independently selected from halo, oxo, —CN, $R^8$, and $R^9$; or (a4) $R^3$ is $C_{3-8}$ cycloalkyl optionally substituted with from one to five substituents independently selected from halo, oxo, —CN, $R^8$, and $R^9$.

Compounds of Formula 1 also include those in which (a5) $R^3$ is selected from phenyl, naphthalenyl, and fluorenyl, each optionally substituted with from one to five substituents independently selected from halo, —CN, $R^8$, and $R^9$; (a6) $R^3$ is selected from phenyl and naphthalenyl, each optionally substituted with from one to five substituents independently selected from halo, —CN, $R^8$, and $R^9$; (a7) $R^3$ is phenyl optionally substituted with from one to five substituents independently selected from halo, —CN, $R^8$, and $R^9$; or (a8) $R^3$ is phenyl optionally substituted with from one to three substituents independently selected from halo, —CN, $R^8$, and $R^9$.

Compounds of Formula 1 also include those in which (a9) $R^3$ is selected from pyrrolyl, furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, benzofuranyl, isobenzofuranyl, benzothiopheneyl, benzo[c]thiopheneyl, 1H-indolyl, isoindolyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, benzo[d]thiazolyl, [1,2,4]triazolo[1,5-a]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 5H-pyrrolo[2,3-b]pyrazinyl, imidazo[1,2-a]pyrazinyl, and imidazo[1,2-b]pyridazinyl, each optionally substituted with from one to five substituents independently selected from halo, —CN, $R^8$, and $R^9$.

Compounds of Formula 1 also include those in which (a10) $R^3$ is selected from pyridinyl, pyrimidinyl, pyridazinyl, pyrazinyl, imidazolyl, pyrazolyl, tetrazolyl, thiazolyl, isoxazolyl, quinolinyl, isoquinolinyl, 1,7-naphthyridinyl, 1H-indolyl, benzimidazolyl, 1H-indazolyl, 2H-indazolyl, benzo[d]thiazolyl, 1H-pyrrolo[2,3-b]pyridinyl, 1H-pyrrolo[2,3-c]pyridinyl, imidazo[1,2-a]pyridinyl, pyrazolo[1,5-a]pyridinyl, 3H-imidazo[4,5-b]pyridinyl, [1,2,4]triazolo[1,5-a]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, imidazo[1,2-a]pyrazinyl, imidazo[1,2-b]pyridazinyl, and each optionally substituted with from one to five substituents independently selected from halo, —CN, $R^8$, and $R^9$; (a11) $R^3$ is selected from pyridinyl, pyrimidinyl, pyrazolyl, 1H-indazolyl, 2H-indazolyl, 3H-imidazo[4,5-b]pyridinyl, and [1,2,4]triazolo[1,5-a]pyridinyl each optionally substituted with from one to three substituents independently selected from halo, —CN, $R^8$, and $R^9$; (a12) $R^3$ is pyridinyl optionally substituted with from one to three substituents independently selected from halo, —CN, $R^8$, and $R^9$; (a13) $R^3$ is pyrimidinyl optionally substituted with from one to three substituents independently selected from halo, —CN, $R^8$, and $R^9$; (a14) $R^3$ is pyrazolyl optionally substituted with from one to three substituents independently selected from halo, —CN, $R^8$, and $R^9$; (a15) $R^3$ is 1H-indazolyl optionally substituted with from one to three substituents independently selected from halo, —CN, $R^8$, and $R^9$; (a16) $R^3$ is 2H-indazolyl optionally substituted with from one to three substituents independently selected from halo, —CN, $R^8$, and $R^9$; (a17) $R^3$ is 3H-imidazo[4,5-b]pyridinyl optionally substituted with from one to three substituents independently selected from halo, —CN, $R^8$, and $R^9$; or (a18) $R^3$ is [1,2,4]triazolo[1,5-a]pyridinyl optionally substituted with from one to three substituents independently selected from halo, —CN, $R^8$, and $R^9$.

Compounds of Formula 1 also include those in which (a19) $R^3$ is selected from 3H-indolyl, 1H-isoindolyl, indolinyl, isoindolinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, 2,3-dihydro-1H-pyrrolo[2,3-b]pyridinyl, 2,3-dihydro-1H-imidazo[4,5-b]pyridinyl, 4,5-dihydro-1H-pyrazolo[3,4-d]pyrimidinyl, 2,3,6,7-tetrahydro-1H-purinyl, and 4,5,6,7-tetrahydropyrazolo[1,5-a]pyrazinyl, each optionally substituted with from one to five substituents independently selected from halo, oxo, —CN, $R^8$, and $R^9$.

Compounds of Formula 1 also include those in which (a20) $R^3$ is selected from 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, indolinyl, isoindolinyl, 2,3-dihydro-1H-benzo[d]imidazolyl, 2,3-dihydro-1H-pyrrolo[2,3-b]pyridinyl, 2,3-dihydro-1H-imidazo[4,5-b]pyridinyl, 4,5-dihydro-1H-pyrazolo[3,4-d]pyrimidinyl, 2,3,6,7-tetrahydro-1H-purinyl, 5H-pyrrolo[2,3-b]pyrazinyl, and 4,5,6,7-tetrahydropyrazolo[1,5-a]pyrazinyl, each optionally substituted with from one to five substituents independently selected from halo, oxo, —CN, $R^8$, and $R^9$; (a21) $R^3$ is selected from 2,3-dihydro-1H-imidazo[4,5-b]pyridinyl and 4,5,6,7-tetrahydropyrazolo[1,5-a]pyrazinyl each optionally substituted with from one to five substituents independently selected from halo, oxo, —CN, $R^8$, and $R^9$; (a22) $R^3$ is 2,3-dihydro-1H-imidazo[4,5-b]pyridinyl optionally substituted with from one to five substituents independently selected from halo, oxo, —CN, $R^8$, and $R^9$; or (a23) $R^3$ is selected from 4,5,6,7-tetrahydropyrazolo[1,5-a]pyrazinyl optionally substituted with from one to five substituents independently selected from halo, oxo, —CN, $R^8$, and $R^9$.

Compounds of Formula 1 also include those in which (a24) $R^3$ is selected from oxiranyl, thiiranyl, aziridinyl, oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl, each optionally substituted with from one to five substituents independently selected from halo, —CN, $R^8$, and $R^9$.

Compounds of Formula 1 also include those in which (a25) $R^3$ is selected from 1,2-dihydropyridinyl, 1,6-dihydropyrimidinyl, 1,2,3,4-tetrahydropyrimidinyl, and 1,2-dihydropyrazolo[1,5-d][1,2,4]triazinyl, each optionally substituted with from one to five substituents independently selected from halo, oxo, —CN, $R^8$, and $R^9$; (a26) $R^3$ is selected from 1,2-dihydropyridinyl and 1,6-dihydropyrimidinyl, each optionally substituted with from one to five substituents independently selected from halo, oxo, —CN, $R^8$, and $R^9$; (a27) $R^3$ is 1,2-dihydropyridinyl optionally substituted with from one to five substituents independently selected from halo, oxo, —CN, $R^8$, and $R^9$; or (a28) $R^3$ is selected from 1,6-dihydropyrimidinyl optionally substituted with from one to five substituents independently selected from halo, oxo, —CN, $R^8$, and $R^9$.

In addition, or as an alternative, to one of embodiments (a1) through (a28) in the preceding paragraphs, compounds of Formula 1 include those in which (b1) $R^3$ is optionally substituted with from one to three substituents; (b2) $R^3$ is optionally substituted with one or two substituents; (b3) $R^3$ is optionally substituted with one substituent; or (b4) $R^3$ is unsubstituted (i.e., contains no optional substituents).

In addition, or as an alternative, to one of embodiments (a1) through (a28) in the preceding paragraphs, and to one of embodiments (b1) through (b4) in the preceding paragraph, compounds of Formula 1 include those in which (c1) L is selected from direct bond, —CH$_2$—, —C(O)—, and —C(O)NH—; (c2) L is selected from direct bond, —CH$_2$—, and —C(O)NH—; (c3) L is selected from direct bond and —CH$_2$—; or (c4) L is a direct bond.

In addition, or as an alternative, to one of embodiments (a1) through (a28) in the preceding paragraphs, and to one or more of embodiments (b1) through (c4) in the preceding paragraphs, compounds of Formula 1 include those in which (d1) $R^2$ is selected from hydrogen, —OH, chloro, and fluoro; (d2) $R^2$ is selected from hydrogen, chloro, and fluoro; (d3) $R^2$ is selected from hydrogen and fluoro; or (d4) $R^2$ is hydrogen.

In addition, or as an alternative, to one of embodiments (a1) through (a28) in the preceding paragraphs, and to one or more of embodiments (b1) through (d4) in the preceding paragraphs, compounds of Formula 1 include those in which (e1) $R^4$ is selected from hydrogen, —OH, —NH$_2$, halo, and methyl; (e2) $R^4$ is selected from hydrogen, chloro, fluoro, and methyl; (e3) $R^4$ is selected from hydrogen and fluoro; or (e4) $R^4$ is hydrogen.

In addition, or as an alternative, to one of embodiments (a1) through (a28) in the preceding paragraphs, and to one or more of embodiments (b1) through (e4) in the preceding paragraphs, compounds of Formula 1 include those in which (f1) $R^5$ is selected from hydrogen, —OH, —NH$_2$, halo, and methyl; (f2) $R^5$ is selected from hydrogen, chloro, fluoro, and methyl; (f3) $R^5$ is selected from hydrogen, chloro, and fluoro; (f4) $R^5$ is chloro; (f5) $R^5$ is fluoro; or (f6) $R^5$ is hydrogen.

In addition, or as an alternative, to one of embodiments (a1) through (a28) in the preceding paragraphs, and to one or more of embodiments (b1) through (f6) in the preceding paragraphs, compounds of Formula 1 include those in which (g1) $R^6$ is selected from hydrogen, —OH, —NH$_2$, halo, and methyl; (g2) $R^6$ is selected from hydrogen, chloro, fluoro, and methyl; (g3) $R^6$ is selected from hydrogen, chloro, and fluoro; (g4) $R^6$ is chloro; (g5) $R^6$ is fluoro; or (g6) $R^6$ is hydrogen.

In addition, or as an alternative, to one of embodiments (a1) through (a28) in the preceding paragraphs, and to one or more of embodiments (b1) through (g6) in the preceding paragraphs, compounds of Formula 1 include those in which (h1) $R^7$ is selected from hydrogen, —OH, —NH$_2$, halo, and methyl; (h2) $R^7$ is selected from hydrogen, chloro, fluoro, and methyl; (h3) $R^7$ is selected from hydrogen and fluoro; or (h4) $R^7$ is hydrogen.

In addition, or as an alternative, to one of embodiments (a1) through (a28) in the preceding paragraphs, and to one or more of embodiments (b1) through (h4) in the preceding paragraphs, compounds of Formula 1 include those in which (i1) each $R^9$, $R^{10}$, and $R^{11}$ substituent is optionally substituted with one or two substituents; (i2) each $R^9$, $R^{10}$, and $R^{11}$ substituent is optionally substituted with one substituent; or (i3) each $R^9$, $R^{10}$, and $R^{11}$ substituent is unsubstituted (i.e., contains no optional substituents).

In addition, or as an alternative, to one of embodiments (a1) through (a28) in the preceding paragraphs, and to one or more of embodiments (b1) through (i3) in the preceding paragraphs, compounds of Formula 1 include those in which (j1) each $R^{13}$, $R^{14}$, and $R^{15}$ substituent is optionally substituted with one or two substituents; (j2) each $R^{13}$, $R^{14}$, and $R^{15}$ substituent is optionally substituted with one substituent; or (j3) each $R^{13}$, $R^{14}$, and $R^{15}$ substituent is unsubstituted.

In addition, or as an alternative, to one of embodiments (a1) through (a28) in the preceding paragraphs, and to one or more of embodiments (b1) through (j3) in the preceding paragraphs, compounds of Formula 1 include those in which (k1) each m is independently selected from 0, 1, 2, and 3; (k2) each m is independently selected from 0, 1, and 2; (k3) each m is independently selected from 0 and 1; or (k4) each m is 0.

In addition, or as an alternative, to one of embodiments (a1) through (a28) in the preceding paragraphs, and to one or more of embodiments (b1) through (k4) in the preceding paragraphs, compounds of Formula 1 include those in which (l1) $R^2$, $R^4$, and $R^7$ are each hydrogen, and $R^5$ and $R^7$ are each independently selected from hydrogen, chloro, and fluoro; or (l2) $R^2$, $R^4$, $R^5$, and $R^7$ are each hydrogen, and $R^7$ is fluoro.

Compounds of Formula 1 include embodiments (a1) through (l2) described in the preceding paragraphs and all compounds specifically named above and in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $-COO^-Na^+$, $-COO^-K^+$, $-SO_3^-Na^+$) or polar non-ionic moiety (such as $-N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the scheme, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^2$ substituent having a potentially reactive amine. In such cases, $R^2$ would include the moiety with or without, say, a Boc or Cbz group attached to the amine.

Scheme A shows a general method for preparing compounds of Formula 1. According to the method, an aryl amino halide or pseudohalide (A1, where X is Br, Cl, I, triflate, etc.) undergoes diazotization via reaction with aqueous sodium nitrite and hydrochloric acid at reduced temperature (5° C. or less). The resulting diazonium salt (not shown) is treated with aqueous sodium azide to give an azidobenzene derivative (A2). The azidobenzene derivative (A2) is subsequently reacted with a boronic acid or ester of a THP-protected pyrazole (A3, where Y is —B(OR')$_2$, each R' is H or $C_{1-4}$ alkyl or each R' together forms a $C_{1-8}$ alkanediyl such as 2,3-dimethylbutan-2,3-diyl) to give an azidophenyl pyrazole (A4). The Suzuki coupling is carried out at elevated temperature in the presence of a palladium catalyst (e.g., Pd(PPh$_3$)$_4$, (PPh$_3$)$_2$PdCl$_2$, PdCl$_2$(dppf), etc.), a base (e.g., KF, Na$_2$CO$_3$, NaHCO$_3$, Cs$_2$CO$_3$) and one or more solvents (e.g., dioxane, DCM, DME, DMF, H$_2$O, etc.). Heating the azidophenyl pyrazole (A4) at elevated temperature (e.g., 170° C.) in a high boiling solvent (e.g., 1,2-dichlorobenzene) gives a 1,4-dihydropyrazolo[4,3-b]indole derivative (A5).

As shown in Scheme A, the 1,4-dihydropyrazolo[4,3-b]indole derivative (A5) is subsequently reacted with R$^3$—Z (where Z is —CH$_2$X, —(CH$_2$)$_{0-1}$NCO or —C(O)X) in the presence of an inorganic or non-nucleophilic base (KOH, Et$_3$N, etc.) and one or more compatible solvents (EtOH, DMF, etc.) to give a 4-substituted-1,4-dihydropyrazolo[4,3-b]indole (A6). Alternatively, the 1,4-dihydropyrazolo[4,3-b]indole derivative (A5) may be reacted with R$^3$—X (where X is Br, Cl, I, triflate, etc.) at elevated temperature in the presence of a palladium or copper catalyst. Useful palladium catalysts include, e.g., a palladium source, such as Pd$_2$(dba)$_3$, Pd(OAc)$_2$, etc., and a ligand, such as tri-tert-butylphosphine, triisopropylphosphine, di-tert-butylmethylphosphine, etc. Useful copper catalysts include copper(I) thiophene-2-carboxylate, copper(I) iodide, etc. The palladium- and copper-catalyzed couplings are carried out in a base (e.g., K$_2$CO$_3$, Cs$_2$CO$_3$, NaOt-Bu, KOt-Bu, etc.) and in one or more organic solvents (e.g., xylene, dioxane, toluene, etc.). Following the aryl coupling, the 4-substituted-1,4-dihydropyrazolo[4,3-b]indole (A6) is treated with concentrated hydrochloric acid to remove the THP group, which gives the compound of Formula 1. The acid hydrolysis is carried out in the presence of MeOH or EtOH.

The method depicted in Scheme A may be varied as desired. For example, protecting groups may be added or removed at various steps in the route. In addition, the intermediates may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Scheme A

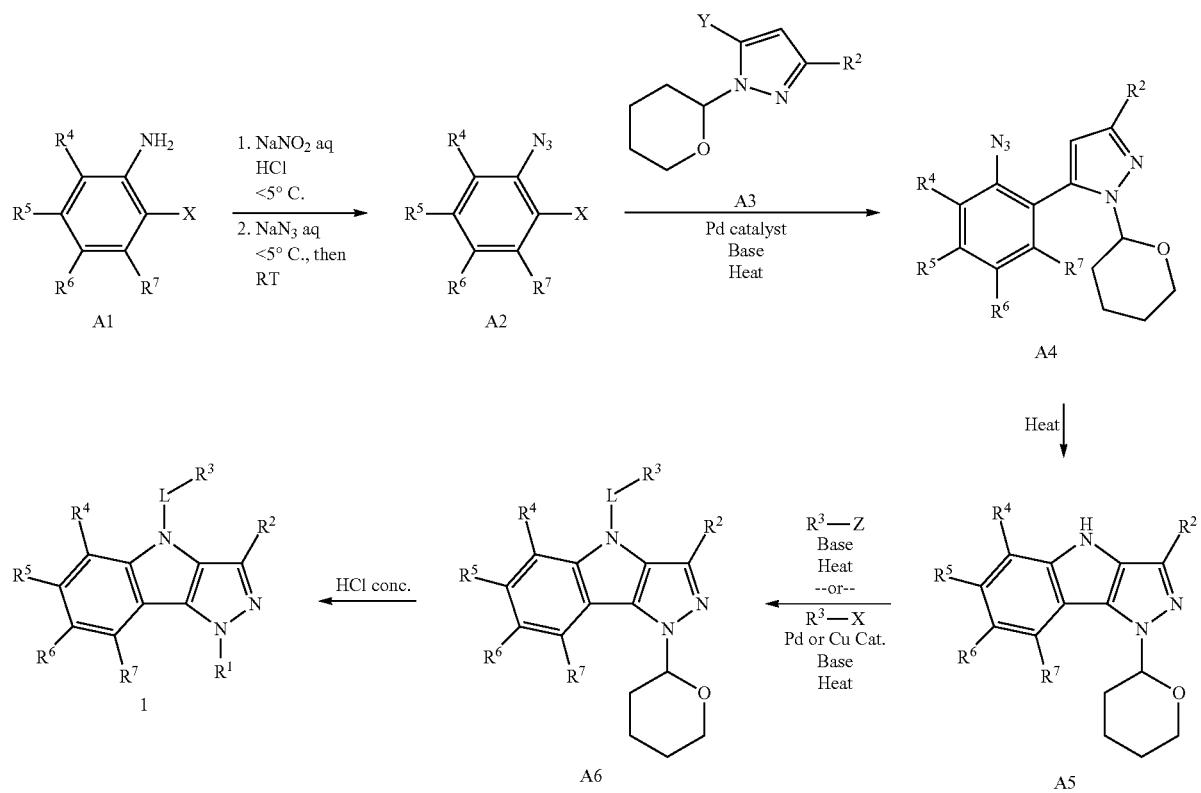

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which inhibition of MetAP2 is indicated. Such diseases, disorders, and conditions generally relate to any unhealthy or abnormal state in a subject for which the inhibition of MetAP2 provides a therapeutic benefit. More particularly, the compounds of Formula 1 may be used to treat obesity or an overweight condition in a subject, or to treat diseases, disorders or conditions associated with obesity or an overweight condition, including cardiovascular disease, hypertension, diabetes, hyperglycemia, insulin resistance, metabolic syndrome X, impaired glucose tolerance, non-alcoholic liver steatosis, dyslipidemia (including high total cholesterol or high levels of triglycerides), atherosclerosis, stroke, sleep apnea, osteoarthritis, infertility, and polycystic ovary syndrome.

According to *The Practical Guide: Identification, Evaluation, and Treatment of Overweight and Obesity in Adults*, published in 2000 by the National Heart, Lung, and Blood Institute, a human adult may be classified as overweight or obese based upon the subject's body mass index (BMI). BMI is calculated by dividing a subject's mass (in kg) by the square of the subject's height (in meters). Under the Guide, a BMI of 25-29.9 kg/m$^2$ is classified as overweight, and body mass indices of 30-34.9 kg/m$^2$, 35-39.9 kg/m$^2$, and ≥40 kg/m$^2$ are classified as Class 1 obesity, Class 2 obesity, and Class 3 (extreme) obesity, respectively.

The claimed and disclosed compounds may be combined with one or more other pharmacologically active compounds or therapies to treat one or more disorders, diseases or conditions for which MetAP2 is indicated, including obesity. For example, compounds of Formula 1, which include compounds specifically named above, and their pharmaceutically acceptable complexes, salts, solvates and hydrates, may be administered simultaneously, sequentially or separately in combination with one or more compounds or therapies for treating cardiovascular disease, hypertension, diabetes, hyperglycemia, insulin resistance, metabolic syndrome X, impaired glucose tolerance, non-alcoholic liver steatosis, dyslipidemia, atherosclerosis, stroke, sleep apnea, osteoarthritis, infertility, and polycystic ovary syndrome. Such combinations may offer significant therapeutic advantages, including fewer side effects, improved ability to treat underserved patient populations, or synergistic activity.

For example, the compounds of Formula 1 may be combined with one or more agents for treating obesity, diabetes, hyperglycemia, insulin resistance, metabolic syndrome X, impaired glucose tolerance, and non-alcoholic liver steatosis. These agents include pancreatic lipase inhibitors (e.g., orlistat); insulin; insulin sensitizers, including biguanides (e.g., buformin, metformin, and phenformin) and glitazones (e.g., pioglitazone and rosiglitazone); insulin secretagogues, including sulfonylureas (e.g., acetohexamide, chlorpropamide, tolazamide, tolbutamide, gliclazide, glimepiride, glipizide, and glyburide), and meglitinides (e.g., nateglinide and repaglinide); alpha-glucosidase inhibitors (e.g., acarbose and miglitol); glucagon-like peptide analogs and agonists (e.g., exenatide, liraglutide, and taspoglutide); dipeptidyl peptidase-4 inhibitors (e.g., alogliptin, linagliptin, saxagliptin, sitagliptin, and vildagliptin); and amylin analogs (e.g., pramlinitide).

In addition, the compounds of Formula 1 may be combined with one or more agents for treating osteoarthritis, including nonsteroidal anti-inflammatory drugs (NSAIDs) (e.g., apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac); analgesics (e.g., acetaminophen and morphine sulfate, as well as codeine, hydrocodone, oxycodone, propoxyphene, and tramadol, all with or without acetaminophen); corticosteroids (e.g., betamethasone, cortisone acetate, dexamethasone, hydrocortisone, methylprednisolone, prednisolone, and prednisone); and osteoporosis agents (e.g., alendronate, clodronate, etidronate, ibandronate, neridronate, olpadronate, pamidronate, risedronate, tiludronate, and zoledronate).

The compounds of Formula 1 may also be combined with one or more agents for treating cardiovascular disease, hypertension, dyslipidemia, atherosclerosis, and stroke, including calcium channel blockers (e.g., amlodipine, aranidipine, azelnidipine, barnidipine, bepridil, benidipine, cilnidipine, clevidipine, diltiazem, isradipine, efonidipine, felodipine, fendiline, fluspirilene, lacidipine, lercanidipine, manidipine, mibefradil, nicardipine, nifedipine, nilvadipine, nimodipine, nisoldipine, nitrendipine, pranidipine, and verapamil); statins (e.g., atorvastatin, fluvastatin, lovastatin, mevastatin, pitavastatin, pravastatin, rosuvastatin, and simvastatin); PPAR alpha activators (e.g., fibrates, such as bezafibrate, ciprofibrate, clofibrate, fenofibrate, and gemfibrozil); bile acid sequestrants (e.g., cholestyramine, colesevelam, and colestipol); other lipid-lowering agents (e.g., niacin and ezetimibe); beta-blockers (e.g., alprenolol, atenolol, betaxolol, bisoprolol, bucindolol, carteolol, carvedilol, celiprolol, esmolol, eucommia bark, labetalol, metoprolol, nadolol, nebivolol, oxprenolol, penbutolol, pindolol, propranolol, sotalol, and timolol); angeotensin-converting enzyme (ACE) inhibitors (benazepril, captopril, enalapril, imidapril, lisinopril, perindopril, quinapril, ramipril, trandolapril, and zofenopril); and platelet aggregation inhibitors (abciximab, aspirin, cilostazol, clopidogrel, dipyridamole, dipyridamole, eptifibatide, ifetroban, picotamide, prasugrel, terutroban, ticagrelor, ticlopidine, and tirofiban).

Biological Activity

The biological activity of the compound of Formula 1 may be determined using various in vitro and in vivo methods. The following in vitro assays measure a test compound's ability to inhibit MetAP2.

MetAP2 Protein Purification

DNA encoding the full-length sequence of human MetAP2 enzyme is amplified by PCR and cloned into a pFastBac expression vector (Invitrogen). Recombinant baculovirus incorporating the MetAP2 construct is generated by transposition using the Bac-to-Bac system (Invitrogen). The expression of recombinant protein is carried out by infection of *Spodoptera frugiperda* Sf9 cells (Invitrogen) in 5L Wave Bioreactors (Wave Biotech). Recombinant protein is isolated from cellular extracts by binding to an SP Hitrap Fast Flow or SP Sepharose (Sigma) column, and the protein is eluted using a NaCl gradient. Partially purified extracts of MetAP2 are further purified by an AKTA FPLC over a Superdex-200 column (GE). The purity of MetAP2 protein is determined on denaturing SDS-PAGE gel. Purified MetAP2 protein is concentrated to a final concentration of 17 mg/mL or 2.5 mg/mL. The protein is stored at −78° C. in a buffer containing 10 mM HEPES pH 7.4, 150 mM NaCl, and 1 mM CoCl$_2$ or in a buffer containing 20 mM HEPES pH 7.4, 120 mM NaCl, and 5 mM MnCl$_2$.

Enzyme Assay

The inhibition of MetAP2 is determined using a black 384-well-plate format under the following reaction conditions: 50 mM Hepes pH 7.5, 100 mM NaCl, 10 µM MnCl$_2$ or 10 µM CoCl$_2$, 0.005% Brij35®, 1 mM TCEP, 1% DMSO.

To initiate the assay, 4 μL of 5 to 50 nM MetAP2 enzyme solution (enzyme final concentration is 2 to 20 nM) is added to each well, followed by the addition of 2 μL of the test compound (2.5-fold serial dilutions for 11 data points for each test compound) in a buffer solution containing 5% DMSO. Next, 4 μL of a substrate solution (2.5×$K_m$ of Met-AMC) is added to each well of the plate (final substrate concentration at $K_m$ value). The reaction rate is monitored by reading fluorescence at 460 nm with excitation wavelength at 330 nm for 10 to 30 minutes using a fluorescence plate reader. The results for each well are expressed as percent inhibition and calculated using the equation:

$$\text{Inhibition} = 1 - \left(\frac{x - \overline{\text{Positive}}}{\overline{\text{Negative}} - \overline{\text{Positive}}}\right),$$

where $\overline{\text{Negative}}$ is the average of all the rates on the plate in the presence of no test compound, $\overline{\text{Positive}}$ is the rate with a 10 μM tool compound (MetAP2 activity is 100% inhibited), and x is the rate (raw data) in the presence of the test compound. The $IC_{50}$ for each test compound is obtained by fitting the percent inhibition data with a standard 4-parameter equation and is reported as $pIC_{50}$, i.e., $-\log(IC_{50})$, where $IC_{50}$ is the molar concentration at 50% inhibition.

MetAP2 Cellular Activity: Western Blotting of NMet-14-3-3γ

HUVEC cells (Lonza) are seeded in 96-well tissue culture microplates and cultured for 24 hours prior to addition of test compounds (11 point range of serial dilutions) or DMSO vehicle. After 24 hours, whole cell extracts are prepared by lysing cells in cell extraction buffer (Cell Signaling) containing protease and phosphatase inhibitors (Calbiochem). Insoluble material is removed by centrifugation and samples are diluted and boiled in SDS-PAGE buffer. Proteins are resolved by SDS-PAGE and transferred to PVDF membranes. Membranes are blocked then incubated with the appropriate primary antibodies, NMet-14-3-3γ (Novus) and β-actin (Sigma), followed by incubation with secondary IRDye 680- or 800CW-conjugated antibodies (Li-Cor). Membranes are scanned on the Odyssey (Li-Cor) and signals corresponding to N-Met14-3-3γ and β-actin are quantified using LiCor software. Compound $EC_{50}$s are obtained by curve-fitting the ratios of unprocessed N-Met14-3-3γ protein signal over β-actin protein signal using XLfit4 Microsoft Excel curve-fitting software.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5μ C18 110A, Axia™, 30×75 mm, 5μ) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation x1

(S)-1-(5-Bromo-4-methylpyrimidin-2-yl)pyrrolidin-3-ol

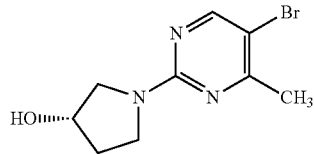

5-Bromo-2-chloro-4-methylpyrimidine (200 mg, 0.964 mmol), (S)-pyrrolidin-3-ol hydrochloride (0.596 g, 4.82 mmol), and N-ethyl-N-isopropylpropan-2-amine (0.504 mL, 2.89 mmol), and ethanol (6 mL) were combined in a 40 mL vial to give a yellow solution. The reaction mixture was stirred at 75° C. for 18 hours. The mixture was subsequently diluted with EtOAc (75 mL), washed with water (30 mL), dried over $Na_2SO_4$, and concentrated to give the title compound as an off-white solid which was used without further purification (1.25 g, 100%).

Preparation x2

(R)-1-(5-bromo-6-methylpyridin-2-yl)pyrrolidin-3-ol

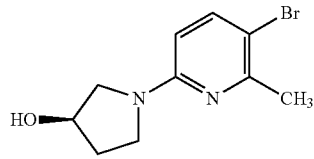

3-Bromo-6-chloro-2-methylpyridine (350 mg, 1.695 mmol), (R)-pyrrolidin-3-ol (148 mg, 1.695 mmol), $Et_3N$ (0.709 mL, 5.09 mmol) and DMF (4 mL) were mixed in an 8 mL tube equipped with a magnetic stir bar to give an orange solution. The tube was sealed and the mixture was heated in a microwave to 150° C. for 1 hour. The reaction mixture was subsequently partitioned between water (20 mL) and EtOAc (20 mL). The layers were separated. The aqueous layer was back-extracted with EtOAc (20 mL) and the combined organic layers were concentrated to yield a brown syrup. The residue was purified via flash chromatography (12 g column), eluting with 0-80% EtOAc in heptanes. The pure fractions were combined and concentrated to give the title compound as a clear liquid (144 mg, 33.0%). MS [M+H]+ calc'd for $C_{10}H_{13}BrN_2O$, 257.03; found 257.0.

Preparation x3

6-Bromo-5-methyl-1H-imidazo[4,5-b]pyridin-2(3H)-one

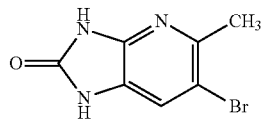

5-Bromo-6-methylpyridine-2,3-diamine (0.930 g, 4.60 mmol) and urea (0.912 g, 15.19 mmol) in N-methyl-2-pyrrolidinone (8 mL) were heated at 140° C. under nitrogen for 5 days. The mixture was subsequently diluted with water. The resulting precipitate was collected by filtration, washed with water, and dried in vacuum oven at 60° C. to give the title compound as a tan solid, which was used without further purification (0.955 g, 91%).

Preparation x4 tert-Butyl 6-bromo-1-(2-hydroxyethyl)-5-methyl-2-oxo-1H-imidazo[4,5-b]pyridine-3(2H)-carboxylate

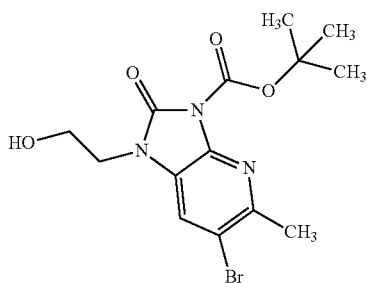 [SMILES: Cc1nc2c(cc1Br)n(CCO)c(=O)n2C(=O)OC(C)(C)C]

Step A: Ethyl 6-bromo-5-methyl-2-oxo-2,3-dihydro-1H-imidazo[4,5-b]pyridine-1-carboxylate

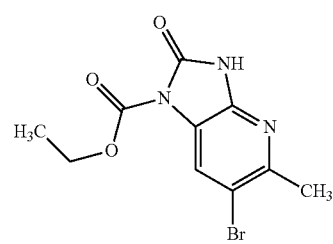 [SMILES: CCOC(=O)n1c(=O)[nH]c2nc(C)c(Br)cc21]

6-Bromo-5-methyl-1H-imidazo[4,5-b]pyridin-2(3H)-one (1.00 g, 4.39 mmol), ethyl pyridin-2-yl carbonate (0.982 g, 5.88 mmol), potassium carbonate (0.812 g, 5.88 mmol) and acetonitrile (12 mL) were combined in a 250 mL round-bottom flask to give a brown suspension. The mixture was heated at reflux for 4 hours and was subsequently concentrated, diluted with water, and acidified to pH 7 with 1 N HCl. A precipitate was collected by filtration, washed with water, and dried in a vacuum oven at 60° C. to give crude title compound as a dark brown solid (1.08 g, 82%).

Step B: tert-Butyl 6-bromo-5-methyl-2-oxo-1H-imidazo[4,5-b]pyridine-3(2H)-carboxylate

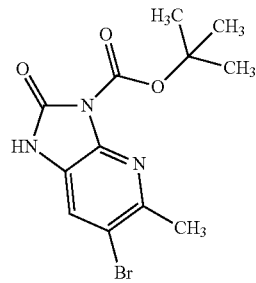 [SMILES: Cc1nc2c(cc1Br)[nH]c(=O)n2C(=O)OC(C)(C)C]

Ethyl 6-bromo-5-methyl-2-oxo-2,3-dihydro-1H-imidazo[4,5-b]pyridine-1-carboxylate (1.08 g, 3.60 mmol) and DMAP (catalytic amount) in THF (12 mL) were combined in a 250 mL round-bottom flask to give a tan suspension. A 1 M di-tert-butyl dicarbonate solution in THF (4.32 mL, 4.32 mmol) was added and the reaction mixture was stirred at room temperature for 2 hours. Propan-2-amine (0.368 mL, 4.32 mmol) was added and the reaction mixture was stirred at room temperature for another hour. The mixture was concentrated to yield a residue, which was triturated with Et₂O to give crude title compound as a tan solid (0.607 g, 51%).

Step C: tert-Butyl 6-bromo-1-(2-hydroxyethyl)-5-methyl-2-oxo-1H-imidazo[4,5-b]pyridine-3 (2H)-carboxylate To a 40 mL vial containing tert-butyl 6-bromo-5-methyl-2-oxo-1H-imidazo[4,5-b]pyridine-3(2H)-carboxylate (200 mg, 0.609 mmol) in DMF (3 mL) was added sodium hydride (21.94 mg, 0.914 mmol) to give a tan suspension. After stirring at room temperature for 30 minutes, 2-bromoethanol (76 mg, 0.609 mmol) was added and the solution was stirred overnight. The reaction was quenched with water and the product extracted into EtOAc. The organic layer was dried over Na₂SO₄ and concentrated to give the title compound, which was used without further purification.

Preparation x5

(S)-1-(5-bromo-6-methylpyridin-2-yl)pyrrolidin-3-ol

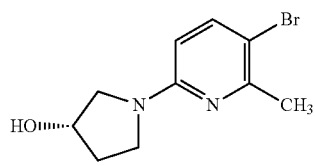

3-Bromo-6-chloro-2-methylpyridine (350 mg, 1.695 mmol), (S)-pyrrolidin-3-ol hydrochloride (272 mg, 2.204 mmol), Et₃N (0.709 mL, 5.09 mmol) and DMF (4 mL) were mixed in a 5 mL tube equipped with a magnetic stir bar to give an orange solution. The tube was sealed and the mixture was heated for 2 hours at 150° C. in a microwave. The reaction mixture was subsequently partitioned between water (20 mL) and EtOAc (20 mL). The layers were separated and the aqueous layer was back-extracted with EtOAc (20 mL). The combined organic layers were concentrated and the residue was purified via flash chromatography (12 g column), eluting with 0-80% EtOAc in heptanes. The pure fractions were combined and concentrated to give the title compound as a tan solid (80 mg, 18%).

Preparation ×6

4-Bromo-5-(methoxymethyl)-1-((2-(trimethylsilyl)ethoxy)methyl)-1H-pyrazole

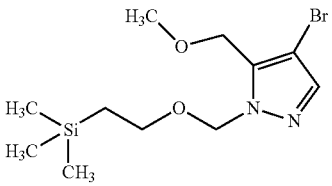 [SMILES: COCc1c(Br)cnn1COCC[Si](C)(C)C]

Step A: Methyl 4-bromo-1-((2-(trimethylsilyl)ethoxy)methyl)-1H-pyrazole-5-carboxylate

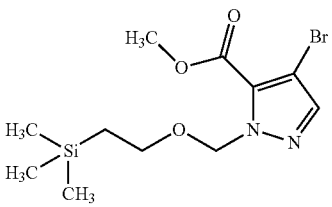 [SMILES: COC(=O)c1c(Br)cnn1COCC[Si](C)(C)C]

To a solution of methyl 4-bromo-1H-pyrazole-5-carboxylate (4.53 g, 204 mmol, 1.0 eq) in DMF (50 mL) was added NaH (60% wt, 1.33 g, 1.5 eq) at 0° C. After 30 minutes at 0° C., (2-(chloromethoxy)ethyl)trimethylsilane (4.44 g, 1.2 eq) was added dropwise. The reaction mixture was allowed to warm to room temperature and was stirred overnight. The reaction mixture was subsequently concentrated and was partitioned between water (10 mL) and EtOAc (3×20 mL). The combined organic layers were concentrated and the residue was purified via flash chromatography, eluting with petroleum ether and EtOAc (20:1) to give the title compound as an oil (6.2 g, 83.6%). MS [M+H]⁺ calc'd for C₁₁H₁₉BrN₂O₃Si, 335.04; found 335.

Step B: (4-Bromo-1-((2-(trimethylsilyl)ethoxy)methyl)-1H-pyrazol-5-yl)methanol

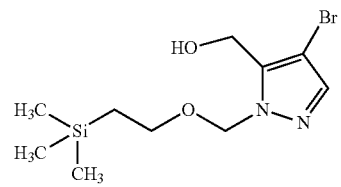

To a solution of methyl 4-bromo-1-((2-(trimethylsilyl)ethoxy)methyl)-1H-pyrazole-5-carboxylate (5.6 g, 334 mmol, 1.0 eq) in dry THF (50 mL) at −78° C. was added LiAlH₄ (2.4N, 3.5 mL, 0.5 eq) dropwise. The reaction mixture was stirred at −78° C. for 20 minutes and was then allowed to warm to room temperature. After 20 minutes, water (5 mL) was added dropwise and the solids were filtered. The filtrate was concentrated to give title compound as an oil (4.2 g, 82%). The crude intermediate was used without further purification. MS [M+H]⁺ calc'd for C₁₀H₁₉BrN₂O₂Si, 307.05; found 307.

Step C: 4-Bromo-5-(methoxymethyl)-1-((2-(trimethylsilyl)ethoxy)methyl)-1H-pyrazole To a solution of (4-bromo-1-((2-(trimethylsilyl)ethoxy)methyl)-1H-pyrazol-5-yl)methanol (4.0 g crude, 13.07 mmol, 1.0 eq) in dry THF (50 mL) at 0° C. was added NaH (60% wt, 0.78 g, 1.5 eq) portion-wise. The mixture was stirred at 0° C. for 30 minutes. Iodomethane (2.78 g, 1.5 eq) was subsequently added dropwise and the reaction mixture was allowed to warm to room temperature. The reaction mixture was concentrated and was partitioned between water (10 mL) and EtOAc (3×20 mL). The combined organic layers were concentrated and the residue was purified via flash chromatography, eluting with petroleum ether and EtOAc (40:1) to give the title compound as an oil (2.0 g, 48%). ¹H NMR (300 MHz, CDCl₃) δ ppm 7.47 (s, 1H), 5.52 (s, 2H), 4.57 (s, 2H), 3.59-3.53 (t, 2H, J=8.1 Hz), 3.35 (s, 3H), 0.93-0.87 (t, 2H, J=7.8 Hz), 0.00 (s, 9H).

Preparation ×7

6-Bromo-3,5-dimethyl-3H-imidazo[4,5-b]pyridine

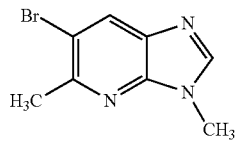

6-Bromo-5-methyl-3H-imidazo[4,5-b]pyridine (235 mg, 1.11 mmol), NaH (44.3 mg, 1.108 mmol) and DMF (2 mL) were mixed in a 20 mL vial equipped with a magnetic stir bar to give a brown suspension. After a few minutes, iodomethane (0.069 mL, 1.108 mmol) was added and the mixture was stirred overnight. The reaction mixture was subsequently partitioned between water (30 mL) and EtOAc (30 mL). The layers were separated and the aqueous layer was back-extracted with EtOAc (25 mL). The combined organic layers were concentrated to yield a pink solid, which was purified via flash chromatography (12 g column), eluting with 0-70% EtOAc in heptanes. The pure fractions were combined and concentrated to give the title compound as a peach colored solid (100 mg, 39.9%).

Preparation x8

(S)-6-Bromo-3-((2,2-dimethyl-1,3-dioxolan-4-yl)methyl)-5-methyl-1H-imidazo[4,5-b]pyridin-2(3H)-one

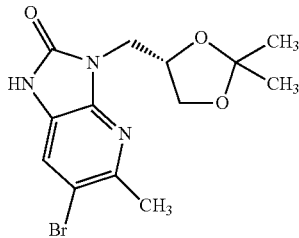 [SMILES: Cc1nc2c(cc1Br)[nH]c(=O)n2C[C@H]1COC(C)(C)O1]

Step A: (S)-5-Bromo-N-((2,2-dimethyl-1,3-dioxolan-4-yl)methyl)-6-methyl-3-nitropyridin-2-amine

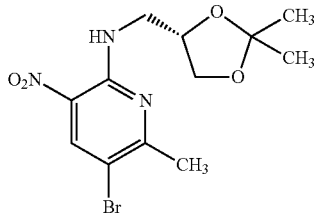 [SMILES: Cc1nc(NC[C@H]2COC(C)(C)O2)c([N+](=O)[O-])cc1Br]

2,5-Dibromo-6-methyl-3-nitropyridine (2.121 g, 7.17 mmol), (S)-(2,2-dimethyl-1,3-dioxolan-4-yl)methanamine (0.94 g, 7.17 mmol), N-ethyl-N-isopropylpropan-2-amine (1.872 mL, 10.75 mmol) and dichloromethane (40 mL) were combined in a 250 mL round-bottom flask to give a yellow solution. The mixture was stirred at room temperature overnight, and was subsequently diluted with DCM, washed with water and brine, dried over MgSO$_4$, and concentrated. The resulting residue was purified via flash column chromatography (120 g column), eluting with hexanes and EtOAc (1:0 to 10:1). The pure fractions were combined and concentrated to give crude title compound as a yellow solid (1.87 g, 75%).

Step B: (S)-5-Bromo-N2-((2,2-dimethyl-1,3-dioxolan-4-yl)methyl)-6-methylpyridine-2,3-diamine

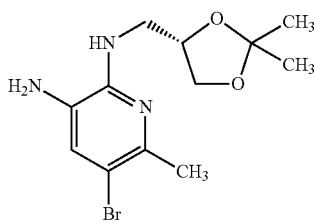

(S)-5-Bromo-N-((2,2-dimethyl-1,3-dioxolan-4-yl)methyl)-6-methyl-3-nitropyridin-2-amine (1.87 g, 5.40 mmol), ammonium chloride (0.578 g, 10.80 mmol), iron (0.905 g, 16.21 mmol), ethanol (20 mL) and water (10 mL) were combined in a 250 mL round-bottom flask to give a yellow suspension. The mixture was stirred at 90° C. for 2 hours. The solution was subsequently diluted with EtOAc and filtered. The filtrate was washed with water and brine, dried over MgSO$_4$, and concentrated to give crude title compound as a red-brown syrup (1.60 g, 94%).

Step C: (S)-6-Bromo-3-((2,2-dimethyl-1,3-dioxolan-4-yl)methyl)-5-methyl-1H-imidazo[4,5-b]pyridin-2(3H)-one (S)-5-Bromo-N2-((2,2-dimethyl-1,3-dioxolan-4-yl)methyl)-6-methylpyridine-2,3-diamine (0.800 g, 2.53 mmol), di(1H-imidazol-1-yl)methanone (0.615 g, 3.80 mmol) and THF (25 mL) were combined in a 250 mL round-bottom flask under nitrogen to give a brown solution. The mixture was stirred at room temperature overnight. The reaction mixture was subsequently treated with water and extracted into EtOAc. The organic layer was washed with water and brine, dried over MgSO$_4$, and concentrated to obtain a residue which was purified by flash column chromatography (40 g column) eluting with DCM and EtOAc (1:0 to 0:1). The pure fractions were combined and concentrated to give the title compound.

Preparation x9

5-Bromo-1-methyl-1H-pyrazole-3-carboxamide

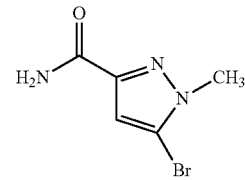

Step A:
5-Bromo-1-methyl-1H-pyrazole-3-carboxylic acid

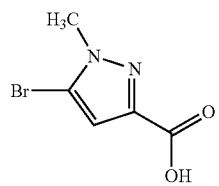

Lithium hydroxide (8.58 mL, 17.16 mmol) was added to a mixture of ethyl 5-bromo-1-methyl-1H-pyrazole-3-carboxylate (1 g, 4.29 mmol) in THF (10 mL) and water (2 mL). The reaction mixture was stirred for 5 hours at room temperature and was subsequently concentrated, acidified with concentrated HCl, and extracted into EtOAc. The organic layer was dried over Na$_2$SO$_4$ and concentrated to give the title compound as a white solid (0.72 g, 82%).

Step B:
5-Bromo-1-methyl-1H-pyrazole-3-carboxamide

To a mixture of 5-bromo-1-methyl-1H-pyrazole-3-carboxylic acid (0.1 g, 0.488 mmol) and DMF (3 mL) were added HOBt (0.092 g, 0.68 mmol) and EDC (0.140 g, 0.732 mmol). After stirring for 5 minutes, ammonium chloride (0.130 g, 2.439 mmol) was added, followed by N-ethyl-N-isopropylpropan-2-amine (0.255 mL, 1.463 mmol). The reaction mixture was stirred overnight at room temperature and was then diluted with EtOAc, washed with brine, dried over $Na_2SO_4$, and concentrated to obtain a residue which was purified by preparative HPLC. The pure fractions were combined and concentrated to give the title compound (0.036 g, 36%).

Preparation ×10

1-(5-Bromo-6-methylpyridin-2-yl)-4-methylpiperazine

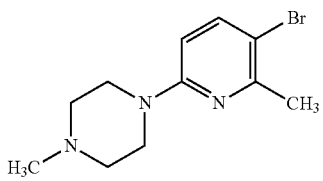

3-Bromo-6-fluoro-2-methylpyridine (500 mg, 2.63 mmol), 1-methylpiperazine (343 mg, 3.42 mmol), $Et_3N$ (1.100 mL, 7.89 mmol) and EtOH (3 mL) were mixed in a 4 mL vial equipped with a magnetic stir bar to give a colorless solution. The mixture was stirred for 18 hours at 70° C., after which 1-methylpiperazine (343 mg, 3.42 mmol) was added and heating was continued for 1 week. The reaction mixture was subsequently partitioned between water (30 mL) and EtOAc (40 mL). The layers were separated and the aqueous layer was back-extracted with EtOAc (40 mL). The combined organic layers were washed with brine (20 mL). The organic layer was dried over $Na_2SO_4$, filtered, and concentrated to yield a yellow syrup. The residue was purified via flash chromatography (12 g column), eluting with 0-80% EtOAc in heptanes. The pure fractions were combined and concentrated to give the title compound as a clear liquid (382 mg, 53.7%).

Preparation ×11

1-(4-Bromopyridin-2-yl)-4-methylpiperazine

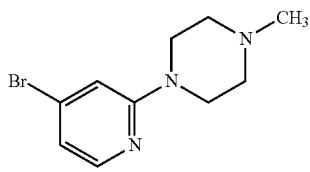

4-Bromo-2-chloropyridine (531 mg, 2.76 mmol), 1-methylpiperazine (691 mg, 6.90 mmol), $Et_3N$ (1.154 mL, 8.28 mmol) and EtOH (10 mL) were mixed in a 40 mL vial equipped with a magnetic stir bar to give a colorless solution. The mixture was stirred for 100 hours at 80° C. The reaction mixture was subsequently partitioned between water (30 mL) and EtOAc (40 mL). The layers were separated and the aqueous layer was back-extracted with EtOAc (40 mL). The combined organic layers were washed with brine (30 mL). The organic layer was dried over $Na_2SO_4$, filtered, and concentrated. The residue was purified via flash chromatography (12 g column), eluting with 0-80% EtOAc in heptanes. The pure fractions were combined and concentrated to give the title compound as a clear liquid (70 mg, 9.9%).

Preparation ×12

5-(7-Fluoro-1-(tetrahydro-2H-pyran-2-yl)pyrazolo[4,3-b]indol-4(1H)-yl)-4-methylpicolinic acid

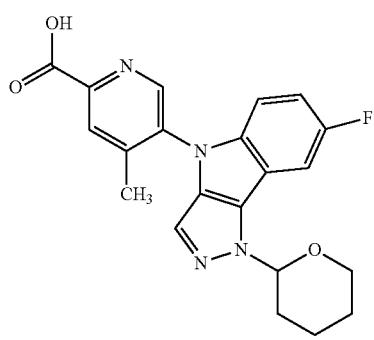 [SMILES: Cc1cc(C(=O)O)ncc1-n1c2ccc(F)cc2c2c1cnn2C1CCCCO1]

7-Fluoro-1-(tetrahydro-2H-pyran-2-yl)-1,4-dihydropyrazolo[4,3-b]indole (200 mg, 0.771 mmol), methyl 5-bromo-4-methylpicolinate (302 mg, 1.311 mmol), ((thiophene-2-carbonyl)oxy)copper (14.71 mg, 0.077 mmol), $Cs_2CO_3$ (754 mg, 2.314 mmol) and DMF (1.5 mL) were mixed in an 8 mL tube equipped with a magnetic stir bar to give a brown suspension. The solvent was purged with $N_2$, and the tube was sealed and heated for 48 hours at 180° C. in a sand bath. The reaction mixture was subsequently partitioned between water (30 mL) and EtOAc (30 mL). The layers were separated. The organic layer was discarded and the aqueous layer was acidified with 6N HCl. The aqueous layer was extracted with EtOAc (2×30 mL). The combined organic layers were concentrated to yield a dark syrup, which was triturated with water (10 mL). A yellow solid was filtered off, washed with water (20 mL) and dried to give the title compound, which was used without further purification (80 mg, 26%).

Preparation ×13

5-(7-Fluoro-1-(tetrahydro-2H-pyran-2-yl)pyrazolo[4,3-b]indol-4(1H)-yl)-6-methylpicolinic acid

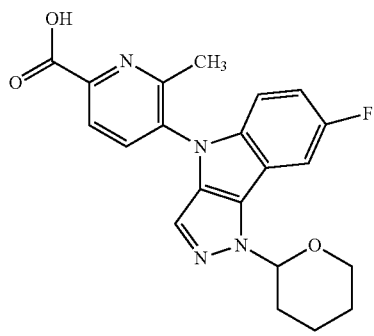 [SMILES: Cc1nc(C(=O)O)ccc1-n1c2ccc(F)cc2c2c1cnn2C1CCCCO1]

The title compound was prepared by a method similar to PREPARATION x12, using methyl 5-bromo-6-methylpicolinate in place of methyl 5-bromo-4-methylpicolinate.

Preparation x14

(R)-1-(5-Bromo-4-methylpyrimidin-2-yl)piperidin-3-ol

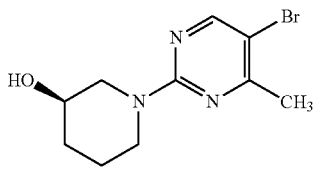

5-Bromo-2-chloro-4-methylpyrimidine (100 mg, 0.482 mmol), (R)-piperidin-3-ol hydrochloride (86 mg, 0.627 mmol), Et₃N (0.202 mL, 1.446 mmol) and DMF (2 mL) were mixed in an 8 mL tube equipped with a magnetic stir bar to give an orange solution. The tube was sealed and the mixture was heated in a microwave to 150° C. for 60 minutes. The reaction mixture was subsequently partitioned between water (20 mL) and EtOAc (20 mL). The layers were separated and the aqueous layer was back-extracted with EtOAc (20 mL). The combined organic layers were concentrated to give the title compound as a tan syrup, which was used without further purification.

Preparation x15

1-(5-Bromo-4-methylpyrimidin-2-yl)piperidin-4-ol

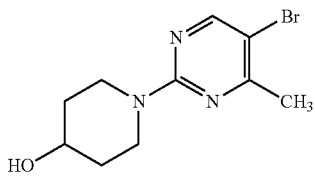

5-Bromo-2-chloro-4-methylpyrimidine (100 mg, 0.482 mmol), piperidin-4-ol (48.8 mg, 0.482 mmol), Et₃N (0.202 mL, 1.446 mmol) and EtOH (2 mL) were mixed in a 4 mL vial equipped with a magnetic stir bar to give an orange solution. The reaction mixture was stirred for 18 hours at 75° C. and was subsequently partitioned between water (20 mL) and EtOAc (20 mL). The layers were separated and the aqueous layer was back-extracted with EtOAc (20 mL). The combined organic layers were dried over Na₂SO₄, filtered, and concentrated to give crude title compound as a white solid (150 mg).

Preparation x16

(S)-5-Bromo-2-(3-fluoropyrrolidin-1-yl)-4-methylpyrimidine

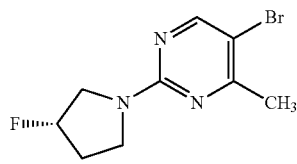

The title compound was prepared by a method similar to PREPARATION x15, using (S)-3-fluoropyrrolidine hydrochloride in place of piperidin-4-ol.

Preparation x17

(R)-1-(5-Bromo-4-methylpyrimidin-2-yl)-N,N-dimethylpyrrolidin-3-amine

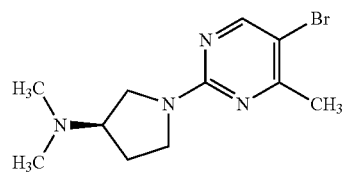

The title compound was prepared by a method similar to PREPARATION x15, using (R)—N,N-dimethylpyrrolidin-3-amine in place of piperidin-4-ol.

Preparation x18

(R)-5-Bromo-2-(3-fluoropyrrolidin-1-yl)-4-methylpyrimidine

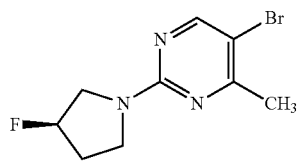

The title compound was prepared by a method similar to PREPARATION x15, using (R)-3-fluoropyrrolidine hydrochloride in place of piperidin-4-ol.

Preparation x19

(S)-1-(5-Bromo-4-methylpyrimidin-2-yl)piperidin-3-ol

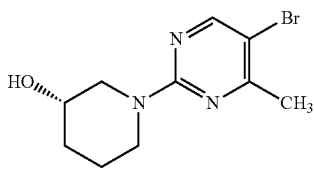

The title compound was prepared by a method similar to PREPARATION x15, using (S)-piperidin-3-ol hydrochloride in place of piperidin-4-ol.

Preparation x20

6-Bromo-3-ethyl-5-methyl-3H-imidazo[4,5-b]pyridine

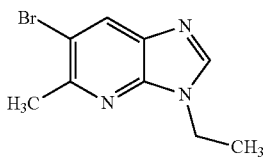

6-Bromo-5-methyl-3H-imidazo[4,5-b]pyridine (200 mg, 0.943 mmol), NaH (37.7 mg, 0.943 mmol) and DMF (3 mL) were mixed in a 20 mL vial equipped with a magnetic stir bar to give a brown suspension. After a few minutes ethyl iodide (0.076 mL, 0.943 mmol) was added and the reaction mixture was stirred overnight. The reaction mixture was subsequently partitioned between water (30 mL) and EtOAc (30 mL). The layers were separated and the aqueous layer was back-extracted with EtOAc (25 mL). The combined organic layers were concentrated to give a yellow syrup. The residue was purified via flash chromatography (4 g column) eluting with 0-70% EtOAc in heptanes. The pure fractions were combined and concentrated to give the title compound as a white solid (80 mg, 35%).

Preparation x21

6-Bromo-3-(2-methoxyethyl)-5-methyl-3H-imidazo[4,5-b]pyridine

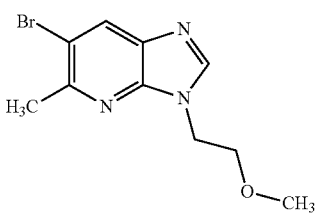

The title compound was prepared by a method similar to PREPARATION x20, using 1-bromo-2-methoxyethane in place of ethyl iodide.

Preparation x22

(S)-1-(5-Bromo-4-methylpyrimidin-2-yl)-N-methyl-pyrrolidine-2-carboxamide

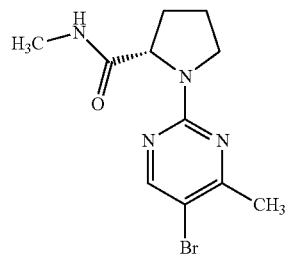

5-Bromo-2-chloro-4-methylpyrimidine (100 mg, 0.482 mmol), (S)—N-methylpyrrolidine-2-carboxamide hydrochloride (79 mg, 0.482 mmol), Et$_3$N (0.202 mL, 1.446 mmol) and DMF (2 mL) were mixed in an 8 mL tube equipped with a magnetic stir bar to give an orange solution. The tube was sealed and the mixture was heated to 70° C. for 72 hours. The reaction mixture was subsequently partitioned between water (20 mL) and EtOAc (20 mL), the layers separated, and the aqueous layer back-extracted with EtOAc (20 mL). The combined organic layers were dried over Na$_2$SO$_4$, filtered, and concentrated to give the title compound as a tan solid, which was used without further purification (140 mg, 97%).

Preparation x23

4-(5-Bromo-4-methylpyrimidin-2-yl)-1-methylpiperazin-2-one

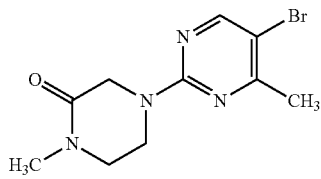 [SMILES: Cc1nc(N2CCN(C)C(=O)C2)ncc1Br]

The title compound was prepared by a method similar to PREPARATION x22, using 1-methylpiperazin-2-one hydrochloride in place of (S)—N-methylpyrrolidine-2-carboxamide hydrochloride.

Preparation x24

5-Bromo-2-(3,3-difluoroazetidin-1-yl)-4-methylpyrimidine

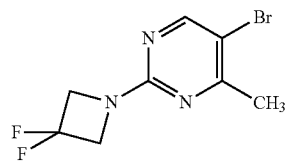

The title compound was prepared by a method similar to PREPARATION ×22, using 3,3-difluoroazetidine hydrochloride in place of (S)—N-methylpyrrolidine-2-carboxamide hydrochloride.

Preparation ×25

4-(5-Bromo-4-methylpyrimidin-2-yl)piperazin-2-one

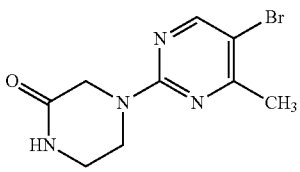

The title compound was prepared by a method similar to PREPARATION ×22, using piperazin-2-one in place of (S)—N-methylpyrrolidine-2-carboxamide hydrochloride.

Preparation ×26

(1-(5-Bromo-4-methylpyrimidin-2-yl)azetidin-3-yl)methanol

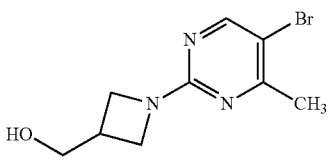

The title compound was prepared by a method similar to PREPARATION ×22, using azetidin-3-ylmethanol hydrochloride in place of (S)—N-methylpyrrolidine-2-carboxamide hydrochloride.

Preparation ×27

(R)-1-((5-Bromo-6-methylpyridin-2-yl)amino)propan-2-ol

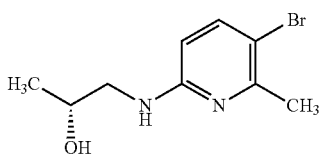

A mixture of 3-bromo-6-fluoro-2-methylpyridine (400 mg, 2.105 mmol), (R)-1-aminopropan-2-ol (237 mg, 3.16 mmol), and N-ethyl-N-isopropylpropan-2-amine (0.733 mL, 4.21 mmol) in DMSO (5 mL) was heated at 180° C. for 1 hour in a microwave. The reaction mixture was subsequently diluted with EtOAc, was washed with water and with brine, was dried over $Na_2SO_4$, and was concentrated to yield the title compound as brown oil, which was used without further purification (0.516 g, 100%).

Preparation ×28

(R)-1-(5-Bromo-4-methylpyrimidin-2-yl)pyrrolidine-3-carboxamide

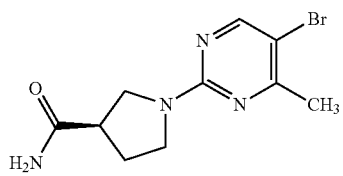 [SMILES: Cc1nc(N2CC[C@@H](C(N)=O)C2)ncc1Br]

A mixture of 5-bromo-2-chloro-4-methylpyrimidine (100 mg, 0.482 mmol), (R)-pyrrolidine-3-carboxamide, HCl (109 mg, 0.723 mmol) and N-ethyl-N-isopropylpropan-2-amine (0.252 mL, 1.446 mmol) in EtOH (3 mL) was stirred at 110° C. for 18 hours. The reaction mixture was subsequently diluted with EtOAc, washed with water and with brine, was dried over $MgSO_4$, and was concentrated to yield the title compound, which was used without further purification (0.137 g, 100%).

Preparation ×29

(S)-1-(5-Bromo-4-methylpyrimidin-2-yl)pyrrolidine-3-carboxamide

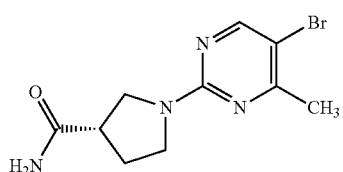

The title compound was prepared by a method similar to PREPARATION ×28, using (S)-pyrrolidine-3-carboxamide, HCl in place of (R)-pyrrolidine-3-carboxamide, HCl.

Preparation ×30

(S)-1-(5-Bromo-4-methylpyrimidin-2-yl)pyrrolidine-2-carboxamide

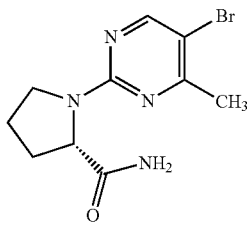 [SMILES: Cc1nc(N2CCC[C@H]2C(N)=O)ncc1Br]

The title compound was prepared by a method similar to PREPARATION ×28, using (S)-pyrrolidine-2-carboxamide in place of (R)-pyrrolidine-3-carboxamide, HCl.

Preparation ×31

(R)-1-(5-Bromo-4-methylpyrimidin-2-yl)pyrrolidine-2-carboxamide

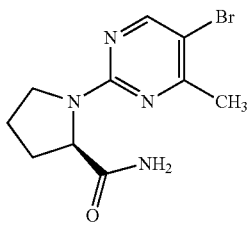 [SMILES: Cc1nc(N2CCC[C@@H]2C(N)=O)ncc1Br]

The title compound was prepared by a method similar to PREPARATION ×28, using (R)-pyrrolidine-2-carboxamide in place of (R)-pyrrolidine-3-carboxamide, HCl.

Preparation ×32

2-((5-Bromo-4-methylpyrimidin-2-yl)amino)ethanol

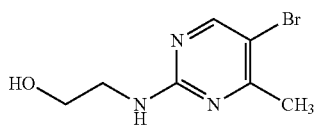

The title compound was prepared by a method similar to PREPARATION ×28, using 2-aminoethanol in place of (R)-pyrrolidine-3-carboxamide, HCl.

Preparation ×33

(R)-2-((5-bromo-4-methylpyrimidin-2-yl)amino)propan-1-ol

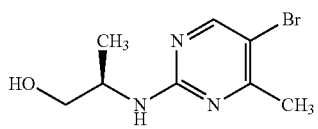

The title compound was prepared by a method similar to PREPARATION ×28, using (R)-2-aminopropan-1-ol in place of (R)-pyrrolidine-3-carboxamide, HCl.

Preparation ×34

(3R,4R)-1-(5-Bromo-4-methylpyrimidin-2-yl)pyrrolidine-3,4-diol

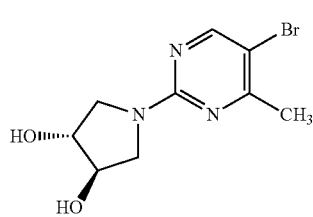

The title compound was prepared by a method similar to PREPARATION ×28, using (3R,4R)-pyrrolidine-3,4-diol, HCl in place of (R)-pyrrolidine-3-carboxamide, HCl.

Preparation ×35

(R)-(4-(5-Bromo-4-methylpyrimidin-2-yl)morpholin-2-yl)methanol

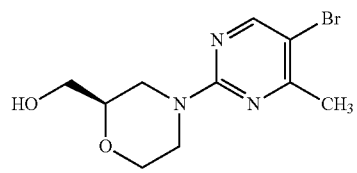 [SMILES: Cc1nc(N2CCO[C@@H](CO)C2)ncc1Br]

The title compound was prepared by a method similar to PREPARATION ×28, using (R)-morpholin-2-ylmethanol, HCl in place of (R)-pyrrolidine-3-carboxamide, HCl.

Preparation ×36

(R)-1-(5-Bromo-4-methoxypyrimidin-2-yl)pyrrolidin-3-ol

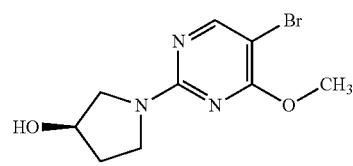

The title compound was prepared by a method similar to PREPARATION ×28, using (R)-pyrrolidin-3-ol in place of (R)-pyrrolidine-3-carboxamide, HCl, and 5-bromo-2-chloro-4-methoxypyrimidine in place of 5-bromo-2-chloro-4-methylpyrimidine.

Preparation ×37

(S)-(4-(5-Bromo-4-methylpyrimidin-2-yl)morpholin-2-yl)methanol

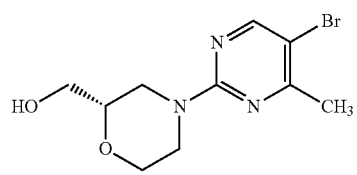 [SMILES: Cc1nc(N2CCO[C@H](CO)C2)ncc1Br]

The title compound was prepared by a method similar to PREPARATION ×28, using (S)-morpholin-2-ylmethanol in place of (R)-pyrrolidine-3-carboxamide, HCl.

Preparation x38

(S)-2-((5-Bromo-4-methylpyrimidin-2-yl)amino)propan-1-ol

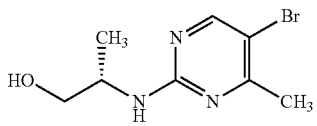

The title compound was prepared by a method similar to PREPARATION x28, using (S)-2-aminopropan-1-ol in place of (R)-pyrrolidine-3-carboxamide, HCl.

Preparation x39

(S)-1-((5-Bromo-4-methylpyrimidin-2-yl)amino)propan-2-ol

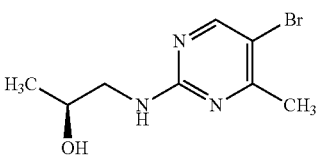

The title compound was prepared by a method similar to PREPARATION x28, using (S)-1-aminopropan-2-ol in place of (R)-pyrrolidine-3-carboxamide, HCl.

Preparation x40

(R)-1-((5-Bromo-4-methylpyrimidin-2-yl)amino)propan-2-ol

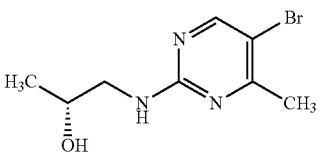

The title compound was prepared by a method similar to PREPARATION x28, using (R)-1-aminopropan-2-ol in place of (R)-pyrrolidine-3-carboxamide, HCl.

Preparation x41

1-(5-Bromo-4-methylpyrimidin-2-yl)azetidin-3-ol

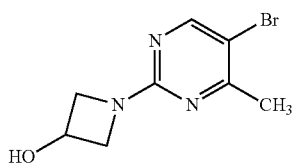

The title compound was prepared by a method similar to PREPARATION x28, using azetidin-3-ol hydrochloride in place of (R)-pyrrolidine-3-carboxamide, HCl.

Preparation x42

5-Bromo-N-(2-hydroxyethyl)-1-methyl-1H-pyrazole-3-carboxamide

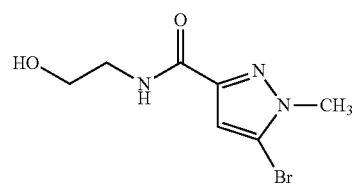

To a mixture of 5-bromo-1-methyl-1H-pyrazole-3-carboxylic acid (0.1 g, 0.488 mmol) in DMF (3 mL) were added HOBt (0.092 g, 0.683 mmol) and EDC (0.140 g, 0.732 mmol). The mixture was stirred for 5 minutes. 2-Aminoethanol (0.130 g, 2.439 mmol), followed by N-ethyl-N-isopropylpropan-2-amine (0.255 mL, 1.463 mmol), were then added. The reaction mixture was stirred for 18 hours. The crude reaction mixture was diluted with EtOAc, washed with brine, dried over $Na_2SO_4$, and concentrated. The crude residue was purified by preparative LC/MS, eluting with 15-30% ACN in water (containing 0.05% TFA). The product-containing fractions were combined and concentrated to give the title compound (0.036 g, 36%).

Preparation x43

1-(5-Bromo-4-methylpyrimidin-2-yl)piperidin-4-ol

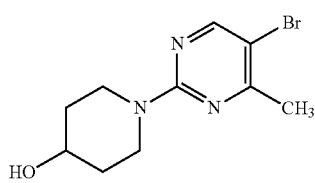

A mixture of 5-bromo-2-chloro-4-methylpyrimidine (100 mg, 0.482 mmol), piperidin-4-ol (58.5 mg, 0.578 mmol), and N-ethyl-N-isopropylpropan-2-amine (0.252 mL, 1.446 mmol) in EtOH (6 mL) was heated at 75° C. overnight. The mixture was subsequently diluted with EtOAc, washed with water and brine, dried over $Na_2SO_4$, and concentrated to give the title compound as a brown oil, which was used without further purification (131 mg, 100%).

Preparation ×44

1-(5-Bromo-4-methylpyrimidin-2-yl)azetidine-3-carboxamide

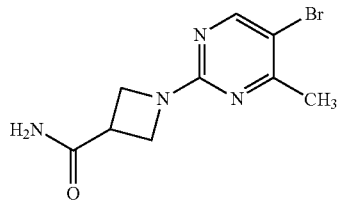

The title compound was prepared by a method similar to PREPARATION ×43, using azetidine-3-carboxamide in place of piperidin-4-ol.

Preparation ×45

(S)-5-Bromo-N²-((2,2-dimethyl-1,3-dioxolan-4-yl)methyl)-6-methylpyridine-2,3-diamine

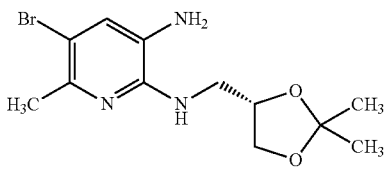 [SMILES: Cc1nc(NC[C@H]2COC(C)(C)O2)c(N)cc1Br]

Step A: (S)-5-Bromo-N-((2,2-dimethyl-1,3-dioxolan-4-yl)methyl)-6-methyl-3-nitropyridin-2-amine

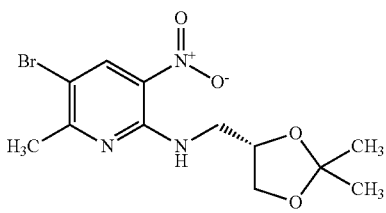 [SMILES: Cc1nc(NC[C@H]2COC(C)(C)O2)c([N+](=O)[O-])cc1Br]

A mixture of 2,5-dibromo-6-methyl-3-nitropyridine (2.121 g, 7.17 mmol), (S)-(2,2-dimethyl-1,3-dioxolan-4-yl)methanamine (0.94 g, 7.17 mmol), N-ethyl-N-isopropylpropan-2-amine (1.872 mL, 10.75 mmol) and DCM (40 mL) was stirred at room temperature overnight. The mixture was subsequently diluted with DCM, washed with water and brine, dried over MgSO₄, and concentrated. The residue was purified by flash chromatography (120 g column) eluting with EtOAc in hexanes (0:1 to 1:10). The pure fractions were combined and concentrated to give the title compound as a yellow solid (1.87 g, 75%).

Step B: (S)-5-Bromo-N2-((2,2-dimethyl-1,3-dioxolan-4-yl)methyl)-6-methylpyridine-2,3-diamine (S)-5-Bromo-N-((2,2-dimethyl-1,3-dioxolan-4-yl)methyl)-6-methyl-3-nitropyridin-2-amine (1.87 g, 5.40 mmol), ammonium chloride (0.578 g, 10.80 mmol), and iron (0.905 g, 16.21 mmol) in EtOH (20 mL) and water (10 mL) were stirred at 90° C. for 1 hour. The mixture was subsequently diluted with EtOAc and filtered. The filtrate was washed with water and brine, dried over MgSO₄, and concentrated to give the title compound as a red brown syrup, which was used without further purification (1.60 g, 94%).

Preparation ×46

(S)-6-Bromo-3-((2,2-dimethyl-1,3-dioxolan-4-yl)methyl)-5-methyl-3H-imidazo[4,5-b]pyridine

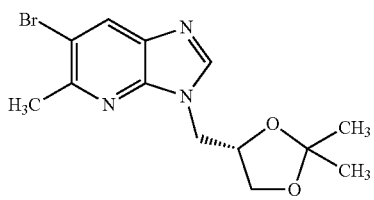 [SMILES: Cc1nc2c(cc1Br)ncn2C[C@H]1COC(C)(C)O1]

(S)-5-Bromo-N²-((2,2-dimethyl-1,3-dioxolan-4-yl)methyl)-6-methylpyridine-2,3-diamine (800 mg, 2.53 mmol) and triethoxymethane (4.0 mL, 24.29 mmol) in acetic anhydride (4.7 mL, 50.6 mmol) was heated at 100° C. for 15 hours. The mixture was subsequently concentrated. The residue was treated with water and extracted with EtOAc. The extract was washed with saturated NaHCO₃ and brine, dried over MgSO₄, and concentrated to give the title compound as a red brown film, which was used without further purification (721 mg, 87%).

Preparation ×47

(R)-5-Bromo-N²-((2,2-dimethyl-1,3-dioxolan-4-yl)methyl)-6-methylpyridine-2,3-diamine

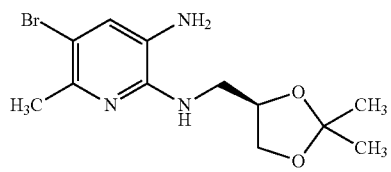 [SMILES: Cc1nc(NC[C@@H]2COC(C)(C)O2)c(N)cc1Br]

The title compound was prepared by a method similar to PREPARATION ×45, using (R)-(2,2-dimethyl-1,3-dioxolan-4-yl)methanamine in place of (S)-(2,2-dimethyl-1,3-dioxolan-4-yl)methanamine.

Preparation ×48

(R)-6-Bromo-3-((2,2-dimethyl-1,3-dioxolan-4-yl)methyl)-5-methyl-3H-imidazo[4,5-b]pyridine

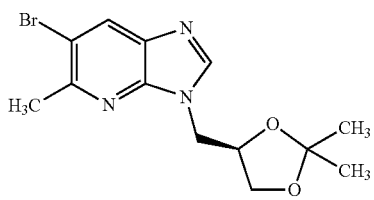 [SMILES: Cc1nc2c(cc1Br)ncn2C[C@@H]1COC(C)(C)O1]

The title compound was prepared by a method similar to PREPARATION ×46, using (R)-5-bromo-N²-((2,2-dimethyl-1,3-dioxolan-4-yl)methyl)-6-methylpyridine-2,3-diamine in place of (S)-5-bromo-N²-((2,2-dimethyl-1,3-dioxolan-4-yl)methyl)-6-methylpyridine-2,3-diamine.

Preparation ×49

Methyl 3-((3-amino-5-bromo-6-methylpyridin-2-yl)amino)propanoate

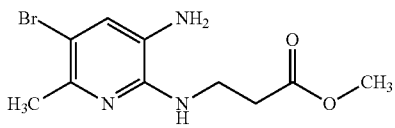 [SMILES: COC(=O)CCNc1nc(C)c(Br)cc1N]

The title compound was prepared by a method similar to PREPARATION ×45, using methyl 3-aminopropanoate, HCl in place of (S)-(2,2-dimethyl-1,3-dioxolan-4-yl)methanamine.

Preparation ×50

6-Bromo-3-(3-hydroxypropyl)-5-methyl-1H-imidazo[4,5-b]pyridin-2(3H)-one

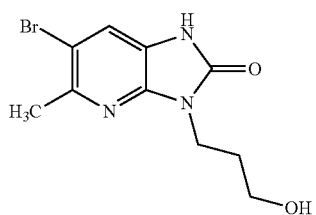 [SMILES: Cc1nc2c(cc1Br)[nH]c(=O)n2CCCO]

Step A: Methyl 3-(6-bromo-5-methyl-2-oxo-1H-imidazo[4,5-b]pyridine-3(2H)-yl)propanoate

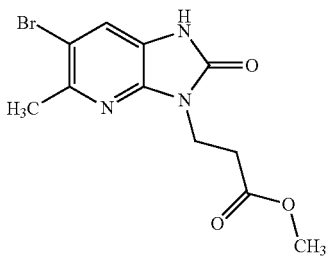 [SMILES: COC(=O)CCn1c(=O)[nH]c2cc(Br)c(C)nc21]

A mixture of methyl 3-((3-amino-5-bromo-6-methylpyridin-2-yl)amino)propanoate (0.966 g, 3.35 mmol) and di(1H-imidazol-1-yl)methanone (0.815 g, 5.03 mmol) in THF (20 mL) was stirred at room temperature under nitrogen for 5 hours. The mixture was subsequently treated with water and extracted with EtOAc. The extract was dried over MgSO₄ and concentrated to give the title compound as a brown solid which was used without further purification (1.185 g, 100%).

Step B: 6-Bromo-3-(3-hydroxypropyl)-5-methyl-1H-imidazo[4,5-b]pyridin-2(3H)-one

Sodium tetrahydroborate (632 mg, 16.70 mmol) and methyl 3-(6-bromo-5-methyl-2-oxo-1H-imidazo[4,5-b]pyridine-3(2H)-yl)propanoate (525 mg, 1.67 mmol) in THF (15 mL) were stirred at 50° C. A solution of methanol (4 mL) and THF (5.3 mL) was added dropwise and the reaction mixture was stirred at the same temperature for 1 hour. After cooling down, saturated NH₄Cl was added dropwise at 0° C. The mixture was extracted with EtOAc. The extract was washed with brine, dried over MgSO₄, and concentrated to give the title compound as a yellow solid, which was used without further purification (580 mg, 100%).

Preparation ×51

Ethyl 2-((3-amino-5-bromo-6-methylpyridin-2-yl)amino)acetate

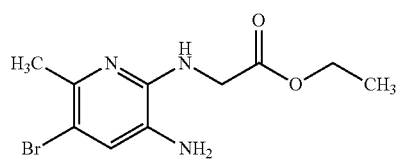 [SMILES: CCOC(=O)CNc1nc(C)c(Br)cc1N]

The title compound was prepared by a method similar to PREPARATION ×45, using 3-bromo-6-chloro-2-methyl-5-nitropyridine and methyl 3-aminopropanoate, HCl in place of 2,5-dibromo-6-methyl-3-nitropyridine and (S)-(2,2-dimethyl-1,3-dioxolan-4-yl)methanamine.

Preparation ×52

2-(6-Bromo-5-methyl-3H-imidazo[4,5-b]pyridin-3-yl)ethanol

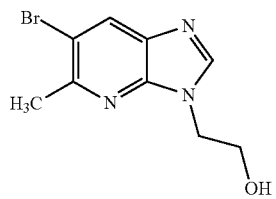

Step A: Ethyl 2-(6-bromo-5-methyl-3H-imidazo[4,5-b]pyridin-3-yl)acetate

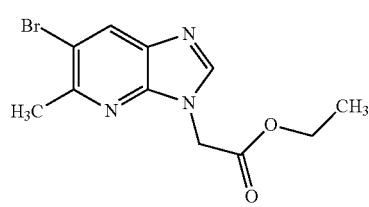 [SMILES: CCOC(=O)Cn1cnc2cc(Br)c(C)nc21]

To a 250 mL round-bottom flask were added ethyl 2-((3-amino-5-bromo-6-methylpyridin-2-yl)amino)acetate (420 mg, 1.458 mmol) and triethoxymethane (2.327 mL, 13.99 mmol) in DMA (3 mL) to give a brown solution. The mixture was heated at 100° C. under nitrogen for 9 days. The mixture was subsequently treated with water and extracted with EtOAc. The extract was washed with water, dried over MgSO₄, and concentrated to give crude title compound.

Step B: 2-(6-Bromo-5-methyl-3H-imidazo[4,5-b]pyridin-3-yl)ethanol

To a 250 mL round-bottom flask was added sodium tetrahydroborate (632 mg, 16.70 mmol) and methyl 3-(6-bromo-5-methyl-2-oxo-1H-imidazo[4,5-b]pyridin-3(2H)-yl)propanoate (525 mg, 1.67 mmol) in THF (15 mL) to give a yellow suspension. The mixture was stirred at 50° C. A solution of methanol (2 mL) and THF (2.6 mL) was added dropwise and the mixture was stirred at the same temperature for 1 hour. After cooling down, saturated NH₄Cl was added dropwise at 0° C. The mixture was subsequently extracted with EtOAc. The extract was washed with brine, dried over MgSO₄, and concentrated to give crude title compound as a yellow solid.

Preparation ×53

(R)-5-Bromo-N-((2,2-dimethyl-1,3-dioxolan-4-yl)methyl)-4-methylpyrimidin-2-amine

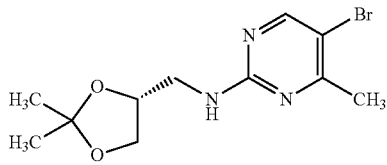

The title compound was prepared by a method similar to PREPARATION ×43, using (R)-2,2-dimethyl-1,3-dioxolan-4-yl)methanamine in place of piperidin-4-ol.

Preparation ×54

Ethyl 2-((3-amino-5-bromo-6-methylpyridin-2-yl)amino)acetate

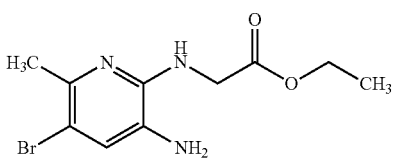 [SMILES: CCOC(=O)CNc1nc(C)c(Br)cc1N]

The title compound was prepared by a method similar to PREPARATION ×45, using ethyl 2-aminoacetate hydrochloride in place of (S)-(2,2-dimethyl-1,3-dioxolan-4-yl)methanamine.

Preparation ×55

6-Bromo-3-(2-hydroxyethyl)-5-methyl-1H-imidazo[4,5-b]pyridin-2(3H)-one

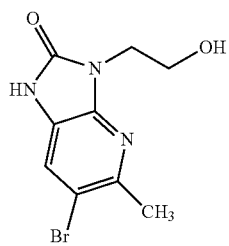

The title compound was prepared by a method similar to PREPARATION ×50, using ethyl 2-((3-amino-5-bromo-6-methylpyridin-2-yl)amino)acetate in place of methyl 3-((3-amino-5-bromo-6-methylpyridin-2-yl)amino)propanoate.

Example 1

4-Benzyl-7-fluoro-1,4-dihydropyrazolo[4,3-b]indole

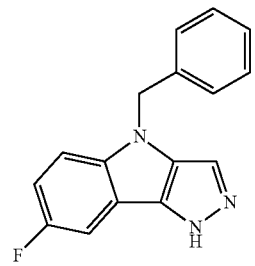 [SMILES: Fc1ccc2c(c1)c1[nH]ncc1n2Cc1ccccc1]

Step A: 1-Azido-2-bromo-4-fluorobenzene

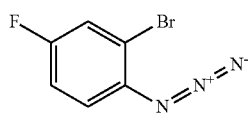

To a 500 mL round-bottom flask were added 2-bromo-4-fluoroaniline (10.0 g, 52.63 mmol, 1.0 eq), concentrated HCl (9.2 mL) and water (110 mL). The mixture was stirred at 0° C. for 20 minutes. A solution of NaNO₂ (3.63 g, 1.0 eq) in water (25 mL) was added dropwise while maintaining the temperature below 5° C. Following the addition, the mixture was stirred at this temperature for 20 minutes. A solution of NaN₃ (3.42 g, 1.0 eq) in water (35 mL) was added dropwise while maintaining the internal temperature of the reaction mixture below 5° C. The reaction was stirred at 0° C. for 30 minutes and then at room temperature for 3 hours. The reaction mixture was subsequently extracted into EtOAc and the organic layer was separated, dried over Na₂SO₄, filtered, and concentrated to give the title compound (10.0 g, 88%). ¹H NMR (300 MHz, CDCl₃) δ ppm 7.32-7.29 (m, 1H), 7.15-7.05 (m, 2H).

Step B: 5-(2-Azido-5-fluorophenyl)-1-(tetrahydro-2H-pyran-2-yl)-1H-pyrazole

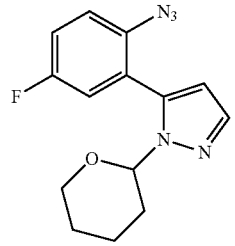 [SMILES: [N-]=[N+]=Nc1ccc(F)cc1-c1ccnn1C1CCCCO1]

To a three-neck flask were added 1-azido-2-bromo-4-fluorobenzene (1 g, 4.63 mmol, 1.0 eq), 1-(tetrahydro-2H-pyran-2-yl)-5-(4,4,5,5-tetramethyl-1,3,2-dioxaborolan-2-yl)-1H-pyrazole (1.54 g, 1.2 eq), (Ph$_3$P)$_4$Pd (0.27 g, 0.05 eq), Na$_2$CO$_3$ (1.17 g, 2.4 eq), DME (20 mL), and water (1.0 mL). The reaction mixture was refluxed overnight and was subsequently cooled to room temperature, concentrated, and partitioned between water and EtOAc. The layers were separated and the organic layer was washed with brine, dried over Na$_2$SO$_4$, filtered, and concentrated. The resulting oil was purified by flash chromatography, eluting with EtOAc/petroleum ether (1:10) to give the title compound (0.8 g, 60.6%). $^1$H NMR (300 MHz, CDCl$_3$) δ ppm 7.80-7.76 (m, 1H), 7.64 (s, 1H), 7.56-7.52 (m, 1H), 7.48-7.43 (m, 1H), 7.26-7.15 (m, 1H), 6.35 (d, 1H), 5.04-5.5.01 (m, 1H), 4.02-4.02 (m, 1H), 3.51-3.44 (m, 1H), 2.54-2.50 (m, 1H), 1.66-1.51 (m, 4H).

Step C: 7-Fluoro-1-(tetrahydro-2H-pyran-2-yl)-1,4-dihydropyrazolo[4,3-b]indole

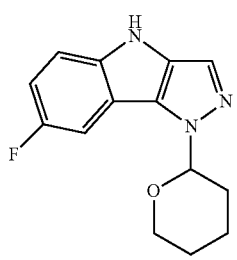 [SMILES: Fc1ccc2[nH]c3cnn(C4CCCCO4)c3c2c1]

A solution of 5-(2-azido-5-fluorophenyl)-1-(tetrahydro-2H-pyran-2-yl)-1H-pyrazole in 1,2-dichlorobenzene was heated to 170° C. for 2 hours. The reaction mixture was cooled to room temperature and concentrated to an oil. The residue was purified by flash chromatography, eluting with EtOAc/petroleum ether (1:5) to give the title compound (0.26 g, 36%). $^1$H NMR (300 MHz, DMSO-d$_6$) δ ppm 10.71 (s, 1H), 7.60-7.54 (m, 2H), 7.43-7.40 (m, 1H), 7.15-7.10 (m, 1H), 5.76-5.74 (d, 1H, J=8.4 Hz), 3.98-3.95 (m, 1H), 3.84-3.78 (m, 1H), 2.21-2.16 (m, 1H), 2.00-1.97 (m, 2H), 1.79-1.76 (m, 1H), 1.63 (m, 2H).

Step D: 4-Benzyl-7-fluoro-1-(tetrahydro-2H-pyran-2-yl)-1,4-dihydropyrazolo[4,3-b]indole

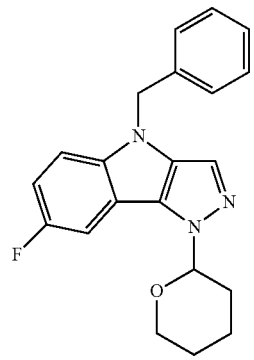 [SMILES: Fc1ccc2c(c1)c1c(cnn1C1CCCCO1)n2Cc1ccccc1]

To a solution of 7-fluoro-1-(tetrahydro-2H-pyran-2-yl)-1,4-dihydropyrazolo[4,3-b]indole (100 mg, 0.39 mmol, 1 eq) in ethanol was added KOH (21 mg, 1 eq) at room temperature. The mixture was stirred for 5 minutes and then concentrated. Acetone (5 mL) and (bromomethyl)benzene (66 mg, 1 eq) were added. The mixture was stirred for another 5 minutes at room temperature, filtered, and concentrated to give the title compound (130 mg, 97%).

Step E: 4-Benzyl-7-fluoro-1,4-dihydropyrazolo[4,3-b]indole

To a solution of 4-benzyl-7-fluoro-1-(tetrahydro-2H-pyran-2-yl)-1,4-dihydropyrazolo[4,3-b]indole (130 mg, 0.37 mmol, 1 eq) in ethanol was added concentrated HCl (1 mL). The reaction mixture was stirred overnight at room temperature, concentrated, and its pH adjusted to 8 with saturated aq NaHCO$_3$. The reaction mixture was extracted with EtOAc (2×20 mL) and washed with brine. The organic layer was dried over Na$_2$SO$_4$, filtered and concentrated. The resulting oil was purified by preparative HPLC to give the title compound (16 mg, 16%). $^1$H NMR (400 MHz, CDCl$_3$) δ ppm 10.88 (s, 1H), 7.55-7.53 (m, 1H), 7.33-7.290 (m, 3H), 7.25-7.21 (m, 3H), 7.12-7.06 (m, 2H), 5.26 (s, 2H). MS [M+H]$^+$ calc'd for C$_{16}$H$_{12}$FN$_3$, 266.11; found 266.1.

Example 2

4-Benzyl-6,7-difluoro-1,4-dihydropyrazolo[4,3-b]indole

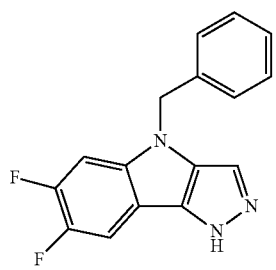 [SMILES: Fc1cc2c3[nH]ncc3n(Cc3ccccc3)c2cc1F]

The title compound was prepared by a method similar to EXAMPLE 1, using 2-bromo-4,5-difluoroaniline in place of 2-bromo-4-fluoroaniline. $^1$H NMR (300 MHz, CDCl$_3$) δ ppm 7.72-7.66 (m, 1H), 7.34-7.30 (m, 3H), 7.24-7.22 (m, 2H), 7.12-7.06 (m, 2H), 5.23 (s, 2H). MS [M+H]+ calc'd for C$_{16}$H$_{11}$F$_2$N$_3$, 284.10; found 284.

Example 3

7-Fluoro-4-(pyridin-3-yl)-1,4-dihydropyrazolo[4,3-b]indole

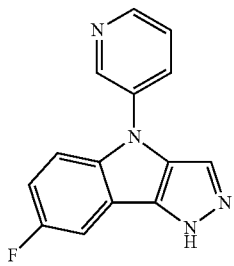 [SMILES: Fc1ccc2c(c1)c1[nH]ncc1n2-c1cccnc1]

Step A: 7-Fluoro-4-(pyridin-3-yl)-1-(tetrahydro-2H-pyran-2-yl)-1,4-dihydropyrazolo[4,3-b]indole

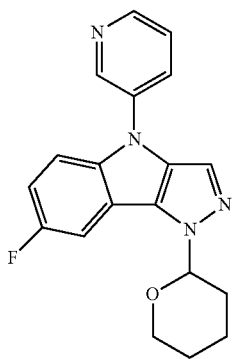 [SMILES: Fc1ccc2c(c1)c1c(cnn1C1CCCCO1)n2-c1cccnc1]

To a tube under a nitrogen blanket were added Pd$_2$(dba)$_3$ (19 mg, 0.020 mmol), tri-tert-butyl phosphine (250 mg, 10% wt, 0.12 mmol), and xylene (2 mL). The catalyst mixture was stirred at 60° C. for 20 minutes. To a separate tube under a nitrogen blanket were added 7-fluoro-1-(tetrahydro-2H-pyran-2-yl)-1,4-dihydropyrazolo[4,3-b]indole (48 mg, 0.19 mmol), 3-bromo pyridine (30 mg, 0.19 mmol), K$_2$CO$_3$ (27 mg, 0.19 mmol), and 18-crown-6 (16 mg, 0.06 mmol). The catalyst was added and the reaction mixture was stirred at 120° C. for 5 hours under nitrogen. The reaction mixture was cooled to room temperature, concentrated, and purified by silica gel column chromatography, eluting with petroleum ether/EtOAc (4:1) to give the title compound as an oil (60 mg, 95%). $^1$H NMR (300 MHz, CDCl$_3$) δ ppm 1.58-1.86 (5H, m), 2.33-2.37 (1H, m), 3.69-3.91 (1H, m), 4.11-4.17 (1H, m), 5.75-5.79 (1H, m), 7.08-7.15 (1H, m), 7.46-7.59 (3H, m), 7.66-7.70 (1H, m), 7.92 (1H, d, J=8.1 Hz), 8.59 (1H, d, J=3.9 Hz), 8.95 (1H, d, J=1.8 Hz).

Step B: 7-Fluoro-4-(pyridin-3-yl)-1,4-dihydropyrazolo[4,3-b]indole

To a solution of 7-fluoro-4-(pyridin-3-yl)-1-(tetrahydro-2H-pyran-2-yl)-1,4-dihydropyrazolo[4,3-b]indole (60 mg, 0.17 mmol) in ethanol (10 mL) was added concentrated HCl (1 mL) and the reaction mixture was stirred at room temperature for 1.5 hours. The reaction mixture was concentrated and its pH adjusted to 8 with saturated aq NaHCO$_3$. The residue was extracted with EtOAc (2×20 mL) and washed with brine. The organic layer was dried over Na$_2$SO$_4$, filtered, and concentrated to give an oil, which was purified by preparative TLC to obtain the title compound. $^1$H NMR (400 MHz, CD$_3$OD) δ ppm 7.06-7.11 (1H, m), 7.51-7.60 (3H, m), 7.71 (1H, s), 8.04-8.07 (1H, m), 8.39-8.40 (1H, m), 8.81 (1H, d, J=2.4 Hz). [M+H]+ calc'd for C$_{14}$H$_9$FN$_4$, 253.09; found, 253.1.

Example 4

6,7-Difluoro-4-(pyridin-3-yl)-1,4-dihydropyrazolo[4,3-b]indole

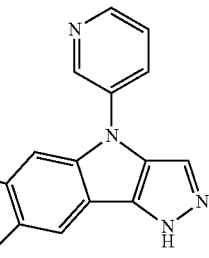

The title compound was prepared by a method similar to EXAMPLE 3, using 6,7-difluoro-1-(tetrahydro-2H-pyran-2-yl)-1,4-dihydropyrazolo[4,3-b]indole in place of 7-fluoro-1-(tetrahydro-2H-pyran-2-yl)-1,4-dihydropyrazolo[4,3-b]indole. 1H NMR (400 MHz, CD$_3$OD) δ ppm 7.65-7.73 (2H, m), 7.82 (1H, s), 7.89-7.92 (1H, m), 8.50-8.52 (1H, m), 8.56 (1H, d, J=3.6 Hz), 9.05 (1H, s). MS [M+H]+ calc'd for C$_{14}$H$_8$F$_2$N$_4$, 271.08; found 271.0.

Example 5

7-Fluoro-4-(5-methyl-3H-imidazo[4,5-b]pyridin-6-yl)-1,4-dihydropyrazolo[4,3-b]indole

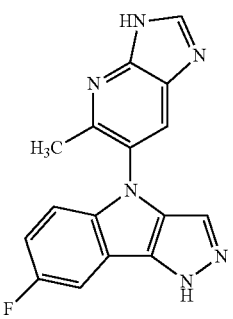 [SMILES: Cc1nc2[nH]cnc2cc1-n1c2ccc(F)cc2c2[nH]ncc21]

Step A: 7-Fluoro-4-(5-methyl-3H-imidazo[4,5-b]pyridin-6-yl)-1-(tetrahydro-2H-pyran-2-yl)-1,4-dihydropyrazolo[4,3-b]indole

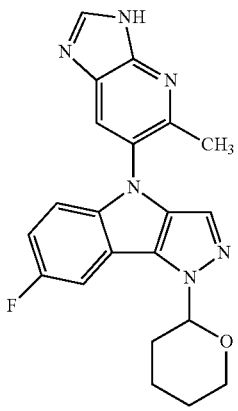 [SMILES: Cc1nc2[nH]cnc2cc1-n1c2ccc(F)cc2c2c1cnn2C1CCCCO1]

7-Fluoro-1-(tetrahydro-2H-pyran-2-yl)-1,4-dihydropyrazolo[4,3-b]indole (200 mg, 0.771 mmol), 6-bromo-5-methyl-3H-imidazo[4,5-b]pyridine (278 mg, 1.311 mmol), copper(I) thiophene-2-carboxylate (14.7 mg, 0.771 mmol), Cs$_2$CO$_3$ (754 mg, 2.314 mmol) and DMF (3 mL) were mixed in an 8 mL tube equipped with a magnetic stir bar to give a brown suspension. The solvent was purged with nitrogen and the tube was sealed. The reaction mixture was heated in a sand bath for 2 days at 180° C., then cooled and partitioned between water (25 mL) and EtOAc (50 mL). The layers were separated and the organic layer was washed with brine (20 mL). The organic layer was dried over Na$_2$SO$_4$, filtered, and concentrated. The resulting yellow syrup was purified via flash chromatography (12 g column) eluting with 0-100% EtOAc in heptanes, followed by 0-15% MeOH in DCM. The pure fractions were combined and concentrated to give the title compound as a yellow syrup (250 mg).

Step B: 7-Fluoro-4-(5-methyl-3H-imidazo[4,5-b]pyridin-6-yl)-1,4-dihydropyrazolo[4,3-b]indole 7-Fluoro-4-(5-methyl-3H-imidazo[4,5-b]pyridin-6-yl)-1-(tetrahydro-2H-pyran-2-yl)-1,4-dihydropyrazolo[4,3-b]indole (250 mg, 0.64 mmol) was dissolved in MeOH (5 mL), treated with concentrated HCl (4 drops) and stirred overnight. The product was purified by preparative HPLC, eluting with 15-40% ACN in H$_2$O (containing 0.05% TFA). The pure fractions were lyophilized to give a bis-TFA salt of the title compound as a yellow solid (150.8 mg, 36.6%). $^1$H NMR (400 MHz, DMSO-d$_6$) δ ppm 2.28 (s, 3 H), 7.05 (dd, J=8.97, 4.42 Hz, 1 H), 7.15 (td, J=9.16, 2.65 Hz, 1 H), 7.60 (s, 1 H), 7.69 (dd, J=8.97, 2.65 Hz, 1 H), 8.32 (s, 1 H), 9.06 (br s, 1 H). MS [M+H]$^+$ calc'd for C$_{16}$H$_{11}$FN$_6$, 307.11; found 307.2.

Example 6

(3R)-1-(5-(7-Fluoropyrazolo[4,3-b]indol-4(1H)-yl)-6-methylpyridin-2-yl)pyrrolidin-3-ol

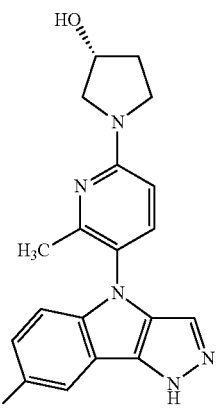

A TFA salt of the title compound was prepared by a method similar to EXAMPLE 5, using (R)-1-(5-bromo-6-methylpyridin-2-yl)pyrrolidin-3-ol in place of 6-bromo-5-methyl-3H-imidazo[4,5-b]pyridine. 1H NMR (400 MHz, DMSO-d$_6$) δ ppm 2.00 (br s, 1 H), 2.05-2.12 (m, 2 H), 2.16 (s, 3 H), 3.48 (d, J=11.12 Hz, 1 H), 3.65 (d, J=7.07 Hz, 4 H), 4.48 (br s, 2 H), 6.80 (br s, 1 H), 7.05 (dd, J=8.59, 4.55 Hz, 1 H), 7.13-7.19 (m, 1 H), 7.56 (d, J=1.26 Hz, 1 H), 7.62-7.67 (m, 1 H), 7.78 (br s, 1 H). MS [M+H]$^+$ calc'd for C$_{19}$H$_{18}$FN$_5$O, 352.16; found 352.3.

Example 7

7-Fluoro-4-(2-methyl-6-(4-methylpiperazin-1-yl)pyridin-3-yl)-1,4-dihydropyrazolo[4,3-b]indole

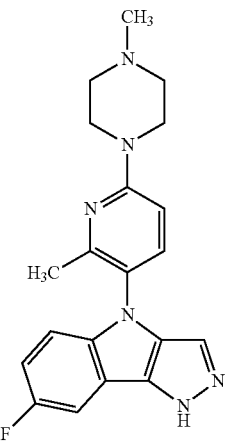 [SMILES: Cc1nc(N2CCN(C)CC2)ccc1-n1c2ccc(F)cc2c2[nH]ncc21]

A TFA salt of the title compound was prepared by a method similar to EXAMPLE 5, using 1-(5-bromo-6-methylpyridin-2-yl)-4-methylpiperazine in place of 6-bromo-5-methyl-3H-imidazo[4,5-b]pyridine. 1H NMR (400 MHz, DMSO-d$_6$) δ ppm 2.07 (s, 3 H), 2.88 (d, J=3.79 Hz, 3 H), 3.06-3.22 (m, 5 H), 3.56 (d, J=11.37 Hz, 2 H), 4.50 (d, J=13.14 Hz, 3 H), 6.95 (dt, J=8.84, 2.15 Hz, 2 H), 7.10-7.17

(m, 1 H), 7.52 (s, 1 H), 7.63-7.68 (m, 2 H). MS [M+H]⁺ calc'd for $C_{20}H_{21}FN_6$, 365.19; found 365.3.

Example 8

7-Fluoro-4-(2-(4-methylpiperazin-1-yl)pyridin-4-yl)-1,4-dihydropyrazolo[4,3-b]indole

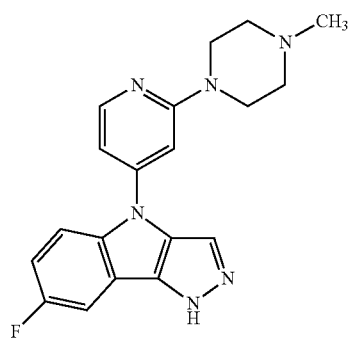 [SMILES: CN1CCN(c2cc(-n3c4ccc(F)cc4c4[nH]ncc43)ccn2)CC1]

A TFA salt of the title compound was prepared by a method similar to EXAMPLE 5, using 1-(4-bromopyridin-2-yl)-4-methylpiperazine in place of 6-bromo-5-methyl-3H-imidazo[4,5-b]pyridine. ¹H NMR (400 MHz, DMSO-d₆) δ ppm 2.86 (br s, 3 H), 3.17 (s, 6 H), 3.53 (br s, 3 H), 4.52 (br s, 2 H), 7.06 (br s, 1 H), 7.12 (d, J=5.81 Hz, 1 H), 7.26 (td, J=9.16, 2.65 Hz, 2 H), 7.91 (d, J=9.60 Hz, 1 H), 8.12 (br s, 1 H), 8.27 (d, J=5.56 Hz, 1 H). MS [M+H]⁺ calc'd for $C_{19}H_{19}FN_6$, 351.17; found 351.3.

Example 9

4-(2,4-Dimethyl-2H-indazol-5-yl)-7-fluoro-1,4-dihydropyrazolo[4,3-b]indole

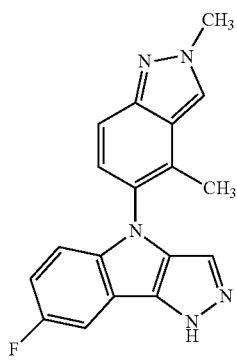 [SMILES: Cc1c(-n2c3ccc(F)cc3c3[nH]ncc32)ccc2nn(C)cc12]

A TFA salt of the title compound was prepared by a method similar to EXAMPLE 5, using 5-bromo-2,4-dimethyl-2H-indazole in place of 6-bromo-5-methyl-3H-imidazo[4,5-b]pyridine. ¹H NMR (400 MHz, DMSO-d₆) δ ppm 2.22 (s, 3 H), 4.22 (s, 3 H), 6.99 (br s, 2 H), 7.11 (dd, J=9.22, 2.65 Hz, 2 H), 7.14-7.17 (m, 2 H), 7.56 (d, J=8.84 Hz, 1 H), 8.56 (s, 1 H). MS [M+H]⁺ calc'd for $C_{18}H_{14}FN_5$, 320.13; found 320.2.

Example 10

4-(2,6-Dimethylpyridin-3-yl)-7-fluoro-1,4-dihydropyrazolo[4,3-b]indole

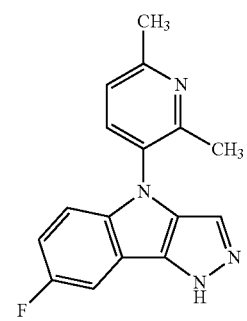

A TFA salt of the title compound was prepared by a method similar to EXAMPLE 5, using 3-bromo-2,6-dimethylpyridine in place of 6-bromo-5-methyl-3H-imidazo[4,5-b]pyridine. ¹H NMR (400 MHz, CD₃OD) δ ppm 2.32 (s, 3 H), 2.65 (s, 3 H), 7.08-7.13 (m, 1 H), 7.15-7.21 (m, 1 H), 7.53 (d, J=7.58 Hz, 1 H), 7.63 (s, 1 H), 7.69 (dd, J=8.84, 2.53 Hz, 1 H), 8.07 (d, J=7.33 Hz, 1 H). MS [M+H]⁺ calc'd for $C_{16}H_{13}FN_4$, 281.12; found 281.2.

Example 11

7-Fluoro-4-(6-methylpyridin-2-yl)-1,4-dihydropyrazolo[4,3-b]indole

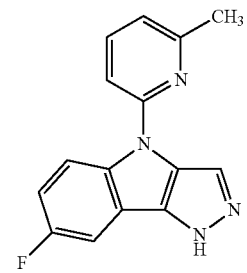 [SMILES: Cc1cccc(-n2c3ccc(F)cc3c3[nH]ncc32)n1]

A TFA salt of the title compound was prepared by a method similar to EXAMPLE 5, using 2-bromo-6-methylpyridine in place of 6-bromo-5-methyl-3H-imidazo[4,5-b]pyridine. ¹H NMR (400 MHz, DMSO-d₆) δ ppm 2.58 (s, 3 H), 7.07 (d, J=7.33 Hz, 1 H), 7.28 (td, J=9.35, 2.78 Hz, 1 H), 7.47 (br s, 1 H), 7.68 (br s, 1 H), 7.85 (t, J=7.83 Hz, 1 H), 8.22 (br s, 1 H), 8.88 (dd, J=9.47, 4.67 Hz, 1 H). MS [M+H]⁺ calc'd for $C_{15}H_{11}FN_4$, 267.10; found 267.2.

Example 12

(2R)-1-((5-(7-Fluoropyrazolo[4,3-b]indol-4(1H)-yl)-6-methylpyridin-2-yl)amino)propan-2-ol

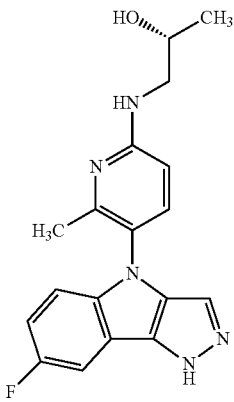 [SMILES: Cc1nc(NC[C@@H](C)O)ccc1-n1c2ccc(F)cc2c2[nH]ncc21]

A TFA salt of the title compound was prepared by a method similar to EXAMPLE 5, using (R)-1-((5-bromo-6-methylpyridin-2-yl)amino)propan-2-ol in place of 6-bromo-5-methyl-3H-imidazo[4,5-b]pyridine. 1H NMR (400 MHz, CD$_3$OD) δ ppm 1.25 (d, J=6.32 Hz, 3 H), 2.11 (s, 3 H), 3.36 (td, J=6.88, 2.15 Hz, 1 H), 3.48 (dt, J=13.89, 3.28 Hz, 1 H), 4.03 (td, J=6.63, 3.66 Hz, 1 H), 6.71 (d, J=8.84 Hz, 1 H), 7.00 (dd, J=9.09, 4.29 Hz, 1 H), 7.08-7.14 (m, 1 H), 7.45 (s, 1 H), 7.54 (d, J=9.09 Hz, 1 H), 7.60 (dd, J=8.97, 2.65 Hz, 1 H). MS [M+H]$^+$ calc'd for C$_{18}$H$_{18}$FN$_5$O, 340.16; found 340.3.

Example 13

4-(3,5-Dimethyl-3H-imidazo[4,5-b]pyridin-6-yl)-7-fluoro-1,4-dihydropyrazolo[4,3-b]indole

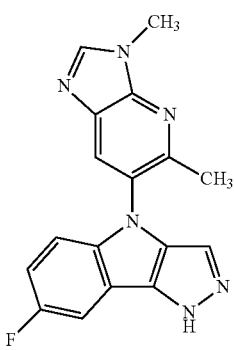 [SMILES: Cc1nc2c(cc1-n1c3ccc(F)cc3c3[nH]ncc31)ncn2C]

A TFA salt of the title compound was prepared by a method similar to EXAMPLE 5, using 6-bromo-3,5-dimethyl-3H-imidazo[4,5-b]pyridine in place of 6-bromo-5-methyl-3H-imidazo[4,5-b]pyridine. 1H NMR (400 MHz, CD$_3$OD) δ ppm 2.32 (s, 3 H), 3.99 (s, 3 H), 6.94 (dd, J=8.97, 4.17 Hz, 1 H), 7.10 (td, J=9.09, 2.78 Hz, 1 H), 7.44 (s, 1 H), 7.64 (d, J=6.82 Hz, 1 H), 8.08 (s, 1 H), 8.41 (s, 1 H). MS [M+H]$^+$ calc'd for C$_{17}$H$_{13}$FN$_6$, 321.13; found 321.3.

Example 14

4-(1,5-Dimethyl-1H-indazol-6-yl)-7-fluoro-1,4-dihydropyrazolo[4,3-b]indole

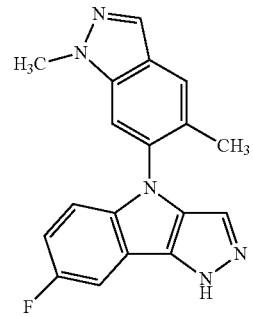 [SMILES: Cc1cc2cnn(C)c2cc1-n1c2ccc(F)cc2c2[nH]ncc21]

A TFA salt of the title compound was prepared by a method similar to EXAMPLE 5, using 6-bromo-1,5-dimethyl-1H-indazole in place of 6-bromo-5-methyl-3H-imidazo[4,5-b]pyridine. $^1$H NMR (400 MHz, DMSO-d$_6$) δ ppm 2.05 (s, 3 H), 4.02 (s, 3 H), 7.02 (dd, J=9.09, 4.29 Hz, 1 H), 7.13 (td, J=9.22, 2.78 Hz, 1 H), 7.55 (s, 1 H), 7.67 (dd, J=9.09, 2.53 Hz, 1 H), 7.80-7.85 (m, 2 H), 8.09 (d, J=1.01 Hz, 1 H). MS [M+H]$^+$ calc'd for C$_{18}$H$_{14}$FN$_5$, 320.13; found 320.2.

Example 15

4-(2,6-Dimethyl-2H-indazol-5-yl)-7-fluoro-1,4-dihydropyrazolo[4,3-b]indole

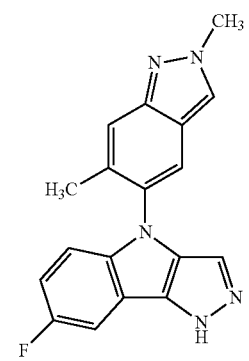 [SMILES: Cc1cc2nn(C)cc2cc1-n1c2ccc(F)cc2c2[nH]ncc21]

A TFA salt of the title compound was prepared by a method similar to EXAMPLE 5, using 5-bromo-2,6-dimethyl-2H-indazole in place of 6-bromo-5-methyl-3H-imidazo[4,5-b]pyridine. $^1$H NMR (400 MHz, DMSO-d$_6$) δ ppm 1.98 (s, 3 H), 4.19 (s, 3 H), 6.94 (dd, J=8.97, 4.67 Hz, 1 H), 7.11 (td, J=9.16, 2.65 Hz, 2 H), 7.51 (s, 1 H), 7.63-7.66 (m, 2 H), 7.79 (s, 1 H), 8.36 (s, 1 H). MS [M+H]$^+$ calc'd for C$_{18}$H$_{14}$FN$_5$, 320.13; found 320.3.

Example 16

4-(2,5-Dimethyl-2H-indazol-6-yl)-7-fluoro-1,4-dihydropyrazolo[4,3-b]indole

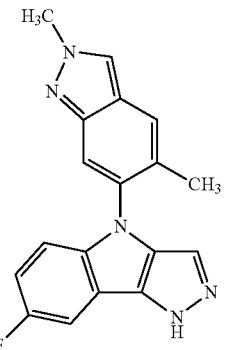

A TFA salt of the title compound was prepared by a method similar to EXAMPLE 5, using 6-bromo-2,5-dimethyl-2H-indazole in place of 6-bromo-5-methyl-3H-imidazo[4,5-b]pyridine. $^1$H NMR (400 MHz, DMSO-$d_6$) δ ppm 1.95-1.99 (m, 3 H), 4.20 (s, 4 H), 6.98 (dd, J=8.84, 4.29 Hz, 1 H), 7.12 (td, J=9.16, 2.65 Hz, 1 H), 7.53 (s, 1 H), 7.63-7.67 (m, 2 H), 7.75-7.77 (m, 1 H), 8.38 (s, 1 H). MS [M+H]$^+$ calc'd for $C_{18}H_{14}FN_5$, 320.13; found 320.3.

Example 17

4-(1,4-Dimethyl-1H-indazol-5-yl)-7-fluoro-1,4-dihydropyrazolo[4,3-b]indole

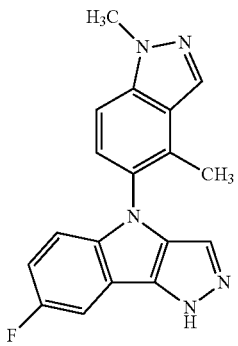 [SMILES: Cc1c(-n2c3ccc(F)cc3c3[nH]ncc32)ccc2c1cnn2C]

A TFA salt of the title compound was prepared by a method similar to EXAMPLE 5, using 5-bromo-1,4-dimethyl-1H-indazole in place of 6-bromo-5-methyl-3H-imidazo[4,5-b]pyridine. $^1$H NMR (400 MHz, DMSO-$d_6$) δ ppm 2.27 (s, 3 H), 4.11 (s, 3 H), 6.95 (dd, J=8.97, 4.17 Hz, 1 H), 7.12 (td, J=9.22, 2.78 Hz, 1 H), 7.36 (d, J=8.84 Hz, 1 H), 7.51 (s, 1 H), 7.61-7.68 (m, 2 H), 8.25 (d, J=1.01 Hz, 1 H). MS [M+H]$^+$ calc'd for $C_{18}H_{14}FN_5$, 320.13; found 320.2.

Example 18

6-Amino-5-(7-fluoropyrazolo[4,3-b]indol-4(1H)-yl)nicotinic acid

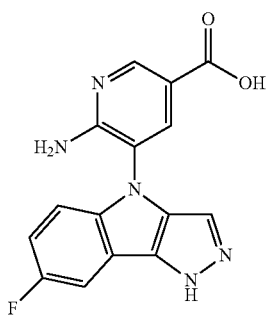 [SMILES: Nc1ncc(C(=O)O)cc1-n1c2ccc(F)cc2c2[nH]ncc21]

A TFA salt of the title compound was prepared by a method similar to EXAMPLE 5, using methyl 6-amino-5-bromonicotinate in place of 6-bromo-5-methyl-3H-imidazo[4,5-b]pyridine. $^1$H NMR (400 MHz, DMSO-$d_6$) δ ppm 3.16 (s, 1 H), 6.80 (br s, 1 H), 7.07-7.19 (m, 3 H), 7.56 (s, 1 H), 7.65 (d, J=8.59 Hz, 1 H), 7.83 (d, J=2.02 Hz, 1 H), 8.61 (d, J=2.02 Hz, 1 H). MS [M+H]$^+$ calc'd for $C_{15}H_{10}FN_5O_2$, 312.09; found 312.2.

Example 19

7-Fluoro-4-(6-methyl-1H-indazol-5-yl)-1,4-dihydropyrazolo[4,3-b]indole

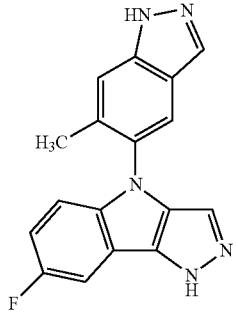 [SMILES: Cc1cc2[nH]ncc2cc1-n1c2ccc(F)cc2c2[nH]ncc21]

A TFA salt of the title compound was prepared by a method similar to EXAMPLE 5, using 5-bromo-6-methyl-1H-indazole in place of 6-bromo-5-methyl-3H-imidazo[4,5-b]pyridine. $^1$H NMR (400 MHz, DMSO-$d_6$) δ ppm 2.04 (s, 3 H), 2.54 (s, 1 H), 3.16 (s, 1 H), 6.92 (dd, J=9.09, 4.29 Hz, 1 H), 7.08-7.14 (m, 1 H), 7.51 (br s, 1 H), 7.61 (s, 1 H), 7.65 (d, J=9.35 Hz, 1 H), 7.83 (s, 1 H), 8.09 (s, 1 H). MS [M+H]$^+$ calc'd for $C_{17}H_{12}FN_5$, 306.12; found 306.2.

Example 20

(3R)-1-(5-(7-Fluoropyrazolo[4,3-b]indol-4(1H)-yl)-4-methylpyrimidin-2-yl)pyrrolidine-3-carboxamide

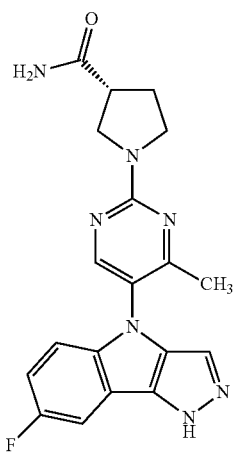 [SMILES: Cc1nc(N2CC[C@@H](C(N)=O)C2)ncc1-n1c2ccc(F)cc2c2[nH]ncc21]

A TFA salt of the title compound was prepared by a method similar to EXAMPLE 5, using (R)-1-(5-bromo-4-methylpyrimidin-2-yl)pyrrolidine-3-carboxamide in place of 6-bromo-5-methyl-3H-imidazo[4,5-b]pyridine. 1H NMR (400 MHz, CD$_3$OD) δ ppm 2.08 (s, 3 H), 2.16-2.41 (m, 2 H), 3.24 (quin, J=7.45 Hz, 1 H), 3.58-3.73 (m, 1 H), 3.73-4.00 (m, 3H), 6.97-7.08 (m, 1 H), 7.08-7.20 (m, 1 H), 7.52 (br s, 1 H), 7.62 (dd, J=8.72, 2.40 Hz, 1 H), 8.34 (s, 1 H). MS [M+H]$^+$ calc'd for C$_{19}$H$_{18}$FN$_7$O, 380.16; found 380.17.

Example 21

(3S)-1-(5-(7-Fluoropyrazolo[4,3-b]indol-4(1H)-yl)-4-methylpyrimidin-2-yl)pyrrolidine-3-carboxamide

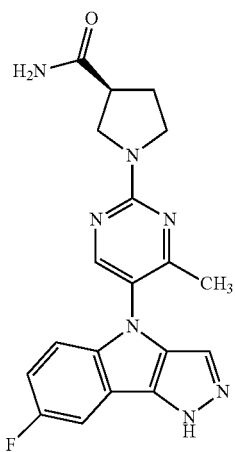 [SMILES: Cc1nc(N2CC[C@H](C(N)=O)C2)ncc1-n1c2ccc(F)cc2c2[nH]ncc21]

A TFA salt of the title compound was prepared by a method similar to EXAMPLE 5, using (S)-1-(5-bromo-4-methylpyrimidin-2-yl)pyrrolidine-3-carboxamide in place of 6-bromo-5-methyl-3H-imidazo[4,5-b]pyridine. 1H NMR (400 MHz, CD$_3$OD) δ ppm 2.07 (s, 3 H), 2.18-2.39 (m, 2 H), 3.17-3.25 (m, 1 H), 3.59-3.73 (m, 1 H), 3.74-3.97 (m, 3 H), 7.03 (dd, J=8.97, 4.17 Hz, 1 H), 7.13 (td, J=9.03, 1.89 Hz, 1 H), 7.53 (br s, 1 H), 7.62 (d, J=7.07 Hz, 1 H), 8.32 (s, 1 H). MS [M+H]$^+$ calc'd for C$_{19}$H$_{18}$FN$_7$O, 380.16; found 380.12.

Example 22

4-(7-Fluoropyrazolo[4,3-b]indol-4(1H)-yl)-1H-pyrazole-5-carbonitrile

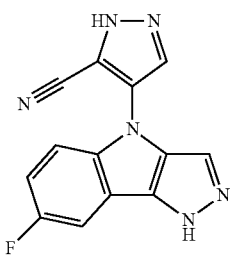 [SMILES: N#Cc1[nH]ncc1-n1c2ccc(F)cc2c2[nH]ncc21]

A TFA salt of the title compound was prepared by a method similar to EXAMPLE 5, using 4-bromo-1H-pyrazole-3-carbonitrile in place of 6-bromo-5-methyl-3H-imidazo[4,5-b]pyridine. $^1$H NMR (400 MHz, DMSO-d$_6$) δ ppm 7.23 (td, J=9.16, 2.65 Hz, 2 H), 7.38-7.43 (m, 1 H), 7.67 (d, J=8.59 Hz, 1 H), 7.75 (s, 1 H), 8.58 (s, 1 H). MS [M+H]$^+$ calc'd for C$_{13}$H$_7$FN$_6$, 267.08; found 267.1.

Example 23

4-(1-Ethyl-3,5-dimethyl-1H-pyrazol-4-yl)-7-fluoro-1,4-dihydropyrazolo[4,3-b]indole

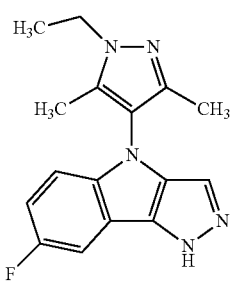 [SMILES: CCn1nc(C)c(-n2c3ccc(F)cc3c3[nH]ncc32)c1C]

A TFA salt of the title compound was prepared by a method similar to EXAMPLE 5, using 4-bromo-1-ethyl-3,5-dimethyl-1H-pyrazole in place of 6-bromo-5-methyl-3H-imidazo[4,5-b]pyridine. $^1$H NMR (400 MHz, DMSO-d$_6$) δ ppm 1.35-1.40 (m, 3 H), 1.90 (s, 3 H), 2.03 (s, 3 H), 4.08 (q, J=7.16 Hz, 2 H), 6.97 (dd, J=8.84, 4.29 Hz, 1 H), 7.13 (td, J=9.22, 2.78 Hz, 1 H), 7.55 (s, 1 H), 7.62 (dd, J=9.22, 2.65 Hz, 1 H). MS [M+H]$^+$ calc'd for C$_{16}$H$_{16}$FN$_5$, 298.15; found 298.2.

Example 24

(3R)-1-(5-(7-Fluoropyrazolo[4,3-b]indol-4(1H)-yl)-4-methylpyrimidin-2-yl)piperidin-3-ol

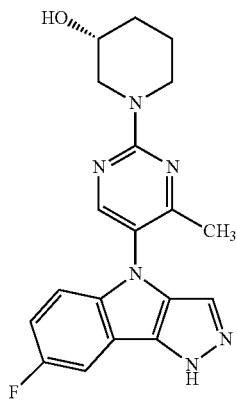 [SMILES: Cc1nc(N2CCC[C@@H](O)C2)ncc1-n1c2ccc(F)cc2c2[nH]ncc21]

A TFA salt of the title compound was prepared by a method similar to EXAMPLE 5, using (R)-1-(5-bromo-4-methylpyrimidin-2-yl)piperidin-3-ol in place of 6-bromo-5-methyl-3H-imidazo[4,5-b]pyridine. 1H NMR (400 MHz, DMSO-$d_6$) δ ppm 1.40-1.46 (m, 2 H), 1.75-1.79 (m, 1 H), 1.93 (br s, 1 H), 1.98 (s, 3 H), 2.93-3.00 (m, 1 H), 3.12 (br s, 1 H), 3.17 (s, 1 H), 3.51 (d, J=9.35 Hz, 1 H), 4.36 (d, J=12.13 Hz, 2 H), 4.51 (d, J=12.38 Hz, 2 H), 7.07 (dd, J=9.09, 4.55 Hz, 1 H), 7.13 (td, J=9.09, 2.53 Hz, 1 H), 7.61 (s, 1 H), 7.64 (dd, J=9.09, 2.53 Hz, 1 H), 8.34 (s, 1 H). MS [M+H]+ calc'd for $C_{19}H_{19}FN_6O$, 367.17; found 367.3.

Example 25

7-Fluoro-4-(4,5,6,7-tetrahydropyrazolo[1,5-a]pyrazin-3-yl)-1,4-dihydropyrazolo[4,3-b]indole

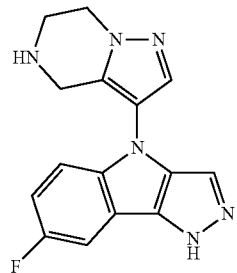 [SMILES: Fc1ccc2c(c1)c1[nH]ncc1n2-c1cnn2c1CNCC2]

A TFA salt of the title compound was prepared by a method similar to EXAMPLE 5, using 3-bromo-4,5,6,7-tetrahydropyrazolo[1,5-a]pyrazine in place of 6-bromo-5-methyl-3H-imidazo[4,5-b]pyridine. 1H NMR (400 MHz, DMSO-$d_6$) δ ppm 3.76 (t, J=5.68 Hz, 2 H), 4.33 (s, 2 H), 4.43 (t, J=5.68 Hz, 2 H), 7.20 (td, J=9.09, 2.53 Hz, 1 H), 7.28 (dd, J=9.09, 4.29 Hz, 1 H), 7.63-7.67 (m, 2 H), 7.94-7.97 (m, 1 H), 9.50 (br s, 2 H). MS [M+H]+ calc'd for $C_{15}H_3FN_6$, 297.13; found 298.2.

Example 26

7-Fluoro-4-(5-methyl-1H-indazol-6-yl)-1,4-dihydropyrazolo[4,3-b]indole

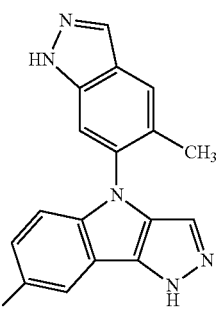

A TFA salt of the title compound was prepared by a method similar to EXAMPLE 5, using 6-bromo-5-methyl-1H-indazole in place of 6-bromo-5-methyl-3H-imidazo[4,5-b]pyridine. 1H NMR (400 MHz, DMSO-$d_6$) δ ppm 2.04 (s, 3 H), 7.02 (d, J=4.29 Hz, 2 H), 7.10-7.15 (m, 2 H), 7.55-7.59 (m, 2 H), 7.67 (d, J=9.35 Hz, 2 H), 7.84 (s, 1 H), 8.12 (d, J=1.01 Hz, 1 H). MS [M+H]+ calc'd for $C_{17}H_{12}FN_5$, 306.12; found 306.2.

Example 27

(3S)-1-(5-(7-Fluoropyrazolo[4,3-b]indol-4(1H)-yl)-6-methylpyridin-2-yl)pyrrolidin-3-ol

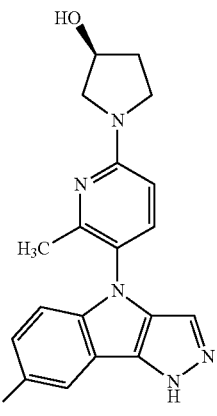

A TFA salt of the title compound was prepared by a method similar to EXAMPLE 5, using (S)-1-(5-bromo-6-methylpyridin-2-yl)pyrrolidin-3-ol in place of 6-bromo-5-methyl-3H-imidazo[4,5-b]pyridine. 1H NMR (400 MHz, DMSO-$d_6$) δ ppm 2.00 (br s, 1 H), 2.05-2.12 (m, 2 H), 2.13 (br s, 3 H), 3.47 (d, J=8.84 Hz, 1 H), 3.61 (br s, 4 H), 4.47 (br s, 2 H), 7.04 (d, J=4.04 Hz, 1 H), 7.16 (dd, J=8.84, 6.57 Hz, 1 H), 7.55 (s, 1 H), 7.65 (dd, J=8.97, 2.65 Hz, 1 H). MS [M+H]+ calc'd for $C_{19}H_{18}FN_5O$, 352.16; found 352.3.

Example 28

6-(7-Fluoropyrazolo[4,3-b]indol-4(1H)-yl)-7-methyl-1H-imidazo[4,5-b]pyridin-2(3H)-one

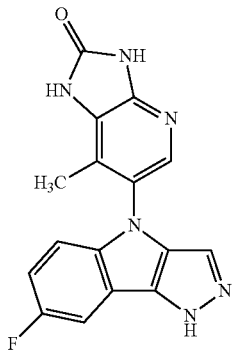 [SMILES: Cc1c(-n2c3ccc(F)cc3c3[nH]ncc32)cnc2[nH]c(=O)[nH]c12]

A TFA salt of the title compound was prepared by a method similar to EXAMPLE 5, using 6-bromo-7-methyl-1H-imidazo[4,5-b]pyridin-2(3H)-one in place of 6-bromo-5-methyl-3H-imidazo[4,5-b]pyridine. 1H NMR (400 MHz, CD$_3$OD) δ ppm 2.17 (s, 3 H), 6.99 (dd, J=8.84, 4.04 Hz, 1 H), 7.11 (td, J=9.09, 2.78 Hz, 1 H), 7.33 (s, 1 H), 7.45 (s, 1 H), 7.62 (d, J=7.83 Hz, 1 H). MS [M+H]$^+$ calc'd for C$_{16}$H$_{11}$FN$_6$O, 323.11; found 323.3.

Example 29

1-(5-(7-Fluoropyrazolo[4,3-b]indol-4(1H)-yl)-4-methylpyrimidin-2-yl)piperidin-4-ol

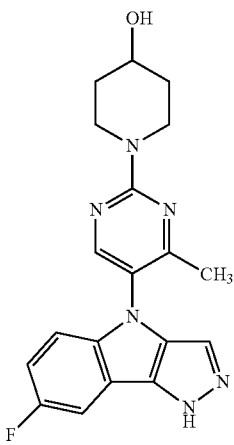 [SMILES: Cc1nc(N2CCC(O)CC2)ncc1-n1c2ccc(F)cc2c2[nH]ncc21]

A TFA salt of the title compound was prepared by a method similar to EXAMPLE 5, using 1-(5-bromo-4-methylpyrimidin-2-yl)piperidin-4-ol in place of 6-bromo-5-methyl-3H-imidazo[4,5-b]pyridine. $^1$H NMR (400 MHz, DMSO-d$_6$) δ ppm 1.34-1.44 (m, 2 H), 1.79-1.86 (m, 2 H), 1.98 (s, 3 H), 3.36 (ddd, J=13.07, 9.92, 3.03 Hz, 2 H), 3.77 (dt, J=8.72, 4.48 Hz, 1 H), 4.30-4.37 (m, 2 H), 7.05-7.16 (m, 3 H), 7.62 (s, 1 H), 7.62-7.66 (m, 1 H), 8.35 (s, 1 H). MS [M+H]$^+$ calc'd for C$_{19}$H$_{19}$FN$_6$O, 367.17; found 367.3.

Example 30

4-(3-Ethyl-5-methyl-3H-imidazo[4,5-b]pyridin-6-yl)-7-fluoro-1,4-dihydropyrazolo[4,3-b]indole

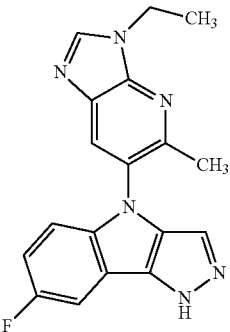 [SMILES: CCn1cnc2cc(-n3c4ccc(F)cc4c4[nH]ncc43)c(C)nc21]

A TFA salt of the title compound was prepared by a method similar to EXAMPLE 5, using 6-bromo-3-ethyl-5-methyl-3H-imidazo[4,5-b]pyridine in place of 6-bromo-5-methyl-3H-imidazo[4,5-b]pyridine. 1H NMR (400 MHz, DMSO-d$_6$) δ ppm 1.50-1.55 (m, 3 H), 2.24 (s, 3 H), 4.38 (q, J=7.07 Hz, 4 H), 6.99 (dd, J=8.97, 4.42 Hz, 1 H), 7.10-7.16 (m, 1 H), 7.57 (s, 1 H), 7.68 (dd, J=9.09, 2.53 Hz, 1 H), 8.20 (s, 1 H), 8.71 (s, 1 H). MS [M+H]$^+$ calc'd for C$_{18}$H$_{15}$FN$_6$, 335.14; found 335.3.

Example 31

7-Fluoro-4-(3-(2-methoxyethyl)-5-methyl-3H-imidazo[4,5-b]pyridin-6-yl)-1,4-dihydropyrazolo[4,3-b]indole

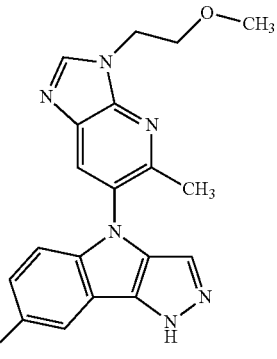

A TFA salt of the title compound was prepared by a method similar to EXAMPLE 5, using 6-bromo-3-(2-methoxyethyl)-5-methyl-3H-imidazo[4,5-b]pyridine in place of 6-bromo-5-methyl-3H-imidazo[4,5-b]pyridine. $^1$H NMR (400 MHz, DMSO-d$_6$) δ ppm 2.24 (s, 3 H), 3.81 (t, J=5.31 Hz, 2 H), 4.51 (t, J=5.31 Hz, 3 H), 7.00 (dd, J=8.97, 4.42 Hz, 1 H), 7.12 (dd, J=9.09, 2.53 Hz, 1 H), 7.58 (s, 1 H), 7.68 (dd, J=8.97, 2.40 Hz, 1 H), 8.20 (s, 1 H), 8.60 (s, 1 H). MS [M+H]$^+$ calc'd for C$_{19}$H$_{17}$FN$_6$O, 365.15; found 365.3.

Example 32

6-(7-Fluoropyrazolo[4,3-b]indol-4(1H)-yl)-1-(2-hydroxyethyl)-5-methyl-1H-imidazo[4,5-b]pyridin-2(3H)-one

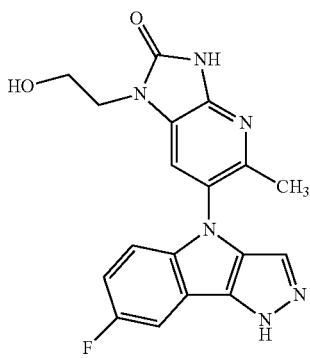 [SMILES: Cc1nc2[nH]c(=O)n(CCO)c2cc1-n1c2ccc(F)cc2c2[nH]ncc21]

A TFA salt of the title compound was prepared by a method similar to EXAMPLE 5, using tert-butyl 6-bromo-1-(2-hydroxyethyl)-5-methyl-2-oxo-1H-imidazo[4,5-b]pyridine-3(2H)-carboxylate in place of 6-bromo-5-methyl-3H-imidazo[4,5-b]pyridine. 1H NMR (400 MHz, CD$_3$OD) δ ppm 2.17-2.23 (m, 3 H), 3.89-3.98 (m, 2 H), 4.10-4.19 (m, 2 H), 7.01 (dd, J=8.97, 4.17 Hz, 1 H), 7.13 (td, J=9.09, 2.53 Hz, 1 H), 7.36 (s, 1 H), 7.51 (s, 1 H), 7.64 (dd, J=8.72, 2.65 Hz, 1 H). MS [M+H]$^+$ calc'd for C$_{18}$H$_{15}$FN$_6$O$_2$, 367.13; found 367.3.

Example 33

3-((S)-2,3-Dihydroxypropyl)-6-(7-fluoropyrazolo[4,3-b]indol-4(1H)-yl)-5-methyl-1H-imidazo[4,5-b]pyridin-2(3H)-one

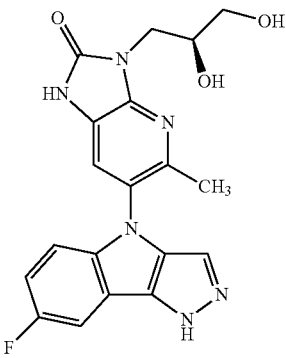 [SMILES: Cc1nc2c(cc1-n1c3ccc(F)cc3c3[nH]ncc31)[nH]c(=O)n2C[C@H](O)CO]

A TFA salt of the title compound was prepared by a method similar to EXAMPLE 5, using (S)-6-bromo-3-((2,2-dimethyl-1,3-dioxolan-4-yl)methyl)-5-methyl-1H-imidazo[4,5-b]pyridin-2(3 H)-one in place of 6-bromo-5-methyl-3H-imidazo[4,5-b]pyridine. $^1$H NMR (400 MHz, CD$_3$OD) δ ppm 2.17-2.23 (m, 3 H), 3.60-3.66 (m, 2 H), 4.06-4.52 (m, 3 H), 7.03 (dd, J=9.09, 4.29 Hz, 1 H), 7.11-7.21 (m, 1 H), 7.37-7.42 (m, 1 H), 7.59 (d, J=2.02 Hz, 1 H), 7.65 (dd, J=8.72, 2.40 Hz, 1 H). MS [M+H]$^+$ calc'd for C$_{19}$H$_{17}$FN$_6$O$_3$, 397.14; found 397.3.

Example 34

7-Fluoro-4-(2-((S)-3-fluoropyrrolidin-1-yl)-4-methylpyrimidin-5-yl)-1,4-dihydropyrazolo[4,3-b]indole

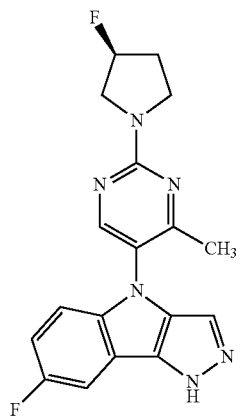 [SMILES: Cc1nc(N2CC[C@H](F)C2)ncc1-n1c2ccc(F)cc2c2[nH]ncc21]

A TFA salt of the title compound was prepared by a method similar to EXAMPLE 5, using (S)-5-bromo-2-(3-fluoropyrrolidin-1-yl)-4-methylpyrimidine in place of 6-bromo-5-methyl-3H-imidazo[4,5-b]pyridine. 1H NMR (400 MHz, DMSO-d$_6$) δ ppm 1.99-2.01 (m, 3 H), 2.28 (d, J=11.87 Hz, 2 H), 3.53-3.61 (m, 2 H), 3.64-3.72 (m, 2 H), 3.72-3.82 (m, 3 H), 3.84 (br s, 3 H), 5.40 (br s, 1 H), 5.54 (br s, 1 H), 7.07 (br s, 1 H), 7.10-7.17 (m, 2 H), 7.60 (s, 1 H), 7.64 (dd, J=9.09, 2.53 Hz, 1 H), 8.39-8.40, (m, 1 H). MS [M+H]$^+$ calc'd for C$_{18}$H$_{16}$F$_2$N$_6$, 355.15; found 355.3.

Example 35

(3R)-1-(5-(7-Fluoropyrazolo[4,3-b]indol-4(1H)-yl)-4-methylpyrimidin-2-yl)-N,N-dimethylpyrrolidin-3-amine

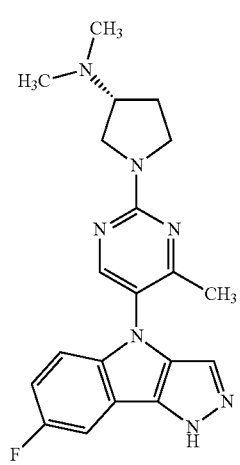 [SMILES: Cc1nc(N2CC[C@@H](N(C)C)C2)ncc1-n1c2ccc(F)cc2c2[nH]ncc21]

A TFA salt of the title compound was prepared by a method similar to EXAMPLE 5, using (R)-1-(5-bromo-4-methylpyrimidin-2-yl)-N,N-dimethylpyrrolidin-3-amine in place of 6-bromo-5-methyl-3H-imidazo[4,5-b]pyridine. $^1$H NMR (400 MHz, DMSO-d$_6$) δ ppm 2.02 (s, 3 H), 2.18-2.28 (m, 1 H), 2.46 (d, J=7.07 Hz, 1 H), 3.56 (dt, J=11.68, 7.93

Hz, 1 H), 3.64-3.72 (m, 1 H), 3.80-3.88 (m, 1 H), 3.96-4.08 (m, 3 H), 7.03 (dd, J=8.72, 4.42 Hz, 1 H), 7.12-7.18 (m, 1 H), 7.57 (d, J=1.01 Hz, 1 H), 7.66 (dd, J=8.97, 2.65 Hz, 1 H), 8.43 (s, 1 H), 10.12 (br s, 1 H). MS [M+H]+ calc'd for C20H22FN7, 380.20; found 380.4.

Example 36

7-Fluoro-4-(2-((R)-3-fluoropyrrolidin-1-yl)-4-methylpyrimidin-5-yl)-1,4-dihydropyrazolo[4,3-b]indole

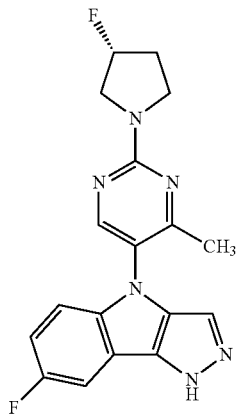 [SMILES: Cc1nc(N2CC[C@@H](F)C2)ncc1-n1c2ccc(F)cc2c2[nH]ncc21]

A TFA salt of the title compound was prepared by a method similar to EXAMPLE 5, using (R)-5-bromo-2-(3-fluoropyrrolidin-1-yl)-4-methylpyrimidine in place of 6-bromo-5-methyl-3H-imidazo[4,5-b]pyridine. 1H NMR (400 MHz, DMSO-d6) δ ppm 2.00 (d, J=0.76 Hz, 3 H), 2.24-2.33 (m, 2 H), 3.57 (td, J=10.99, 7.33 Hz, 1 H), 3.67 (dd, J=13.77, 3.16 Hz, 1 H), 3.77 (dd, J=13.89, 3.54 Hz, 1 H), 3.81-3.95 (m, 3 H), 5.40 (br s, 1 H), 5.54 (br s, 1 H), 7.07 (br s, 1 H), 7.10-7.17 (m, 1 H), 7.60 (s, 1 H), 7.64 (dd, J=9.09, 2.78 Hz, 1 H), 8.39 (s, 1 H). MS [M+H]+ calc'd for C18H16F2N6, 355.15; found 355.3.

Example 37

(3S)-1-(5-(7-Fluoropyrazolo[4,3-b]indol-4(1H)-yl)-4-methylpyrimidin-2-yl)piperidin-3-ol

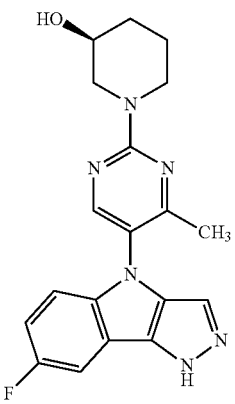 [SMILES: Cc1nc(N2CCC[C@H](O)C2)ncc1-n1c2ccc(F)cc2c2[nH]ncc21]

A TFA salt of the title compound was prepared by a method similar to EXAMPLE 5, using (S)-1-(5-bromo-4-methylpyrimidin-2-yl)piperidin-3-ol in place of 6-bromo-5-methyl-3H-imidazo[4,5-b]pyridine. 1H NMR (400 MHz, DMSO-d6) δ ppm 1.40-1.47 (m, 2 H), 1.76 (d, J=4.55 Hz, 1 H), 1.94 (br s, 1 H), 1.98 (s, 3 H), 2.93-3.00 (m, 1 H), 3.12 (br s, 1 H), 3.53 (br s, 1 H), 4.37 (d, J=10.61 Hz, 2 H), 4.52 (d, J=9.35 Hz, 2 H), 7.05-7.09 (m, 1 H), 7.10-7.16 (m, 1 H), 7.61 (s, 1 H), 7.64 (dd, J=9.22, 2.40 Hz, 1 H), 8.34 (s, 1 H). MS [M+H]+ calc'd for C19H19FN6O, 367.17; found 367.4.

Example 38

(2S)-1-(5-(7-Fluoropyrazolo[4,3-b]indol-4(1H)-yl)-4-methylpyrimidin-2-yl)-N-methylpyrrolidine-2-carboxamide

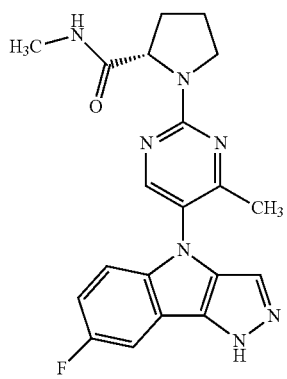 [SMILES: CNC(=O)[C@@H]1CCCN1c1ncc(-n2c3ccc(F)cc3c3[nH]ncc32)c(C)n1]

A TFA salt of the title compound was prepared by a method similar to EXAMPLE 5, using (S)-1-(5-bromo-4-methylpyrimidin-2-yl)-N-methylpyrrolidine-2-carboxamide in place of 6-bromo-5-methyl-3H-imidazo[4,5-b]pyridine. 1H NMR (400 MHz, DMSO-d6) δ ppm 1.96 (br s, 6 H), 2.19 (br s, 1 H), 2.60 (d, J=4.29 Hz, 3 H), 3.63 (d, J=7.33 Hz, 2 H), 3.73 (br s, 2 H), 4.47 (d, J=8.84 Hz, 2 H), 7.02 (dd, J=9.09, 4.29 Hz, 1 H), 7.15 (br s, 1 H), 7.59 (s, 1 H), 7.65 (dd, J=8.97, 2.65 Hz, 1 H), 7.87 (d, J=4.80 Hz, 1 H), 8.37 (br s, 1 H). MS [M+H]+ calc'd for C20H20FN7O, 394.18; found 394.4.

Example 39

4-(5-(7-Fluoropyrazolo[4,3-b]indol-4(1H)-yl)-4-methylpyrimidin-2-yl)-1-methylpiperazin-2-one

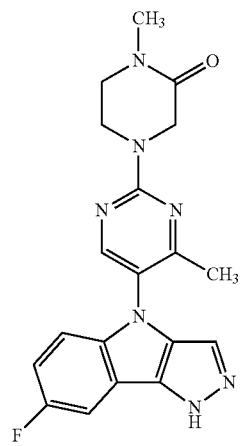 [SMILES: Cc1nc(N2CCN(C)C(=O)C2)ncc1-n1c2ccc(F)cc2c2[nH]ncc21]

A TFA salt of the title compound was prepared by a method similar to EXAMPLE 5, using 4-(5-bromo-4-methylpyrimidin-2-yl)-1-methylpiperazin-2-one in place of 6-bromo-5-methyl-3H-imidazo[4,5-b]pyridine. ¹H NMR (400 MHz, DMSO-d₆) δ ppm 2.03 (s, 3 H), 2.92 (s, 3 H), 3.44-3.47 (m, 3 H), 4.05-4.09 (m, 3 H), 4.32 (s, 2 H), 7.07 (dd, J=9.09, 4.29 Hz, 1 H), 7.14 (td, J=9.09, 2.53 Hz, 1 H), 7.60 (s, 1 H), 7.65 (dd, J=8.97, 2.65 Hz, 1 H), 8.45 (s, 1 H). MS [M+H]⁺ calc'd for C₁₉H₁₈FN₇O, 380.16; found 380.4.

Example 40

5-(7-Fluoropyrazolo[4,3-b]indol-4(1H)-yl)-6-methylpyridin-2(1H)-one

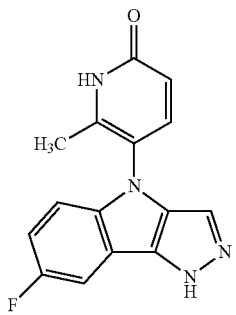 [SMILES: Cc1[nH]c(=O)ccc1-n1c2ccc(F)cc2c2[nH]ncc21]

A TFA salt of the title compound was prepared by a method similar to EXAMPLE 5, using 5-bromo-6-methylpyridin-2(1H)-one in place of 6-bromo-5-methyl-3H-imidazo[4,5-b]pyridine. ¹H NMR (400 MHz, DMSO-d₆) δ ppm 1.68 (d, J=1.01 Hz, 3 H), 6.40 (s, 1 H), 7.07-7.11 (m, 1 H), 7.12-7.17 (m, 1 H), 7.60-7.64 (m, 2 H), 7.68 (s, 1 H). MS [M+H]⁺ calc'd for C₁₅H₁₁FN₄O, 283.10; found 283.2.

Example 41

5-(7-Fluoropyrazolo[4,3-b]indol-4(1H)-yl)-4-methylpyridin-2-amine

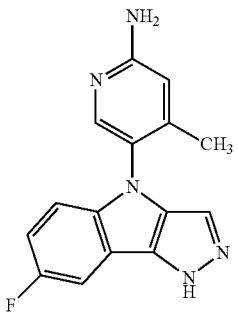 [SMILES: Cc1cc(N)ncc1-n1c2ccc(F)cc2c2[nH]ncc21]

A TFA salt of the title compound was prepared by a method similar to EXAMPLE 5, using 5-bromo-4-methylpyridin-2-amine in place of 6-bromo-5-methyl-3H-imidazo[4,5-b]pyridine. ¹H NMR (400 MHz, DMSO-d₆) δ ppm 1.94 (s, 3 H), 6.93 (s, 1 H), 7.17-7.20 (m, 2 H), 7.62 (s, 1 H), 7.66 (d, J=7.83 Hz, 2 H), 8.22 (s, 1 H). MS [M+H]⁺ calc'd for C₁₅H₁₂FN₅, 282.12; found 282.2.

Example 42

5-(7-Fluoropyrazolo[4,3-b]indol-4(1H)-yl)-6-methylpyridin-2-amine

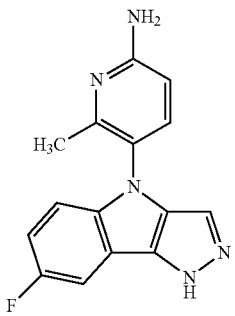 [SMILES: Cc1nc(N)ccc1-n1c2ccc(F)cc2c2[nH]ncc21]

A TFA salt of the title compound was prepared by a method similar to EXAMPLE 5, using 5-bromo-6-methylpyridin-2-amine in place of 6-bromo-5-methyl-3H-imidazo[4,5-b]pyridine. ¹H NMR (400 MHz, DMSO-d₆) δ ppm 2.18 (s, 3 H), 6.90 (d, J=8.84 Hz, 1 H), 7.16-7.22 (m, 2 H), 7.62 (s, 1 H), 7.67 (d, J=9.09 Hz, 1 H), 7.90 (d, J=8.59 Hz, 2 H). MS [M+H]⁺ calc'd for C₁₅H₁₂FN₅, 282.12; found 282.2.

Example 43

4-(2-(3,3-Difluoroazetidin-1-yl)-4-methylpyrimidin-5-yl)-7-fluoro-1,4-dihydropyrazolo[4,3-b]indole

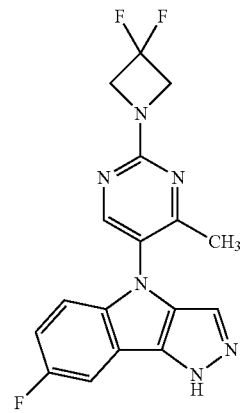 [SMILES: Cc1nc(N2CC(F)(F)C2)ncc1-n1c2ccc(F)cc2c2[nH]ncc21]

A TFA salt of the title compound was prepared by a method similar to EXAMPLE 5, using 5-bromo-2-(3,3-difluoroazetidin-1-yl)-4-methylpyrimidine in place of 6-bromo-5-methyl-3H-imidazo[4,5-b]pyridine. 1H NMR (400 MHz, DMSO-d₆) δ ppm 2.05 (s, 3 H), 4.56 (t, J=12.51 Hz, 5 H), 7.05-7.10 (m, 1 H), 7.14 (dd, J=9.09, 2.53 Hz, 1 H), 7.61 (s, 1 H), 7.65 (dd, J=9.22, 2.40 Hz, 1 H), 8.49 (s, 1 H). MS [M+H]⁺ calc'd for C₁₇H₁₃F₃N₆, 359.12; found 359.3.

Example 44

4-(5-(7-Fluoropyrazolo[4,3-b]indol-4(1H)-yl)-4-methylpyrimidin-2-yl)piperazin-2-one

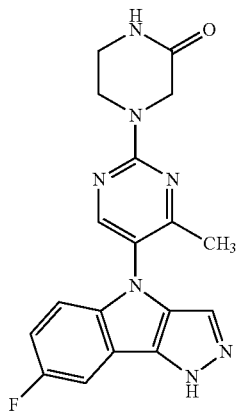 [SMILES: Cc1nc(N2CCNC(=O)C2)ncc1-n1c2ccc(F)cc2c2[nH]ncc21]

A TFA salt of the title compound was prepared by a method similar to EXAMPLE 5, using 4-(5-bromo-4-methylpyrimidin-2-yl)piperazin-2-one in place of 6-bromo-5-methyl-3H-imidazo[4,5-b]pyridine. $^1$H NMR (400 MHz, DMSO-$d_6$) δ ppm 2.03 (s, 3 H), 3.33 (br s, 3 H), 3.97-4.01 (m, 2 H), 4.26 (s, 2 H), 7.06-7.17 (m, 2 H), 7.60-7.65 (m, 2 H), 8.16 (s, 1 H), 8.44 (s, 1 H). MS [M+H]$^+$ calc'd for $C_{18}H_{16}FN_7O$, 366.15; found 366.2.

Example 45

5-(7-Fluoropyrazolo[4,3-b]indol-4(1H)-yl)-N,4-dimethylpyridin-2-amine

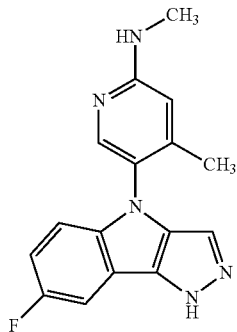 [SMILES: CNc1cc(C)c(-n2c3ccc(F)cc3c3[nH]ncc32)cn1]

A TFA salt of the title compound was prepared by a method similar to EXAMPLE 5, using 5-bromo-N,4-dimethylpyridin-2-amine in place of 6-bromo-5-methyl-3H-imidazo[4,5-b]pyridine. $^1$H NMR (400 MHz, DMSO-$d_6$) δ ppm 1.91 (s, 3 H), 2.94 (s, 3 H), 6.91 (br s, 1 H), 7.09-7.20 (m, 3 H), 7.59 (s, 1 H), 7.66 (d, J=9.09 Hz, 1 H), 8.19 (s, 1 H). MS [M+H]$^+$ calc'd for $C_{16}H_{14}FN_5$, 296.13; found 296.2.

Example 46

7-Fluoro-4-(1-methyl-1H-pyrazol-5-yl)-1,4-dihydropyrazolo[4,3-b]indole

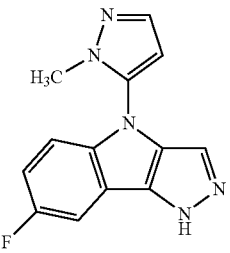 [SMILES: Cn1nccc1-n1c2ccc(F)cc2c2[nH]ncc21]

A TFA salt of the title compound was prepared by a method similar to EXAMPLE 5, using 5-bromo-1-methyl-1H-pyrazole in place of 6-bromo-5-methyl-3H-imidazo[4,5-b]pyridine. $^1$H NMR (400 MHz, CD$_3$OD) δ ppm 3.68 (s, 3 H), 6.44 (d, J=2.02 Hz, 1 H), 7.10-7.21 (m, 2 H), 7.54-7.69 (m, 3 H). MS [M+H]$^+$ calc'd for $C_{13}H_{10}FN_5$, 256.10; found 256.08.

Example 47

(1-(5-(7-Fluoropyrazolo[4,3-b]indol-4(1H)-yl)-4-methylpyrimidin-2-yl)azetidin-3-yl)methanol

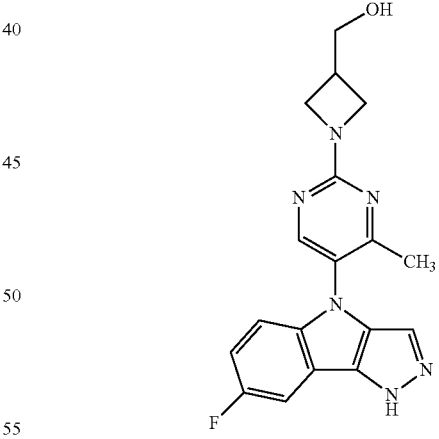

A TFA salt of the title compound was prepared by a method similar to EXAMPLE 5, using (1-(5-bromo-4-methylpyrimidin-2-yl)azetidin-3-yl)methanol in place of 6-bromo-5-methyl-3H-imidazo[4,5-b]pyridine. 1H NMR (400 MHz, DMSO-$d_6$) δ ppm 1.97 (s, 3 H), 3.60 (d, J=6.06 Hz, 2 H), 3.86 (dd, J=9.09, 5.31 Hz, 3 H), 4.10 (d, J=8.34 Hz, 3 H), 7.04 (dd, J=9.09, 4.29 Hz, 1 H), 7.10-7.16 (m, 1 H), 7.59 (s, 1 H), 7.64 (dd, J=9.09, 2.53 Hz, 1 H), 8.34 (s, 1 H). MS [M+H]$^+$ calc'd for $C_{18}H_{17}FN_6O$, 353.15; found 353.3.

Example 48

5-(7-Fluoropyrazolo[4,3-b]indol-4(1H)-yl)-1-methyl-1H-pyrazole-3-carboxamide

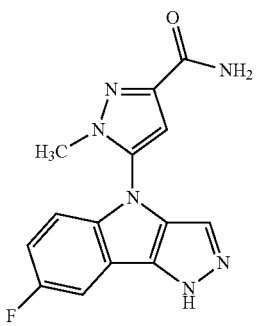 [SMILES: Cn1nc(C(N)=O)cc1-n1c2ccc(F)cc2c2[nH]ncc21]

A TFA salt of the title compound was prepared by a method similar to EXAMPLE 5, using 5-bromo-1-methyl-1H-pyrazole-3-carboxamide in place of 6-bromo-5-methyl-3H-imidazo[4,5-b]pyridine. $^1$H NMR (400 MHz, CD$_3$OD) δ ppm 3.74 (s, 3 H), 6.89 (s, 1 H), 7.13-7.24 (m, 2 H), 7.59-7.69 (m, 2 H). MS [M+H]$^+$ calc'd for C$_{14}$H$_{11}$FN$_6$O, 299.11; found 299.14.

Example 49

7-Fluoro-4-(4-methylpyrimidin-5-yl)-1,4-dihydropyrazolo[4,3-b]indole

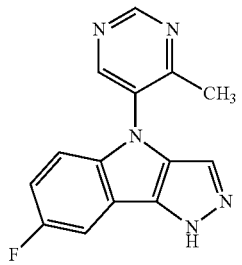 [SMILES: Cc1ncncc1-n1c2ccc(F)cc2c2[nH]ncc21]

A TFA salt of the title compound was prepared by a method similar to EXAMPLE 5, using 5-bromo-4-methylpyrimidine in place of 6-bromo-5-methyl-3H-imidazo[4,5-b]pyridine. $^1$H NMR (400 MHz, CD$_3$OD) δ ppm 2.37 (s, 3 H), 7.09-7.13 (m, 1 H), 7.13-7.19 (m, 1 H), 7.57 (s, 1 H), 7.66 (dd, J=9.09, 2.27 Hz, 1 H), 8.85 (s, 1 H), 9.13 (s, 1 H). MS [M+H]$^+$ calc'd for C$_{14}$H$_{10}$FN$_5$, 268.10; found 268.2.

Example 50

4-(7-Fluoropyrazolo[4,3-b]indol-4(1H)-yl)-N-(2-hydroxyethyl)benzamide

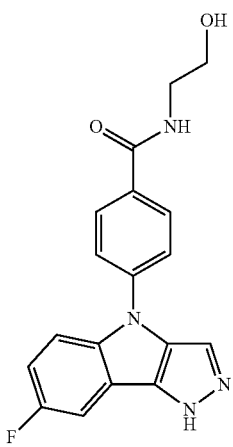 [SMILES: O=C(NCCO)c1ccc(-n2c3ccc(F)cc3c3[nH]ncc32)cc1]

Step A: 4-(7-Fluoro-1-(tetrahydro-2H-pyran-2-yl)pyrazolo[4,3-b]indol-4(1H)-yl)benzoic acid

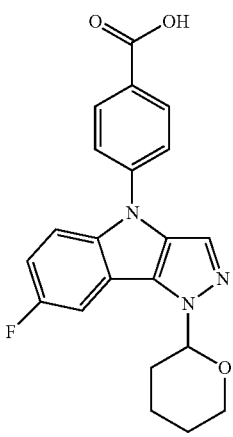 [SMILES: O=C(O)c1ccc(-n2c3ccc(F)cc3c3c2cnn3C2CCCCO2)cc1]

7-Fluoro-1-(tetrahydro-2H-pyran-2-yl)-1,4-dihydropyrazolo[4,3-b]indole (75 mg, 0.289 mmol), methyl 4-bromobenzoate (106 mg, 0.492 mmol), copper(I) iodide (5.51 mg, 0.029 mmol), Cs$_2$CO$_3$ (283 mg, 0.868 mmol) and DMF (3 mL) were mixed in an 8 mL tube equipped with a magnetic stir bar to give a brown suspension. The solvent was purged with nitrogen and the tube was sealed. The reaction mixture was heated in a microwave for 60 minutes at 220° C. The reaction mixture was filtered and acidified with aqueous 1N HCl (50 mL). A tan solid was filtered and dried to give the title compound, which was used without further purification (20 mg, 18%).

Step B: 4-(7-Fluoro-1-(tetrahydro-2H-pyran-2-yl) pyrazolo[4,3-b]indol-4(1H)-yl)-N-(2-hydroxyethyl) benzamide

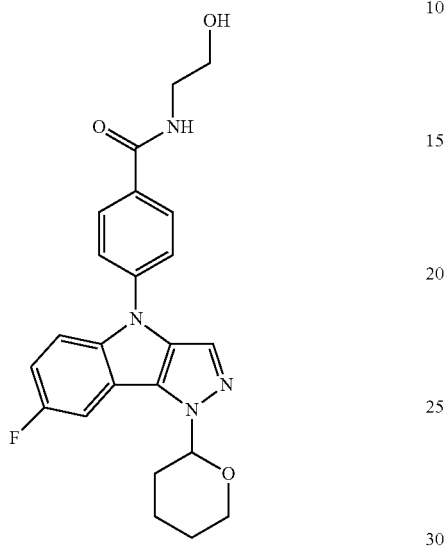

4-(7-Fluoro-1-(tetrahydro-2H-pyran-2-yl)pyrazolo[4,3-b]indol-4(1H)-yl)benzoic acid (20 mg, 0.053 mmol), 2-aminoethanol (4.83 mg, 0.079 mmol), HATU (22.05 mg, 0.058 mmol), DIPEA (0.028 mL, 0.158 mmol), and DMF (1 mL) were mixed in a 4 mL vial equipped with a magnetic stir bar. The resulting tan solution was stirred for 3 hours at room temperature. The reaction mixture was then poured into water (15 mL) and extracted with EtOAc (2×15 mL). The combined organic layers were washed with brine, dried over $Na_2SO_4$, filtered, and concentrated to give the title compound, which was used without further purification.

Step C: 4-(7-Fluoropyrazolo[4,3-b]indol-4(1H)-yl)-N-(2-hydroxyethyl)benzamide The THP protecting group of 4-(7-Fluoro-1-(tetrahydro-2H-pyran-2-yl)pyrazolo[4,3-b]indol-4(1H)-yl)-N-(2-hydroxyethyl)benzamide was removed in a manner similar to STEP B of EXAMPLE 5 to give a TFA salt of the title compound. $^1$H NMR (400 MHz, DMSO-$d_6$) δ ppm 3.51-3.56 (m, 3 H), 7.22-7.28 (m, 1 H), 7.69 (d, J=8.08 Hz, 1 H), 7.74-7.79 (m, 2 H), 7.81 (dd, J=9.22, 4.42 Hz, 1 H), 7.96 (br s, 1 H), 8.04-8.08 (m, 2 H), 8.53 (t, J=5.56 Hz, 1 H). MS [M+H]$^+$ calc'd for $C_{18}H_{15}FN_2O_2$, 339.13; found 339.2.

Example 51

4-(7-Fluoropyrazolo[4,3-b]indol-4(1H)-yl)-N-(2-hydroxyethyl)-3-methylbenzamide

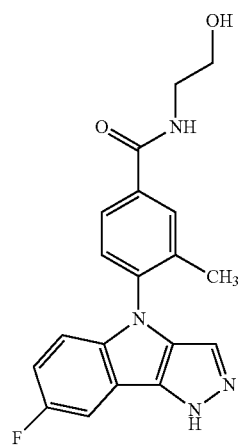 [SMILES: Cc1cc(C(=O)NCCO)ccc1-n1c2ccc(F)cc2c2[nH]ncc21]

A TFA salt of the title compound was prepared by a method similar to EXAMPLE 50, using methyl 4-bromo-3-methylbenzoate in place of methyl 4-bromobenzoate. 1H NMR (400 MHz, DMSO-$d_6$) δ ppm 2.13-2.15 (m, 3 H), 3.36 (q, J=5.98 Hz, 2 H), 3.50-3.56 (m, 3 H), 4.55 (t, J=5.18 Hz, 1 H), 7.03-7.08 (m, 1 H), 7.13-7.19 (m, 1 H), 7.49 (d, J=8.34 Hz, 1 H), 7.58 (s, 1 H), 7.67 (dd, J=8.97, 2.65 Hz, 1 H), 7.79-7.86 (m, 1 H), 7.94-8.00 (m, 1 H), 8.51-8.55 (m, 1 H). MS [M+H]$^+$ calc'd for $C_{19}H_{17}FN_4O_2$, 353.14; found 353.3.

Example 52

(4-((7-Fluoropyrazolo[4,3-b]indol-4(1H)-yl)methyl)phenyl)(morpholino)methanone

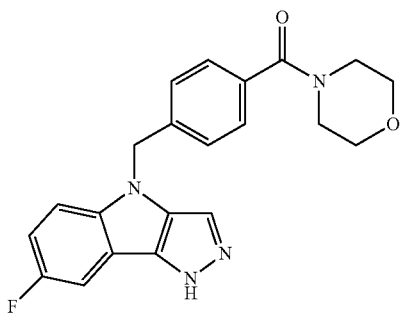 [SMILES: O=C(c1ccc(Cn2c3ccc(F)cc3c3[nH]ncc32)cc1)N1CCOCC1]

Step A: Methyl 4-((7-fluoro-1-(tetrahydro-2H-pyran-2-yl)pyrazolo[4,3-b]indol-4(1H)-yl)methyl)benzoate

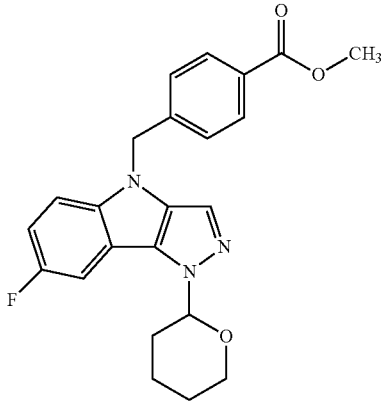 [SMILES: COC(=O)c1ccc(Cn2c3ccc(F)cc3c3c2cnn3C2CCCCO2)cc1]

To a solution of 7-fluoro-1-(tetrahydro-2H-pyran-2-yl)-1,4-dihydropyrazolo[4,3-b]indole (200 mg, 0.39 mmol, 1 eq) in ethanol was added KOH (56 mg, 1.2 eq). The reaction mixture was stirred at room temperature for 5 minutes and then concentrated. Acetone (5 mL) and methyl 4-(bromomethyl)benzoate (176 mg, 1.0 eq) were added. The reaction mixture was stirred for an additional 5 minutes at room temperature, filtered, and concentrated to give the title compound (250 mg, 80%). MS [M+H]$^+$ calc'd for $C_{23}H_{22}FN_3O_3$, 408.17; found 408.

Step B: 4-((7-Fluoro-1-(tetrahydro-2H-pyran-2-yl)pyrazolo[4,3-b]indol-4(1H)-yl)methyl)benzoic acid

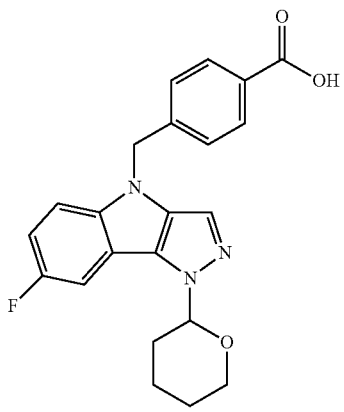 [SMILES: O=C(O)c1ccc(Cn2c3ccc(F)cc3c3c2cnn3C2CCCCO2)cc1]

To a solution of methyl 4-((7-fluoro-1-(tetrahydro-2H-pyran-2-yl)pyrazolo[4,3-b]indol-4(1H)-yl)methyl)benzoate (150 mg, 0.37 mmol) in MeOH (4 mL) and water (4 mL) was added KOH (82 mg, 4.0 eq). The solution was heated at 60° C. for 3 hours and then cooled to room temperature. Saturated aqueous NH$_4$Cl (10 mL) was added and the product was extracted into EtOAc (3×10 mL). The combined organic layers were washed with brine, dried over Na$_2$SO$_4$, filtered, and concentrated to give the title compound as a solid (120 mg, 83%). [M+H]$^+$ calc'd for $C_{22}H_{20}FN_3O_3$, 394.16; found 394.

Step C: (4-((7-Fluoro-1-(tetrahydro-2H-pyran-2-yl)pyrazolo[4,3-b]indol-4(1H)-yl)methyl)phenyl)(morpholino)methanone

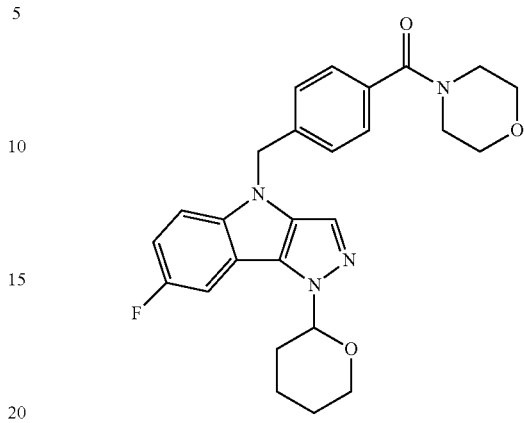

A mixture of 4-((7-fluoro-1-(tetrahydro-2H-pyran-2-yl)pyrazolo[4,3-b]indol-4(1H)-yl)methyl)benzoic acid (65 mg, 0.16 mmol, 1.0 eq), morpholine (28.8 mg, 2.0 eq), EDC (63 mg, 2.0 eq), HOBt (45 mg, 2.0 eq), and DIPEA (42 mg, 2.0 eq) in DMF (5 mL) was stirred at 20° C. under nitrogen for 2 hours. Water (5 mL) was subsequently added and the mixture was extracted with EtOAc (3×10 mL). The combined organic layers were washed with brine, dried over Na$_2$SO$_4$, filtered, and concentrated to give the title compound as an oil (70 mg, 92%). [M+H]$^+$ calc'd for $C_{26}H_{27}FN_4O_3$, 463.21; found 463.

Step D: (4-((7-Fluoropyrazolo[4,3-b]indol-4(1H)-yl)methyl)phenyl)(morpholino)methanone To a solution of (4-((7-fluoro-1-(tetrahydro-2H-pyran-2-yl)pyrazolo[4,3-b]indol-4(1H)-yl)methyl)phenyl)(morpholino)methanone (60 mg) in ethanol was added concentrated HCl (1 mL). The reaction mixture was stirred at 40° C. for 3 hours, then concentrated and its pH adjusted to 8 with saturated aq NaHCO$_3$. The reaction mixture was extracted with EtOAc (2×20 mL) and washed with brine. The organic layer was dried over Na$_2$SO$_4$, filtered, and concentrated to yield an oil which was purified by preparative HPLC to give the title compound as a white solid (30 mg, 62%). $^1$H NMR (400 MHz, DMSO-d$_6$) δ ppm 12.98 (s, 1H), 7.56 (m, 3H), 7.34-7.32 (d, 2H, J=8.0 Hz), 7.29-7.27 (d, 2H, J=8.0 Hz), 7.18-7.13 (m, 1H), 5.43 (s, 2H), 3.55 (m, 6H), 3.32 (m, 2H). [M+H]$^+$ calc'd for $C_{21}H_{19}FN_4O_2$, 379.16; found 379.

Example 53

(4-((7-Fluoropyrazolo[4,3-b]indol-4(1H)-yl)methyl)phenyl)(4-methylpiperazin-1-yl)methanone

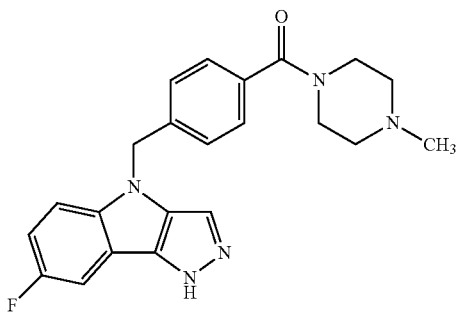 [SMILES: CN1CCN(C(=O)c2ccc(Cn3c4ccc(F)cc4c4[nH]ncc43)cc2)CC1]

The title compound was prepared by a method similar to EXAMPLE 52, using 1-methylpiperazine in place of morpholine. $^1$H NMR: (400 MHz, DMSO-$d_6$) δ ppm 13.02 (s, 1H), 7.55 (m, 3H), 7.28 (m, 4H), 7.16 (m, 1H), 5.42 (s, 2H), 3.55 (m, 2H), 3.24 (m, 2H), 2.30-2.16 (m, 7H). MS [M+H]$^+$ calc'd for $C_{22}H_{22}FN_5O$, 392.19; found 392.

Example 54

4-((7-Fluoropyrazolo[4,3-b]indol-4(1H)-yl)methyl)-N-(2-hydroxyethyl)benzamide

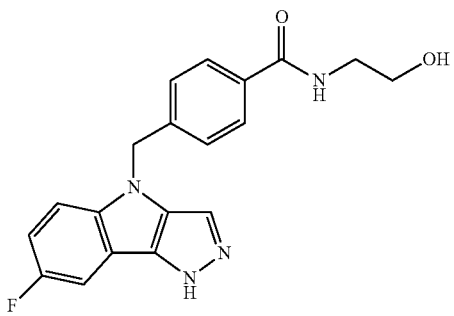 [SMILES: O=C(NCCO)c1ccc(Cn2c3ccc(F)cc3c3[nH]ncc32)cc1]

Step A: Methyl 4-((7-fluoro-1-(tetrahydro-2H-pyran-2-yl)pyrazolo[4,3-b]indol-4(1H)-yl)methyl)benzoate

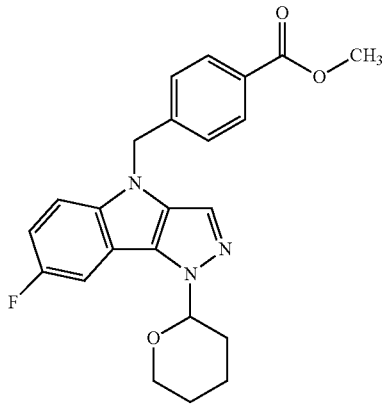 [SMILES: COC(=O)c1ccc(Cn2c3ccc(F)cc3c3c2cnn3C2CCCCO2)cc1]

The title compound was prepared by a method similar to STEP D of EXAMPLE 1, using methyl 4-(bromomethyl)benzoate in place of (bromomethyl)benzene. MS [M+H]$^+$ calc'd for $C_{23}H_{22}FN_3O_3$, 408.17; found 408.

Step B: 4-((7-Fluoro-1-(tetrahydro-2H-pyran-2-yl)pyrazolo[4,3-b]indol-4(1H)-yl)methyl)benzoic acid

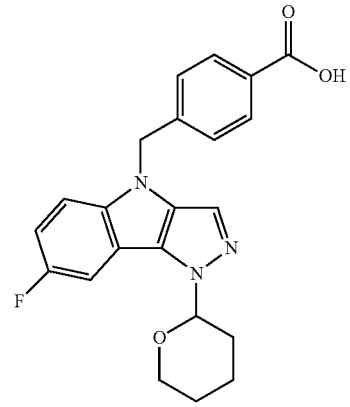 [SMILES: O=C(O)c1ccc(Cn2c3ccc(F)cc3c3c2cnn3C2CCCCO2)cc1]

To the solution of methyl 4-((7-fluoro-1-(tetrahydro-2H-pyran-2-yl)pyrazolo[4,3-b]indol-4(1H)-yl)methyl)benzoate (150 mg, 0.37 mmol) in MeOH (4 mL) and water (4 mL) was added KOH (82 mg, 4.0 eq) and the reaction mixture was heated at 60° C. for 3 hours. After cooling the mixture to room temperature, saturated aqueous NH$_4$Cl (10 mL) was added, and the reaction mixture was extracted into EtOAc (3×10 mL), washed with brine, dried over anhydrous Na$_2$SO$_4$, and concentrated to give the title compound as a solid (120 mg, 83%). MS [M+H]$^+$ calc'd for $C_{22}H_{20}FN_3O_3$, 394.16; found 394.

Step C: 4-((7-Fluoro-1-(tetrahydro-2H-pyran-2-yl)pyrazolo[4,3-b]indol-4(1H)-yl)methyl)-N-(2-hydroxyethyl)benzamide

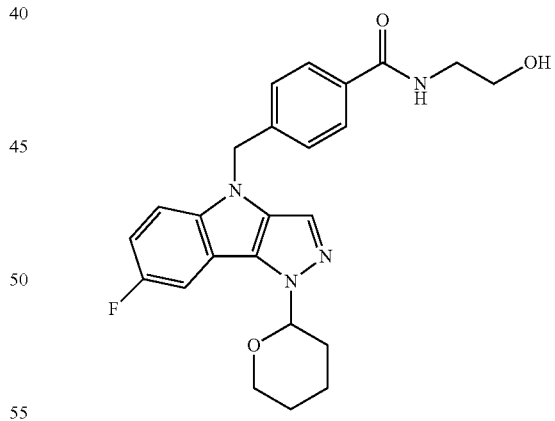

The title compound was prepared by a method similar to STEP B of EXAMPLE 50, using 4-((7-fluoro-1-(tetrahydro-2H-pyran-2-yl)pyrazolo[4,3-b]indol-4(1H)-yl)methyl)benzoic acid in place of 4-(7-fluoro-1-(tetrahydro-2H-pyran-2-yl)pyrazolo[4,3-b]indol-4(1H)-yl)benzoic acid.

Step D: 4-((7-Fluoropyrazolo[4,3-b]indol-4(1H)-yl)methyl)-N-(2-hydroxyethyl)benzamide The THP protecting group of 4-((7-fluoro-1-(tetrahydro-2H-pyran-2-yl)pyrazolo[4,3-b]indol-4(1H)-yl)methyl)-N-

(2-hydroxyethyl)benzamide was removed by a method similar to STEP D of EXAMPLE 52 to give the title compound. $^1$HNMR (400 MHz, DMSO-$d_6$) δ 13.02 (s, 1H), 8.38 (s, 1H), 7.77-7.75 (d, 2H, J=8.4 Hz), 7.56-7.48 (m, 3H), 7.31-7.29 (d, 2H, J=8.0 Hz), 7.15-7.13 (m, 1H), 5.47-5.39 (br s, 2H), 4.71 (s, 1H), 3.49-3.44 (m, 2H), 3.30-3.26 (m, 2H). [M+H]$^+$ calc'd for $C_{19}H_{17}FN_4O_2$, 353.14; found 353.2.

Example 55

(S)-1-(5-(7-Fluoropyrazolo[4,3-b]indol-4(1H)-yl)-4-methylpyrimidin-2-yl)pyrrolidin-3-ol

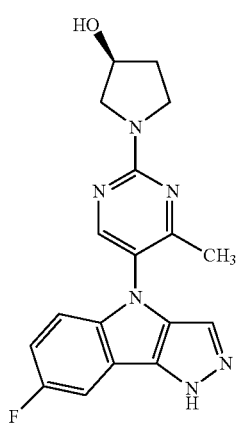 [SMILES: Cc1nc(N2CC[C@H](O)C2)ncc1-n1c2ccc(F)cc2c2[nH]ncc21]

Step A: (3S)-1-(5-(7-Fluoro-1-(tetrahydro-2H-pyran-2-yl)pyrazolo[4,3-b]indol-4(1H)-yl)-4-methylpyrimidin-2-yl)pyrrolidin-3-ol

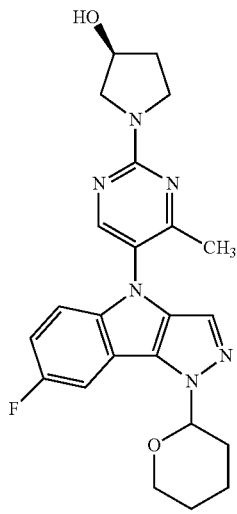 [SMILES: Cc1nc(N2CC[C@H](O)C2)ncc1-n1c2ccc(F)cc2c2c1cnn2C1CCCCO1]

7-Fluoro-1-(tetrahydro-2H-pyran-2-yl)-1,4-dihydropyrazolo[4,3-b]indole (60 mg, 0.231 mmol), (S)-1-(5-bromo-4-methylpyrimidin-2-yl)pyrrolidin-3-ol (131 mg, 0.509 mmol), copper(I) iodide (4.41 mg, 0.023 mmol), Cs$_2$CO$_3$ (226 mg, 0.694 mmol) and DMF (1 mL) were mixed in an 8 mL tube equipped with a magnetic stir bar to give a brown suspension. The solvent was purged with N$_2$, the tube sealed, and the reaction mixture heated in a sand bath for 72 hours at 180° C. The reaction mixture was subsequently partitioned between water (20 mL) and EtOAc (20 mL). The layers were separated and the aqueous layer was back-extracted with EtOAc (20 mL). The combined organic layers were concentrated to yield a dark syrup which was purified via flash chromatography (4 g column), eluting with 0-20% EtOAc in heptanes. The pure fractions were combined and concentrated to yield the title compound as a white solid.

Step B: (S)-1-(5-(7-Fluoropyrazolo[4,3-b]indol-4 (1H)-yl)-4-methylpyrimidin-2-yl)pyrrolidin-3-ol (3S)-1-(5-(7-Fluoro-1-(tetrahydro-2H-pyran-2-yl)pyrazolo[4,3-b]indol-4(1H)-yl)-4-methylpyrimidin-2-yl)pyrrolidin-3-ol was dissolved in MeOH (3 mL), treated with concentrated HCl (3 drops), and the reaction mixture was stirred overnight. The product was purified by preparative HPLC, eluting with 20-45% ACN in water (containing 0.05% TFA). The pure fractions were lyophilized to give a TFA salt of the title compound as a pale yellow solid (5 mg, 5%). $^1$H NMR (400 MHz, DMSO-$d_6$) δ ppm 1.94 (br s, 1 H), 1.98 (s, 3 H), 2.00-2.08 (m, 1 H), 3.58-3.68 (m, 5 H), 4.41 (br s, 2 H), 7.06 (br s, 1 H), 7.09-7.17 (m, 1 H), 7.59 (s, 1 H), 7.64 (dd, J=8.97, 2.65 Hz, 1 H), 8.35 (s, 1 H). [M+H]$^+$ calc'd for $C_{18}H_{17}FN_6O$, 353.37; found 353.3.

Example 56

1-(5-(7-Fluoropyrazolo[4,3-b]indol-4(1H)-yl)-4-methylpyrimidin-2-yl)piperidine-4-carbonitrile

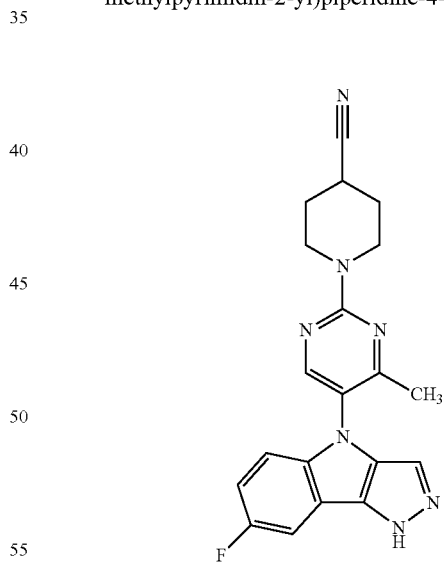

A TFA salt of the title compound was prepared by a method similar to EXAMPLE 55, using 1-(5-bromo-4-methylpyrimidin-2-yl)piperidine-4-carbonitrile in place of (S)-1-(5-bromo-4-methylpyrimidin-2-yl)pyrrolidin-3-ol. $^1$H NMR (400 MHz, DMSO-$d_6$) δ ppm 1.72-1.81 (m, 2 H), 1.97 (dt, J=6.38, 3.25 Hz, 2 H), 2.00 (s, 3 H), 3.19 (dt, J=8.59, 4.55 Hz, 2 H), 3.58-3.66 (m, 4 H), 4.12-4.20 (m, 5 H), 7.05-7.10 (m, 1 H), 7.11-7.17 (m, 1 H), 7.61 (s, 1 H), 7.64 (dd, J=9.09, 2.53 Hz, 1 H), 8.39 (s, 1 H). MS [M+H]$^+$ calc'd for $C_{20}H_{18}FN_7$, 376.17; found 376.3.

Example 57

7-Fluoro-4-(2-(4-fluoropiperidin-1-yl)-4-methylpyrimidin-5-yl)-1,4-dihydropyrazolo[4,3-b]indole

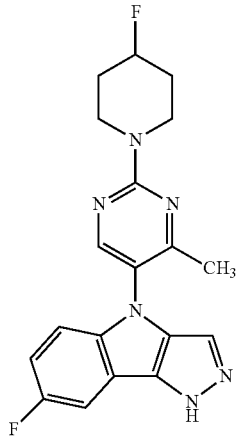 [SMILES: Cc1nc(N2CCC(F)CC2)ncc1-n1c2ccc(F)cc2c2[nH]ncc21]

A TFA salt of the title compound was prepared by a method similar to EXAMPLE 55, using 5-bromo-2-(4-fluoropiperidin-1-yl)-4-methylpyrimidine in place of (S)-1-(5-bromo-4-methylpyrimidin-2-yl)pyrrolidin-3-ol. $^1$H NMR (400 MHz, DMSO-$d_6$) δ ppm 1.76 (dd, J=6.95, 2.91 Hz, 2 H), 1.93 (br s, 1 H), 2.00 (s, 3 H), 3.79-3.86 (m, 2 H), 4.00 (br s, 2 H), 4.90 (br s, 2 H), 4.96-5.05 (m, 2 H), 7.06-7.16 (m, 2 H), 7.61-7.66 (m, 2 H), 8.38 (s, 1 H). MS [M+H]$^+$ calc'd for $C_{19}H_{18}F_2N_6$, 369.16; found 369.3.

Example 58

(3R)-1-(5-(7-Fluoropyrazolo[4,3-b]indol-4(1H)-yl)-4-methylpyrimidin-2-yl)pyrrolidin-3-ol

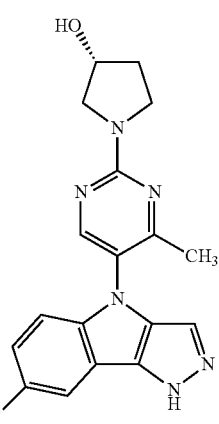

A TFA salt of the title compound was prepared by a method similar to EXAMPLE 55, using (R)-1-(5-bromo-4-methylpyrimidin-2-yl)pyrrolidin-3-ol in place of (S)-1-(5-bromo-4-methylpyrimidin-2-yl)pyrrolidin-3-ol. $^1$H NMR (400 MHz, DMSO-$d_6$) δ ppm 1.95 (br s, 1 H), 1.97 (s, 3 H), 2.01-2.08 (m, 1 H), 3.57-3.65 (m, 4 H), 4.41 (br s, 2 H), 7.05 (br s, 1 H), 7.13 (td, J=9.09, 2.78 Hz, 1 H), 7.59 (s, 1 H), 7.64 (dd, J=9.22, 2.40 Hz, 1 H), 8.35 (s, 1 H). MS [M+H]$^+$ calc'd for $C_{18}H_{17}FN_6O$, 353.15; found 353.3.

Example 59

(1-(5-(7-Fluoropyrazolo[4,3-b]indol-4(1H)-yl)-4-methylpyrimidin-2-yl)piperidin-4-yl)methanol

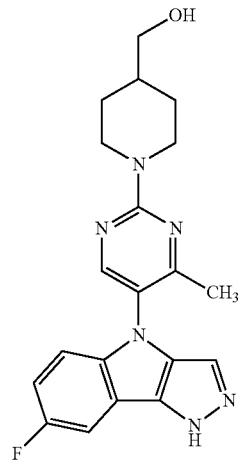 [SMILES: Cc1nc(N2CCC(CO)CC2)ncc1-n1c2ccc(F)cc2c2[nH]ncc21]

A TFA salt of the title compound was prepared by a method similar to EXAMPLE 55, using (1-(5-bromo-4-methylpyrimidin-2-yl)piperidin-4-yl)methanol in place of (S)-1-(5-bromo-4-methylpyrimidin-2-yl)pyrrolidin-3-ol. $^1$H NMR (400 MHz, DMSO-$d_6$) δ ppm 1.10-1.17 (m, 1 H), 1.25 (dd, J=12.13, 3.79 Hz, 1 H), 1.74-1.83 (m, 3 H), 1.98 (d, J=3.79 Hz, 3 H), 2.88-3.01 (m, 3 H), 3.31 (d, J=6.06 Hz, 1 H), 4.33 (d, J=6.57 Hz, 1 H), 4.78 (t, J=12.38 Hz, 4 H), 7.05-7.09 (m, 1 H), 7.10-7.16 (m, 1 H), 7.61 (d, J=2.27 Hz, 1 H), 7.64 (dd, J=9.09, 2.27 Hz, 1 H), 8.35 (d, J=9.35 Hz, 1 H). MS [M+H]$^+$ calc'd for $C_{20}H_{21}FN_6O$, 381.18; found 381.3.

Example 60

7-Fluoro-4-(4-methyl-2-(4-methylpiperazin-1-yl)pyrimidin-5-yl)-1,4-dihydropyrazolo[4,3-b]indole

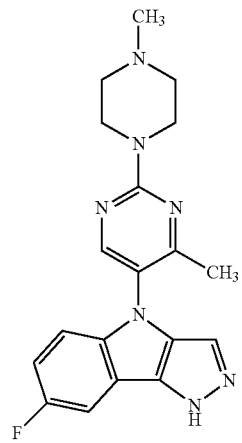 [SMILES: Cc1nc(N2CCN(C)CC2)ncc1-n1c2ccc(F)cc2c2[nH]ncc21]

7-Fluoro-1-(tetrahydro-2H-pyran-2-yl)-1,4-dihydropyrazolo[4,3-b]indole (40 mg, 0.154 mmol), 5-bromo-4-methyl-2-(4-methylpiperazin-1-yl)pyrimidine (71.1 mg, 0.262 mmol), copper(I) iodide (2.94 mg, 0.015 mmol), $Cs_2CO_3$ (151 mg, 0.463 mmol) and DMF (1 mL) were mixed in an 8 mL tube equipped with a magnetic stir bar to give a brown suspension. The tube was sealed and heated in a microwave for 60 minutes at 220° C. The reaction mixture was partitioned between water (25 mL) and EtOAc (50 mL). The layers were separated. The organic layer was washed with brine (20 mL), dried over Na$_2$SO$_4$, filtered, and concentrated to yield a brown syrup. The residue was dissolved in MeOH (5 mL), treated with concentrated HCl (4 drops) and stirred overnight. The product was purified by preparative HPLC, eluting with 20-45% ACN in water (containing 0.05% TFA). The fractions were not of satisfactory purity, so the solvent was evaporated and the residue was purified by preparative HPLC, eluting with 30-65% ACN in water (containing 10 mM NH$_4$HCO$_3$). The pure fractions were lyophilized to give the title compound as a white solid (7.8 mg, 14%). $^1$H NMR (400 MHz, DMSO-d$_6$) δ ppm 1.99 (s, 3 H), 2.24 (s, 3 H), 2.40 (t, J=5.05 Hz, 4 H), 3.81 (br s, 4 H), 7.14 (br s, 1 H), 7.51 (br s, 1 H), 7.68 (br s, 2 H), 8.37 (s, 1 H). MS [M+H]$^+$ calc'd for C$_{19}$H$_{20}$FN$_7$, 366.18; found 366.4.

Example 61

7-Fluoro-4-(2-methylpyridin-3-yl)-1,4-dihydropyrazolo[4,3-b]indole

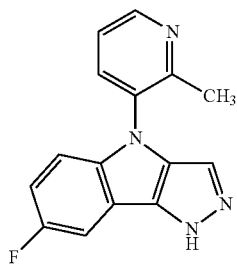 [SMILES: Cc1ncccc1-n1c2ccc(F)cc2c2[nH]ncc21]

The title compound was prepared by a method similar to EXAMPLE 60, using 3-bromo-2-methylpyridine in place of 5-bromo-4-methyl-2-(4-methylpiperazin-1-yl)pyrimidine.
1H NMR (400 MHz, DMSO-d$_6$) δ ppm 2.33 (s, 3 H), 7.08-7.11 (m, 1 H), 7.14-7.21 (m, 1 H), 7.58 (dd, J=7.96, 4.93 Hz, 1 H), 7.65 (s, 1 H), 7.69 (dd, J=8.97, 2.40 Hz, 1 H), 8.06 (dd, J=7.96, 1.39 Hz, 1 H), 8.68 (dd, J=5.05, 1.52 Hz, 1 H). MS [M+H]$^+$ calc'd for C$_{15}$H$_{11}$FN$_4$, 267.10; found 267.2.

Example 62

7-Fluoro-4-(1,3,5-trimethyl-1H-pyrazol-4-yl)-1,4-dihydropyrazolo[4,3-b]indole

7-Fluoro-1-(tetrahydro-2H-pyran-2-yl)-1,4-dihydropyrazolo[4,3-b]indole (40 mg, 0.154 mmol), 4-bromo-1,3,5-trimethyl-1H-pyrazole (29.2 mg, 0.154 mmol), copper(I) iodide (2.94 mg, 0.015 mmol), Cs$_2$CO$_3$ (151 mg, 0.463 mmol) and DMF (1 mL) were mixed in an 8 mL tube equipped with a magnetic stir bar to give a brown suspension. The solvent was purged with N$_2$ and the tube was sealed and heated in a microwave for 60 minutes at 22° C. More 4-bromo-1,3,5-trimethyl-1H-pyrazole (29.2 mg, 0.154 mmol), copper(I) iodide (2.94 mg, 0.015 mmol) and Cs$_2$CO$_3$ (151 mg, 0.463 mmol) were added and the mixture was heated for an additional hour. The reaction mixture was subsequently partitioned between water (25 mL) and EtOAc (50 mL). The layers were separated. The organic layer was washed with brine (20 mL), dried over Na$_2$SO$_4$, filtered, and concentrated to yield a brown syrup. The residue was dissolved in MeOH (5 mL) and treated with concentrated HCl (4 drops). The reaction mixture was stirred overnight and the product was purified by preparative HPLC, eluting with 25-50% ACN in water (containing 0.05% TFA). The pure fractions were lyophilized to give a TFA salt of the title compound as a clear glass (7.8 mg, 13%). $^1$H NMR (400 MHz, DMSO-d$_6$) δ ppm 1.88 (s, 3 H), 2.02 (s, 3 H), 3.76 (s, 4 H), 6.95-6.99 (m, 2 H), 7.13 (td, J=9.16, 2.65 Hz, 1 H), 7.52 (s, 1 H), 7.61 (dd, J=8.97, 2.40 Hz, 1 H). MS [M+H]$^+$ calc'd for C$_{15}$H$_{14}$FN$_5$, 284.13; found 284.2.

Example 63

2-((5-(7-Fluoropyrazolo[4,3-b]indol-4(1H)-yl)-4-methylpyridin-2-yl)(methyl)amino)ethanol A TFA salt of the title compound was prepared by a method similar to EXAMPLE 62, using 2-((5-bromo-4-methylpyridin-2-yl)(methyl)amino)ethanol in place of 4-bromo-1,3,5-trimethyl-1H-pyrazole. $^1$H NMR (400 MHz, CD$_3$OD) δ ppm 2.08 (d, J=0.76 Hz, 3 H), 3.36 (s, 3 H), 3.83-3.87 (m, 2 H), 3.88-3.93 (m, 2 H), 7.09-7.18 (m, 2 H), 7.36 (s, 1 H), 7.52 (s, 1 H), 7.63 (dd, J=8.59, 2.27 Hz, 1 H), 8.10 (s, 1 H). MS [M+H]$^+$ calc'd for C$_{18}$H$_{18}$FN$_5$O, 340.16; found 340.3.

Example 64

7-Fluoro-4-(2-methyl-6-(piperazin-1-yl)pyridin-3-yl)-1,4-dihydropyrazolo[4,3-b]indole

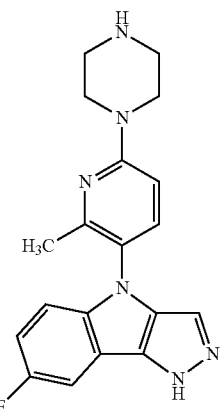

A TFA salt of the title compound was prepared by a method similar to EXAMPLE 62, using 1-(5-bromo-6-methylpyridin-2-yl)piperazine hydrochloride in place of 4-bromo-1,3,5-trimethyl-1H-pyrazole. $^1$H NMR (400 MHz, CD$_3$OD) δ ppm 2.12 (s, 3 H), 3.34-3.39 (m, 4 H), 3.90-3.94 (m, 4 H), 6.92 (d, J=9.09 Hz, 1 H), 6.94-6.97 (m, 1 H), 7.11 (td, J=9.09, 2.53 Hz, 1 H), 7.41 (s, 1 H), 7.59-7.64 (m, 2 H). MS [M+H]$^+$ calc'd for C$_{19}$H$_{19}$FN$_6$, 351.17; found 351.3.

Example 65

7-Fluoro-4-(5-(methoxymethyl)-1H-pyrazol-4-yl)-1,4-dihydropyrazolo[4,3-b]indole

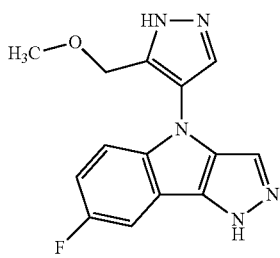 [SMILES: COCc1[nH]ncc1-n1c2ccc(F)cc2c2[nH]ncc21]

Step A: Methyl 4-bromo-1-((2-(trimethylsilyl)ethoxy)methyl)-1H-pyrazole-5-carboxylate

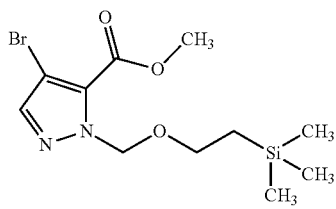 [SMILES: COC(=O)c1c(Br)cnn1COCC[Si](C)(C)C]

To a solution of methyl 4-bromo-1H-pyrazole-5-carboxylate (4.53 g, 204 mmol, 1.0 eq) in DMF (50 mL) was added NaH (60% wt, 1.33 g, 1.5 eq) at 0° C. The mixture was stirred at 0° C. for 30 minutes, which was followed by the dropwise addition of (2-(chloromethoxy)ethyl)trimethylsilane (4.44 g, 1.2 eq). The reaction mixture was allowed to warm to room temperature and was stirred overnight. The solution was concentrated, diluted with water (10 mL), and extracted into EtOAc (3×20 mL). The organic layer was dried over Na$_2$SO$_4$, filtered, concentrated, and purified by flash column chromatography, eluting with petroleum ether/EtOAc (20:1) to obtain the title compound as an oil (6.2 g, 84%). MS [M+H]$^+$ calc'd for C$_{11}$H$_{19}$BrN$_2$O$_3$Si, 335.04; found 335.

Step B: (4-Bromo-1-((2-(trimethylsilyl)ethoxy)methyl)-1H-pyrazol-5-yl)methanol

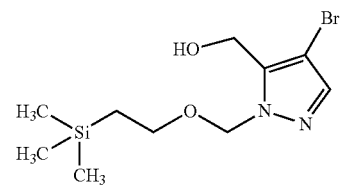 [SMILES: C[Si](C)(C)CCOCn1ncc(Br)c1CO]

To a solution of methyl 4-bromo-1-((2-(trimethylsilyl)ethoxy)methyl)-1H-pyrazole-5-carboxylate (5.6 g, 334 mmol, 1.0 eq) in dry THF (50 mL) was added LiAlH$_4$ (2.4N, 3.5 mL, 0.5 eq) at −78° C. The reaction mixture was stirred at −78° C. for 20 minutes and was then allowed to warm to room temperature over a 20 minute period. The reaction was subsequently quenched by the dropwise addition of water (5 mL). The solid was filtered off and the filtrate was concentrated to give the title compound as an oil, which was used without further purification (4.2 g, 82%). MS [M+H]$^+$ calc'd for C$_{10}$H$_{19}$BrN$_2$O$_2$Si, 307.05; found 307.

Step C: 4-Bromo-5-(methoxymethyl)-1-((2-(trimethylsilyl)ethoxy)methyl)-1H-pyrazole

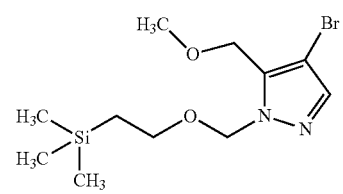 [SMILES: COCc1c(Br)cnn1COCC[Si](C)(C)C]

To a solution of (4-bromo-1-((2-(trimethylsilyl)ethoxy)methyl)-1H-pyrazol-5-yl)methanol (4.0 g crude, 13.07 mmol, 1.0 eq) in dry THF (50 mL) was added NaH (60% wt, 0.78 g, 1.5 eq) at 0° C. The mixture was stirred at 0° C. for 30 minutes. Iodomethane (2.78 g, 1.5 eq) was then added dropwise, and the reaction mixture was allowed to warm to room temperature, with stirring, over a period of 3 hours. The mixture was subsequently concentrated, diluted with water (10 mL), and extracted into EtOAc (3×20 mL). The organic layer was dried over $Na_2SO_4$, filtered, concentrated, and purified by flash column chromatography, eluting with petroleum ether/EtOAc (40:1) to give the title compound as an oil (2.0 g, 48%). $^1$HNMR: (300 MHz, $CDCl_3$) δ ppm 7.47 (s, 1H), 5.52 (s, 2H), 4.57 (s, 2H), 3.59-3.53 (t, 2H, J=8.1 Hz), 3.35 (s, 3H), 0.93-0.87 (t, 2H, J=7.8 Hz), 0.00 (s, 9H).

Step D: 7-Fluoro-4-(5-(methoxymethyl)-1-((2-(trimethylsilyl)ethoxy)methyl)-1H-pyrazol-4-yl)-1-(tetrahydro-2H-pyran-2-yl)-1,4-dihydropyrazolo[4,3-b]indole

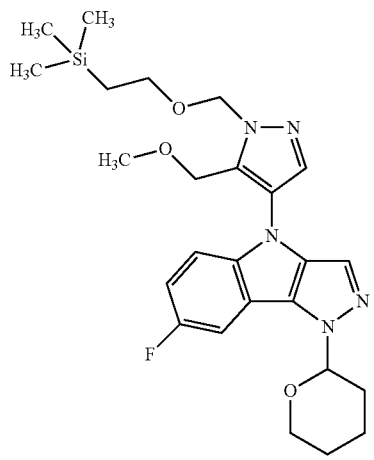 [SMILES: COCc1c(-n2c3ccc(F)cc3c3c2cnn3C2CCCCO2)cnn1COCC[Si](C)(C)C]

A mixture of 7-fluoro-1-(tetrahydro-2H-pyran-2-yl)-1,4-dihydropyrazolo[4,3-b]indole (200 mg, 0.77 mmol, 1.0 eq), 4-bromo-5-(methoxymethyl)-1-((2-(trimethylsilyl)ethoxy)methyl)-1H-pyrazole (246 mg, 1.0 eq), CuI (196 mg, 2 eq), and $Cs_2CO_3$ (754 mg, 3 eq) in DMA (6 mL) was heated at 145° C. under nitrogen for 16 hours. The reaction mixture was then diluted with water (6 mL), extracted into EtOAc (3×15 mL), and washed with brine. The organic layer was dried over $Na_2SO_4$, filtered, concentrated, and purified by flash column chromatography, eluting with a gradient of petroleum ether/EtOAc (20:1 to 5:1) to give the title compound (60 mg, 9.6%). MS $[M+H]^+$ calc'd for $C_{25}H_{34}FN_5O_3Si$, 500.25; found 500.

Step E: 7-Fluoro-4-(5-(methoxymethyl)-1H-pyrazol-4-yl)-1,4-dihydropyrazolo[4,3-b]indole To a solution of 7-fluoro-4-(5-(methoxymethyl)-1-((2-(trimethylsilyl)ethoxy)methyl)-1H-pyrazol-4-yl)-1-(tetrahydro-2H-pyran-2-yl)-1,4-dihydropyrazolo[4,3-b]indole (60 mg) in ethanol (4 mL) was added concentrated aqueous HCl (2 mL). The solution was stirred at 40° C. for 3 hours. The reaction mixture was subsequently concentrated, washed with petroleum ether, and dried to obtain the title compound as a solid (30 mg, 87%). $^1$HNMR (400 MHz, DMSO-$d_6$) δ ppm 8.00 (s, 1H), 7.63-7.60 (m, 2H), 7.21-7.15 (m, 2H), 4.28 (s, 2H), 3.07 (s, 3H). MS $[M+H]^+$ calc'd for $C_{14}H_{12}FN_5O$, 286.11; found 286.1.

Example 66

4-(5-(7-Fluoropyrazolo[4,3-b]indol-4(1H)-yl)-6-methylpyridin-2-yl)morpholine

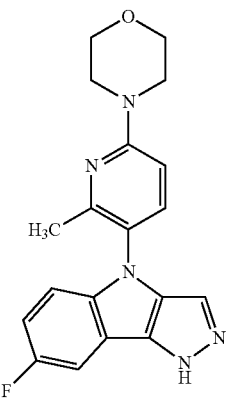 [SMILES: Cc1nc(N2CCOCC2)ccc1-n1c2ccc(F)cc2c2[nH]ncc21]

7-Fluoro-1-(tetrahydro-2H-pyran-2-yl)-1,4-dihydropyrazolo[4,3-b]indole (60 mg, 0.231 mmol), 4-(5-bromo-6-methylpyridin-2-yl)morpholine (101 mg, 0.393 mmol), ((thiophene-2-carbonyl)oxy)copper (4.41 mg, 0.023 mmol), $Cs_2CO_3$ (226 mg, 0.694 mmol) and DMF (1.5 mL) were mixed in an 8 mL tube equipped with a magnetic stir bar to give a brown suspension. The solvent was purged with $N_2$, the tube was sealed, and the reaction mixture was heated at 180° C. for 48 hours in a sand bath. The reaction was subsequently partitioned between water (20 mL) and EtOAc (20 mL) and the layers were separated. The aqueous layer was back-extracted with EtOAc (20 mL) and the combined organic layers were concentrated to yield a dark syrup. The residue was dissolved in MeOH (3 mL), treated with concentrated HCl (3 drops), and stirred overnight. The product was purified by preparative HPLC, eluting with 35-60% ACN in aqueous 10 mM $NH_4HCO_3$. The pure fractions were lyophilized to give the title compound as a white solid (8.2 mg, 10%). $^1$H NMR (400 MHz, DMSO-$d_6$) δ ppm 2.04 (s, 3 H), 3.51-3.55 (m, 4 H), 3.73 (t, J=4.80 Hz, 4 H), 6.82 (d, J=9.35 Hz, 1 H), 7.13 (td, J=9.22, 3.03 Hz, 2 H), 7.57 (d, J=8.84 Hz, 2 H). MS $[M+H]^+$ calc'd for $C_{19}H_{18}FN_5O$, 352.16; found 352.3.

Example 67

6-(7-Fluoropyrazolo[4,3-b]indol-4(1H)-yl)-1-(2-hydroxyethyl)-5-methyl-1H-imidazo[4,5-b]pyridin-2(3H)-one

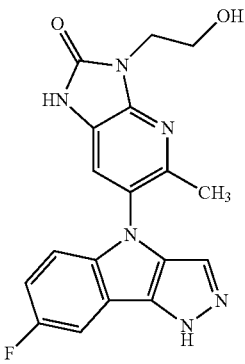 [SMILES: Cc1nc2c(cc1-n1c3ccc(F)cc3c3[nH]ncc31)[nH]c(=O)n2CCO]

The title compound was prepared by a method similar to EXAMPLE 66, using 6-bromo-3-(2-hydroxyethyl)-5-methyl-1H-imidazo[4,5-b]pyridin-2(3 H)-one in place of 4-(5-bromo-6-methylpyridin-2-yl)morpholine. $^1$H NMR (400 MHz, CD$_3$OD) δ ppm 2.16-2.23 (m, 3 H), 3.90-3.99 (m, 2 H), 4.11-4.21 (m, 2 H), 6.95-7.05 (m, 1 H), 7.15 (td, J=9.09, 2.53 Hz, 1 H), 7.33-7.41 (m, 1 H), 7.52-7.59 (m, 1 H), 7.64 (dd, J=8.84, 2.53 Hz, 1 H). MS [M+H]$^+$ calc'd for C$_{18}$H$_{15}$FN$_6$O$_2$, 367.13; found 367.3.

Example 68

5-(7-Fluoropyrazolo[4,3-b]indol-4(1H)-yl)-3,4-dimethylpyridin-2-amine

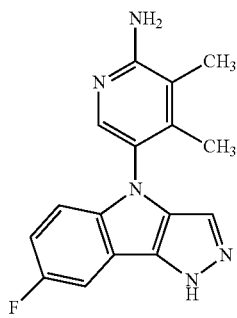 [SMILES: Cc1c(-n2c3ccc(F)cc3c3[nH]ncc32)cnc(N)c1C]

The title compound was prepared by a method similar to EXAMPLE 66, using 5-bromo-3,4-dimethylpyridin-2-amine in place of 4-(5-bromo-6-methylpyridin-2-yl)morpholine. $^1$H NMR (400 MHz, DMSO-d$_6$) δ ppm 1.76 (s, 3 H), 2.06 (s, 3 H), 5.97 (br s, 2 H), 6.54 (s, 1 H), 7.11 (td, J=9.16, 2.65 Hz, 1 H), 7.56 (br s, 1 H), 7.83 (s, 1 H). MS [M+H]$^+$ calc'd for C$_{16}$H$_{14}$FN$_5$, 296.13; found 296.2.

Example 69

7-Fluoro-4-(6-methoxy-2-methylpyridin-3-yl)-1,4-dihydropyrazolo[4,3-b]indole

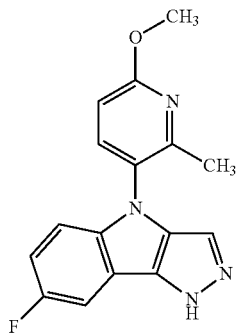 [SMILES: COc1ccc(-n2c3ccc(F)cc3c3[nH]ncc32)c(C)n1]

The title compound was prepared by a method similar to EXAMPLE 66, using 3-bromo-6-methoxy-2-methylpyridine in place of 4-(5-bromo-6-methylpyridin-2-yl)morpholine. $^1$H NMR (400 MHz, CD$_3$OD) δ ppm 2.16 (s, 3 H), 3.96-4.00 (m, 3 H), 6.80 (d, J=8.59 Hz, 1 H), 6.96 (br s, 1 H), 7.10 (td, J=9.09, 2.53 Hz, 1 H), 7.37-7.48 (m, 1 H), 7.55-7.68 (m, 2 H). MS [M+H]$^+$ calc'd for C$_{16}$H$_{13}$FN$_4$O, 297.12; found 297.2.

Example 70

7-Fluoro-4-(5-methyl-[1,2,4]triazolo[1,5-a]pyridin-6-yl)-1,4-dihydropyrazolo[4,3-b]indole

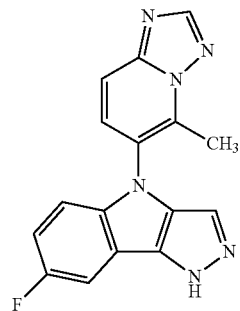 [SMILES: Cc1c(-n2c3ccc(F)cc3c3[nH]ncc32)ccc2ncnn12]

The title compound was prepared by a method similar to EXAMPLE 66, using 6-bromo-5-methyl-[1,2,4]triazolo[1,5-a]pyridine in place of 4-(5-bromo-6-methylpyridin-2-yl)morpholine. $^1$H NMR (400 MHz, DMSO-d$_6$) δ ppm 2.57 (br s, 3 H), 7.16-7.19 (m, 2 H), 7.76 (d, J=9.35 Hz, 2 H), 7.87 (s, 1 H), 8.67 (s, 1 H). MS [M+H]$^+$ calc'd for C$_{16}$H$_{11}$FN$_6$, 307.11; found 307.2.

Example 71

7-Fluoro-4-(4-methyl-1H-indazol-5-yl)-1,4-dihydropyrazolo[4,3-b]indole

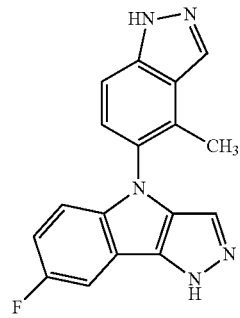 [SMILES: Cc1c(-n2c3ccc(F)cc3c3[nH]ncc32)ccc2[nH]ncc12]

The title compound was prepared by a method similar to EXAMPLE 66, using 5-bromo-4-methyl-1H-indazole in place of 4-(5-bromo-6-methylpyridin-2-yl)morpholine. $^1$H NMR (400 MHz, DMSO-d$_6$) δ ppm 2.28 (s, 3 H), 6.94-6.98 (m, 1 H), 7.08-7.15 (m, 2 H), 7.30 (d, J=8.84 Hz, 1 H), 7.51-7.54 (m, 2 H), 7.65 (d, J=9.60 Hz, 1 H), 8.28 (s, 1 H). MS [M+H]$^+$ calc'd for C$_{17}$H$_{12}$FN$_5$, 306.12; found 306.2.

Example 72

(2S)-1-(5-(7-Fluoropyrazolo[4,3-b]indol-4(1H)-yl)-4-methylpyrimidin-2-yl)pyrrolidine-2-carboxamide

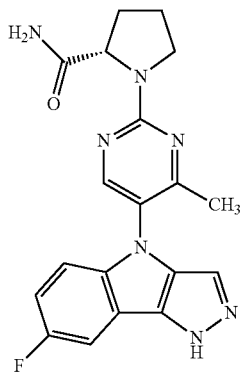

The title compound was prepared by a method similar to EXAMPLE 66, using (S)-1-(5-bromo-4-methylpyrimidin-2-yl)pyrrolidine-2-carboxamide in place of 4-(5-bromo-6-methylpyridin-2-yl)morpholine. $^1$H NMR (400 MHz, CD$_3$OD) δ ppm 2.04-2.23 (m, 6 H), 2.23-2.44 (m, 1 H), 3.59-3.81 (m, 1 H), 3.81-3.93 (m, 1 H), 4.59 (dd, J=8.84, 3.28 Hz, 1 H), 6.99 (dd, J=8.84, 3.79 Hz, 1 H), 7.10 (td, J=9.09, 2.78 Hz, 1 H), 7.44 (s, 1 H), 7.60 (d, J=8.08 Hz, 1 H), 8.29 (s, 1 H). MS [M+H]$^+$ calc'd for C$_{19}$H$_{18}$FN$_7$O, 380.16; found 380.17.

Example 73

(2R)-1-(5-(7-Fluoropyrazolo[4,3-b]indol-4(1H)-yl)-4-methylpyrimidin-2-yl)pyrrolidine-2-carboxamide

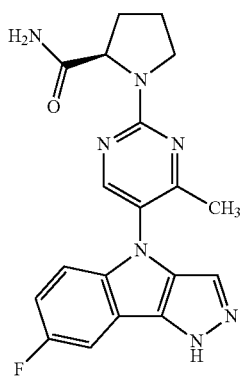 [SMILES: Cc1nc(N2CCC[C@@H]2C(N)=O)ncc1-n1c2ccc(F)cc2c2[nH]ncc21]

The title compound was prepared by a method similar to EXAMPLE 66, using (R)-1-(5-bromo-4-methylpyrimidin-2-yl)pyrrolidine-2-carboxamide in place of 4-(5-bromo-6-methylpyridin-2-yl)morpholine. $^1$H NMR (400 MHz, CD$_3$OD) δ ppm 2.02-2.22 (m, 6 H), 2.27-2.43 (m, 1 H), 3.63-3.79 (m, 1 H), 3.79-3.94 (m, 1 H), 4.59 (dd, J=8.59, 3.28 Hz, 1 H), 7.00 (br s, 1 H), 7.03-7.16 (m, 1 H), 7.44 (s, 1 H), 7.60 (br s, 1 H), 8.29 (s, 1 H). MS [M+H]$^+$ calc'd for C$_{19}$H$_{18}$FN$_7$O, 380.16; found 380.17.

Example 74

2-((5-(7-Fluoropyrazolo[4,3-b]indol-4(1H)-yl)-4-methylpyrimidin-2-yl)amino)ethanol

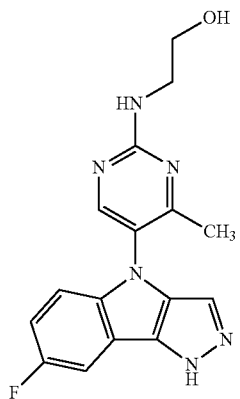 [SMILES: Cc1nc(NCCO)ncc1-n1c2ccc(F)cc2c2[nH]ncc21]

The title compound was prepared by a method similar to EXAMPLE 66, using 2-((5-bromo-4-methylpyrimidin-2-yl)amino)ethanol in place of 4-(5-bromo-6-methylpyridin-2-yl)morpholine. $^1$H NMR (400 MHz, CD$_3$OD) δ ppm 2.01 (s, 3 H), 3.59 (t, J=5.68 Hz, 2 H), 3.76 (t, J=5.81 Hz, 2 H), 7.00 (dd, J=8.97, 4.17 Hz, 1 H), 7.10 (td, J=9.09, 2.53 Hz, 1 H), 7.47 (s, 1 H), 7.60 (d, J=7.83 Hz, 1 H), 8.24 (s, 1 H). MS [M+H]$^+$ calc'd for C$_{16}$H$_{15}$FN$_6$O, 327.14; found 327.15.

Example 75

(2R)-2-((5-(7-Fluoropyrazolo[4,3-b]indol-4(1H)-yl)-4-methylpyrimidin-2-yl)amino)propan-1-ol

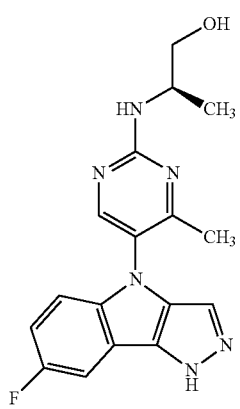 [SMILES: Cc1nc(N[C@H](C)CO)ncc1-n1c2ccc(F)cc2c2[nH]ncc21]

The title compound was prepared by a method similar to EXAMPLE 66, using (R)-2-((5-bromo-4-methylpyrimidin-2-yl)amino)propan-1-ol in place of 4-(5-bromo-6-methyl-pyridin-2-yl)morpholine. $^1$H NMR (400 MHz, CD$_3$OD) δ ppm 1.27 (d, J=6.82 Hz, 3 H), 2.01 (s, 3 H), 3.52-3.71 (m, 2 H), 4.20 (d, J=6.57 Hz, 1 H), 7.01 (dd, J=8.97, 4.17 Hz, 1 H), 7.11 (td, J=9.09, 2.53 Hz, 1 H), 7.47 (s, 1 H), 7.60 (d, J=6.82 Hz, 1 H), 8.23 (s, 1 H). MS [M+H]$^+$ calc'd for C$_{17}$H$_7$FN$_6$O, 341.15; found 341.16.

Example 76

(3R,4R)-1-(5-(7-Fluoropyrazolo[4,3-b]indol-4(1H)-yl)-4-methylpyrimidin-2-yl)pyrrolidine-3,4-diol

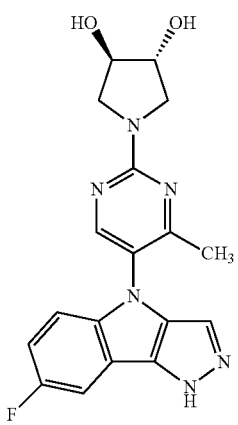 [SMILES: Cc1nc(N2C[C@@H](O)[C@H](O)C2)ncc1-n1c2ccc(F)cc2c2[nH]ncc21]

The title compound was prepared by a method similar to EXAMPLE 66, using (3R,4R)-1-(5-bromo-4-methylpyrimidin-2-yl)pyrrolidine-3,4-diol in place of 4-(5-bromo-6-methylpyridin-2-yl)morpholine. $^1$H NMR (400 MHz, CD$_3$OD) δ ppm 2.04 (s, 3 H), 3.70 (br s, 2 H), 3.83 (dd, J=12.25, 3.66 Hz, 2 H), 4.16-4.28 (m, 2 H), 6.99 (dd, J=8.84, 3.79 Hz, 1 H), 7.04-7.18 (m, 1 H), 7.40-7.53 (m, 1 H), 7.54-7.67 (m, 1 H), 8.24-8.30 (m, 1 H). MS [M+H]$^+$ calc'd for C$_{18}$H$_{17}$FN$_6$O$_2$, 369.15; found 369.16.

Example 77

((2R)-4-(5-(7-Fluoropyrazolo[4,3-b]indol-4(1H)-yl)-4-methylpyrimidin-2-yl)morpholin-2-yl)methanol

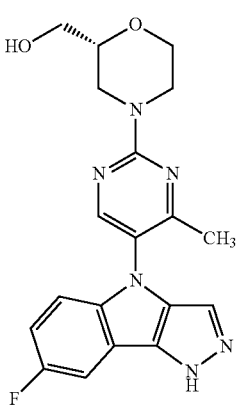 [SMILES: Cc1nc(N2CCO[C@@H](CO)C2)ncc1-n1c2ccc(F)cc2c2[nH]ncc21]

The title compound was prepared by a method similar to EXAMPLE 66, using (R)-(4-(5-bromo-4-methylpyrimidin-2-yl)morpholin-2-yl)methanol in place of 4-(5-bromo-6-methylpyridin-2-yl)morpholine. $^1$H NMR (400 MHz, CD$_3$OD) δ ppm 2.04 (s, 3 H), 2.88 (dd, J=13.14, 10.61 Hz, 1 H), 3.03-3.18 (m, 1 H), 3.50-3.71 (m, 4 H), 4.03 (dd, J=11.37, 2.27 Hz, 1 H), 4.62 (d, J=13.39 Hz, 1 H), 4.74 (d, J=12.88 Hz, 1 H), 6.91-7.06 (m, 1 H), 7.06-7.17 (m, 1 H), 7.46 (s, 1 H), 7.60 (br s, 1 H), 8.31 (s, 1 H). MS [M+H]$^+$ calc'd for C$_{19}$H$_{19}$FN$_6$O$_2$, 383.16; found 383.18.

Example 78

1-(5-(7-Fluoropyrazolo[4,3-b]indol-4(1H)-yl)-4-methylpyrimidin-2-yl)piperidin-4-ol

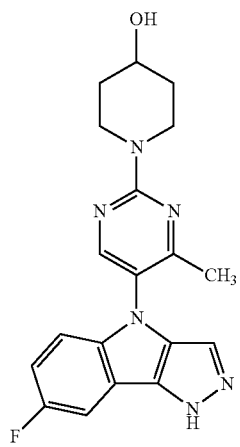 [SMILES: Cc1nc(N2CCC(O)CC2)ncc1-n1c2ccc(F)cc2c2[nH]ncc21]

The title compound was prepared by a method similar to EXAMPLE 66, using 1-(5-bromo-4-methylpyrimidin-2-yl)piperidin-4-ol in place of 4-(5-bromo-6-methylpyridin-2-yl)morpholine. 1H NMR (400 MHz, CD$_3$OD) δ ppm 1.44-1.59 (m, 2 H), 1.89-1.99 (m, 2 H), 2.00-2.05 (m, 3 H), 3.36 (ddd, J=13.39, 10.23, 3.16 Hz, 2 H), 3.90 (dt, J=8.84, 4.67 Hz, 1 H), 4.52 (dt, J=13.45, 4.39 Hz, 2 H), 6.94-7.04 (m, 1 H), 7.07-7.18 (m, 1 H), 7.47 (s, 1 H), 7.60 (d, J=7.58 Hz, 1 H), 8.26 (s, 1 H). MS [M+H]$^+$ calc'd for C$_{19}$H$_{19}$FN$_6$O, 367.17; found 367.2.

Example 79

(2S)-3-(6-(7-Fluoropyrazolo[4,3-b]indol-4(1H)-yl)-5-methyl-3H-imidazo[4,5-b]pyridin-3-yl)propane-1,2-diol

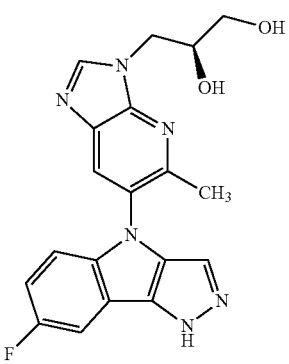 [SMILES: Cc1nc2c(cc1-n1c3ccc(F)cc3c3[nH]ncc31)ncn2C[C@H](O)CO]

The title compound was prepared by a method similar to EXAMPLE 66, using (S)-6-bromo-3-((2,2-dimethyl-1,3-dioxolan-4-yl)methyl)-5-methyl-3H-imidazo[4,5-b]pyridine in place of 4-(5-bromo-6-methylpyridin-2-yl)morpholine. 1H NMR (400 MHz, CD$_3$OD), δ ppm 2.31 (s, 3 H), 3.62 (dt, J=5.37, 1.74 Hz, 2 H), 4.06-4.19 (m, 1 H), 4.36 (ddd, J=14.15, 8.08, 1.77 Hz, 1 H), 4.58-4.66 (m, 1 H), 6.95 (d, J=4.04 Hz, 1 H), 7.06-7.13 (m, 1 H), 7.43 (d, J=8.59 Hz, 1 H), 7.57-7.70 (m, 1 H), 8.09 (s, 1 H). MS [M+H]$^+$ calc'd for $C_{19}H_{17}FN_6O_2$, 381.15; found 381.3.

Example 80

3-(6-(7-Fluoropyrazolo[4,3-b]indol-4(1H)-yl)-5-methyl-3H-imidazo[4,5-b]pyridin-3-yl)propan-1-ol

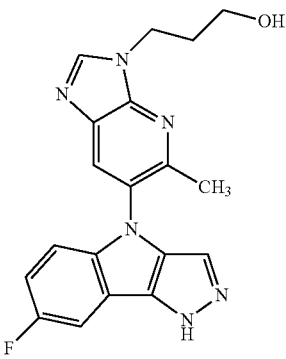 [SMILES: Cc1nc2c(cc1-n1c3ccc(F)cc3c3[nH]ncc31)ncn2CCCO]

The title compound was prepared by a method similar to EXAMPLE 66, using 3-(6-bromo-5-methyl-3H-imidazo[4,5-b]pyridin-3-yl)propan-1-ol in place of 4-(5-bromo-6-methylpyridin-2-yl)morpholine. $^1$H NMR (400 MHz, CD$_3$OD), δ ppm 2.19 (quin, J=6.51 Hz, 2 H), 2.31 (s, 3 H), 3.63 (t, J=6.06 Hz, 2 H), 4.53 (t, J=6.95 Hz, 2 H), 6.95 (dd, J=9.09, 4.04 Hz, 1 H), 7.09 (td, J=9.09, 2.53 Hz, 1 H), 7.44 (s, 1 H), 7.64 (d, J=7.07 Hz, 1 H), 8.08 (s, 1 H), 8.46 (s, 1 H). MS [M+H]$^+$ calc'd for $C_{19}H_{17}FN_6O$, 365.15; found 365.3.

Example 81

6-(7-Fluoropyrazolo[4,3-b]indol-4(1H)-yl)-3-(3-hydroxypropyl)-5-methyl-1H-imidazo[4,5-b]pyridin-2(3H)-one

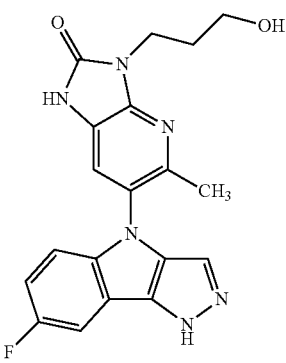 [SMILES: Cc1nc2c(cc1-n1c3ccc(F)cc3c3[nH]ncc31)[nH]c(=O)n2CCCO]

The title compound was prepared by a method similar to EXAMPLE 66, using 6-bromo-3-(3-hydroxypropyl)-5-methyl-1H-imidazo[4,5-b]pyridin-2(3 H)-one in place of 4-(5-bromo-6-methylpyridin-2-yl)morpholine. $^1$H NMR (400 MHz, CD$_3$OD), δ ppm 1.99-2.10 (m, 2 H), 2.21 (s, 3 H), 3.67 (t, J=6.32 Hz, 2 H), 4.12 (t, J=7.07 Hz, 2 H), 6.95-7.03 (m, 1 H), 7.06-7.14 (m, 1 H), 7.37 (s, 1 H), 7.45 (s, 1 H), 7.63 (br s, 1 H). MS [M+H]$^+$ calc'd for $C_{19}H_{17}FN_6O_2$, 381.15; found 381.3.

Example 82

2-(6-(7-Fluoropyrazolo[4,3-b]indol-4(1H)-yl)-5-methyl-3H-imidazo[4,5-b]pyridin-3-yl)ethanol

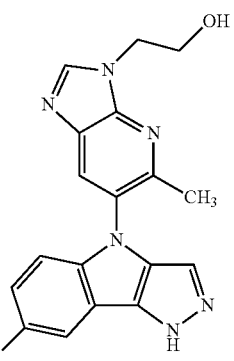

The title compound was prepared by a method similar to EXAMPLE 66, using 2-(6-bromo-5-methyl-3H-imidazo[4,5-b]pyridin-3-yl)ethanol in place of 4-(5-bromo-6-methylpyridin-2-yl)morpholine. $^1$H NMR (400 MHz, CD$_3$OD) δ ppm 2.31 (s, 3 H), 4.00 (t, J=5.31 Hz, 2 H), 4.51 (t, J=5.18 Hz, 2 H), 6.95 (dd, J=8.84, 4.29 Hz, 1 H), 7.10 (td, J=9.09, 2.53 Hz, 1 H), 7.43 (s, 1 H), 7.65 (br s, 1 H), 8.08 (s, 1 H), 8.45 (s, 1 H). MS [M+H]$^+$ calc'd for $C_{18}H_{15}FN_6O$, 351.14; found 351.3.

Example 83

((2S)-4-(5-(7-Fluoropyrazolo[4,3-b]indol-4(1H)-yl)-4-methylpyrimidin-2-yl)morpholin-2-yl)methanol

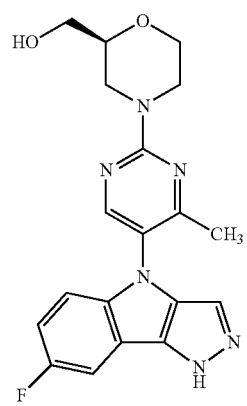 [SMILES: Cc1nc(N2CCO[C@H](CO)C2)ncc1-n1c2ccc(F)cc2c2[nH]ncc21]

The title compound was prepared by a method similar to EXAMPLE 66, using (S)-(4-(5-bromo-4-methylpyrimidin-2-yl)morpholin-2-yl)methanol in place of 4-(5-bromo-6-methylpyridin-2-yl)morpholine. $^1$H NMR (400 MHz, CD$_3$OD) δ ppm 2.04 (s, 3 H), 2.86 (dd, J=13.14, 10.61 Hz, 1 H), 3.00-3.15 (m, 1 H), 3.45-3.71 (m, 4 H), 3.95-4.06 (m, 1 H), 4.61 (d, J=13.39 Hz, 1 H), 4.73 (dd, J=13.01, 1.89 Hz, 1 H), 6.94-7.05 (m, 1 H), 7.05-7.15 (m, 1 H), 7.46 (s, 1 H), 7.60 (d, J=7.07 Hz, 1 H), 8.30 (s, 1 H). MS [M+H]+ calc'd for C19H19FN6O2, 383.16; found 383.21.

Example 84

(R)-5-(7-Fluoropyrazolo[4,3-b]indol-4(1H)-yl)-2-(3-hydroxypyrrolidin-1-yl)pyrimidin-4(3H)-one

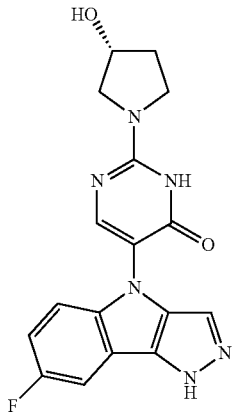 [SMILES: O=c1[nH]c(N2CC[C@@H](O)C2)ncc1-n1c2ccc(F)cc2c2[nH]ncc21]

The title compound was prepared by a method similar to EXAMPLE 66, using (R)-1-(5-bromo-4-methoxypyrimidin-2-yl)pyrrolidin-3-ol in place of 4-(5-bromo-6-methylpyridin-2-yl)morpholine. 1H NMR (400 MHz, CD3OD) δ ppm 1.98-2.24 (m, 2 H), 3.53-3.62 (m, 1 H), 3.62-3.74 (m, 3 H), 4.50-4.55 (m, 1 H), 7.07 (td, J=9.09, 2.53 Hz, 1 H), 7.18 (dd, J=8.84, 4.29 Hz, 1 H), 7.44 (s, 1 H), 7.53 (br s, 1 H), 7.91 (s, 1 H). MS [M+H]+ calc'd for C17H15FN6O2, 355.13; found 355.16.

Example 85

5-(7-Fluoropyrazolo[4,3-b]indol-4(1H)-yl)-4-methylpyrimidin-2-amine

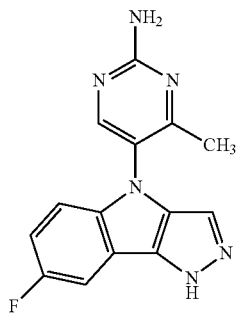 [SMILES: Cc1nc(N)ncc1-n1c2ccc(F)cc2c2[nH]ncc21]

The title compound was prepared by a method similar to EXAMPLE 66, using 5-bromo-4-methylpyrimidin-2-amine in place of 4-(5-bromo-6-methylpyridin-2-yl)morpholine. 1H NMR (400 MHz, CD3OD) δ ppm 2.31 (s, 5 H), 7.27-7.31 (m, 3 H), 7.89 (s, 1 H), 7.94 (s, 2 H). MS [M+H]+ calc'd for C14H11FN6, 283.11; found 283.3.

Example 86

(2R)-3-((5-(7-Fluoropyrazolo[4,3-b]indol-4(1H)-yl)-4-methylpyrimidin-2-yl)amino)propane-1,2-diol

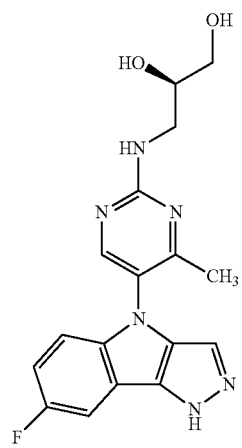 [SMILES: Cc1nc(NC[C@@H](O)CO)ncc1-n1c2ccc(F)cc2c2[nH]ncc21]

The title compound was prepared by a method similar to EXAMPLE 66, using (R)-5-bromo-N-((2,2-dimethyl-1,3-dioxolan-4-yl)methyl)-4-methylpyrimidin-2-amine in place of 4-(5-bromo-6-methylpyridin-2-yl)morpholine. 1H NMR (400 MHz, CD3OD) δ ppm 1.98-2.07 (m, 3 H), 3.45-3.53 (m, 1 H), 3.55-3.69 (m, 3 H), 3.82-3.93 (m, 1 H), 6.97-7.05 (m, 1 H), 7.07-7.17 (m, 1 H), 7.45-7.52 (m, 1 H), 7.60 (d, J=8.08 Hz, 1 H), 8.26 (s, 1 H). MS [M+H]+ calc'd for C17H17FN6O2, 357.15; found 357.3.

Example 87

6-(7-Fluoropyrazolo[4,3-b]indol-4(1H)-yl)-5-methyl-1H-imidazo[4,5-b]pyridin-2(3H)-one

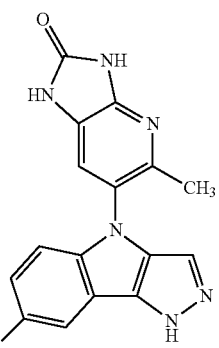

The title compound was prepared by a method similar to EXAMPLE 66, using 6-bromo-5-methyl-1H-imidazo[4,5-b]pyridin-2(3H)-one in place of 4-(5-bromo-6-methylpyridin-2-yl)morpholine. 1H NMR (400 MHz, CD3OD) δ ppm 2.17 (s, 3 H), 6.99 (dd, J=8.84, 4.04 Hz, 1 H), 7.11 (td, J=9.09, 2.78 Hz, 1 H), 7.33 (s, 1 H), 7.45 (s, 1 H), 7.62 (d, J=7.83 Hz, 1 H). MS [M+H]+ calc'd for C16H11FN6O, 323.11; found 323.3.

Example 88

5-(7-Fluoropyrazolo[4,3-b]indol-4(1H)-yl)-N-(2-hydroxyethyl)-1-methyl-1H-pyrazole-3-carboxamide

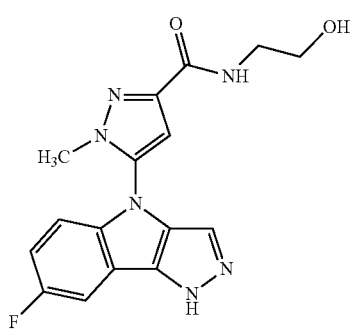 [SMILES: Cn1nc(C(=O)NCCO)cc1-n1c2ccc(F)cc2c2[nH]ncc21]

The title compound was prepared by a method similar to EXAMPLE 66, using 5-bromo-N-(2-hydroxyethyl)-1-methyl-1H-pyrazole-3-carboxamide in place of 4-(5-bromo-6-methylpyridin-2-yl)morpholine. $^1$H NMR (400 MHz, CD$_3$OD) δ ppm 3.44-3.62 (m, 2 H), 3.67-3.82 (m, 5 H), 6.88 (s, 1 H), 7.09-7.26 (m, 2 H), 7.64 (br s, 2 H). MS [M+H]$^+$ calc'd for C$_{16}$H$_{15}$FN$_6$O$_2$, 343.13; found 343.17.

Example 89

1-(5-(7-Fluoropyrazolo[4,3-b]indol-4(1H)-yl)-4-methylpyrimidin-2-yl)azetidine-3-carboxamide

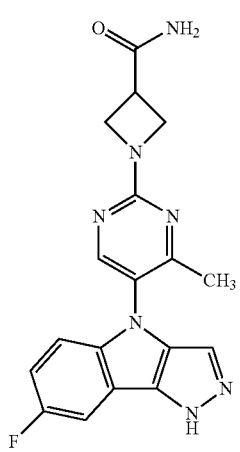 [SMILES: Cc1nc(N2CC(C(N)=O)C2)ncc1-n1c2ccc(F)cc2c2[nH]ncc21]

The title compound was prepared by a method similar to EXAMPLE 66, using 1-(5-bromo-4-methylpyrimidin-2-yl)azetidine-3-carboxamide in place of 4-(5-bromo-6-methylpyridin-2-yl)morpholine, and using potassium tert-butoxide in place of Cs$_2$CO$_3$. $^1$H NMR (400 MHz, CD$_3$OD) δ ppm 2.05 (s, 3 H), 3.52-3.65 (m, 1 H), 4.24-4.41 (m, 4 H), 6.96-7.05 (m, 1 H), 7.07-7.17 (m, 1 H), 7.47 (s, 1 H), 7.61 (d, J=8.59 Hz, 1 H), 8.29 (s, 1 H). MS [M+H]$^+$ calc'd for C$_{18}$H$_{16}$FN$_7$O, 366.15; found 366.3.

Example 90

(2R)-3-(6-(7-Fluoropyrazolo[4,3-b]indol-4(1H)-yl)-5-methyl-3H-imidazo[4,5-b]pyridin-3-yl)propane-1,2-diol

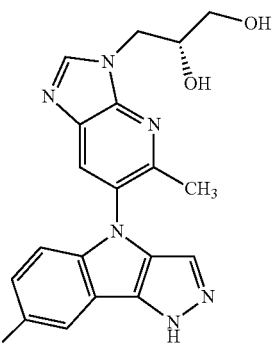

The title compound was prepared by a method similar to EXAMPLE 66, using (R)-6-bromo-3-((2,2-dimethyl-1,3-dioxolan-4-yl)methyl)-5-methyl-3H-imidazo[4,5-b]pyridine in place of 4-(5-bromo-6-methylpyridin-2-yl)morpholine, and using potassium tert-butoxide in place of Cs$_2$CO$_3$. $^1$H NMR (400 MHz, CD$_3$OD) δ ppm 2.36 (s, 3 H), 3.65 (td, J=4.80, 1.77 Hz, 2 H), 4.09-4.22 (m, 1 H), 4.43 (ddd, J=14.15, 8.21, 1.89 Hz, 1 H), 4.72 (dt, J=14.08, 3.19 Hz, 1 H), 6.99 (ddd, J=9.09, 6.57, 4.04 Hz, 1 H), 7.07-7.17 (m, 1 H), 7.47 (d, J=7.33 Hz, 1 H), 7.65 (dd, J=8.72, 2.65 Hz, 1 H), 8.20 (s, 1 H), 8.85 (s, 1 H). MS [M+H]$^+$ calc'd for C$_{19}$H$_{17}$FN$_6$O$_2$, 381.15; found 381.3.

Example 91

(2S)-2-((5-(7-Fluoropyrazolo[4,3-b]indol-4(1H)-yl)-4-methylpyrimidin-2-yl)amino)propan-1-ol

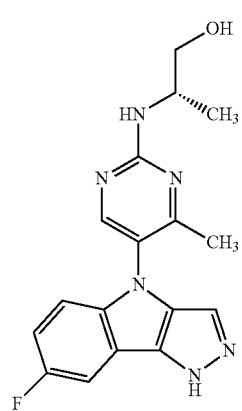 [SMILES: Cc1nc(N[C@@H](C)CO)ncc1-n1c2ccc(F)cc2c2[nH]ncc21]

The title compound was prepared by a method similar to EXAMPLE 66, using (S)-2-((5-bromo-4-methylpyrimidin-2-yl)amino)propan-1-ol in place of 4-(5-bromo-6-methylpyridin-2-yl)morpholine. $^1$H NMR (400 MHz, CD$_3$OD) δ ppm 1.30 (d, J=6.57 Hz, 3 H), 2.03 (s, 3 H), 3.53-3.74 (m, 2 H), 4.15-4.29 (m, 1 H), 7.04 (dd, J=8.97, 4.17 Hz, 1 H), 7.14 (td, J=9.09, 2.53 Hz, 1 H), 7.50 (s, 1 H), 7.63 (dd, J=8.84, 2.27 Hz, 1 H), 8.26 (s, 1 H). MS [M+H]⁺ calc'd for C$_{17}$H$_{17}$FN$_6$O, 341.15; found 341.2.

Example 92

(2S)-1-((5-(7-Fluoropyrazolo[4,3-b]indol-4(1H)-yl)-4-methylpyrimidin-2-yl)amino)propan-2-ol

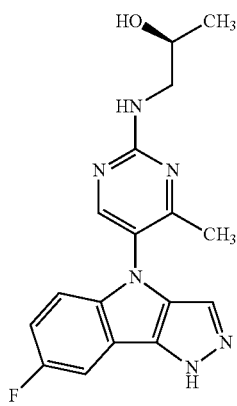 [SMILES: Cc1nc(NC[C@H](C)O)ncc1-n1c2ccc(F)cc2c2[nH]ncc21]

The title compound was prepared by a method similar to EXAMPLE 66, using (S)-1-((5-bromo-4-methylpyrimidin-2-yl)amino)propan-2-ol in place of 4-(5-bromo-6-methylpyridin-2-yl)morpholine. ¹H NMR (400 MHz, CD₃OD) δ ppm 1.22 (d, J=6.32 Hz, 3 H), 2.01 (s, 3 H), 3.31-3.43 (m, 2 H), 3.43-3.55 (m, 1 H), 3.99 (td, J=6.63, 4.67 Hz, 1 H), 6.94-7.05 (m, 1 H), 7.05-7.17 (m, 1 H), 7.47 (s, 1 H), 7.59 (dd, J=8.84, 2.27 Hz, 1 H), 8.24 (s, 1 H). MS [M+H]⁺ calc'd for C$_{17}$H$_{17}$FN$_6$O, 341.15; found 341.2.

Example 93

(2R)-1-((5-(7-Fluoropyrazolo[4,3-b]indol-4(1H)-yl)-4-methylpyrimidin-2-yl)amino)propan-2-ol

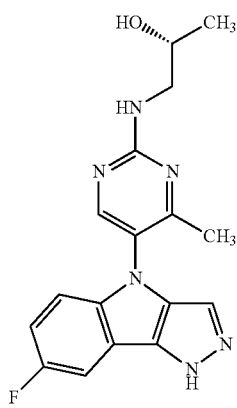 [SMILES: Cc1nc(NC[C@@H](C)O)ncc1-n1c2ccc(F)cc2c2[nH]ncc21]

The title compound was prepared by a method similar to EXAMPLE 66, using (R)-1-((5-bromo-4-methylpyrimidin-2-yl)amino)propan-2-ol in place of 4-(5-bromo-6-methylpyridin-2-yl)morpholine. ¹H NMR (400 MHz, CD₃OD) δ ppm 1.25 (d, J=6.32 Hz, 3 H), 2.04 (s, 3 H), 3.36-3.46 (m, 2 H), 3.46-3.60 (m, 1 H), 4.03 (td, J=6.69, 4.55 Hz, 1 H), 6.94-7.09 (m, 1 H), 7.14 (td, J=9.09, 2.78 Hz, 1 H), 7.50 (s, 1 H), 7.58-7.68 (m, 1 H), 8.27 (s, 1 H). MS [M+H]⁺ calc'd for C$_{17}$H$_{17}$FN$_6$O, 341.15; found 341.2.

Example 94

(5-(7-Fluoropyrazolo[4,3-b]indol-4(1H)-yl)-4-methylpyridin-2-yl)(3-hydroxyazetidin-1-yl)methanone

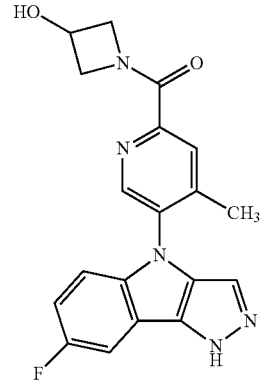 [SMILES: Cc1cc(C(=O)N2CC(O)C2)ncc1-n1c2ccc(F)cc2c2[nH]ncc21]

5-(7-Fluoro-1-(tetrahydro-2H-pyran-2-yl)pyrazolo[4,3-b]indol-4(1H)-yl)-4-methylpicolinic acid (40 mg, 0.101 mmol), azetidin-3-ol hydrochloride (12.22 mg, 0.112 mmol), HATU (42.4 mg, 0.112 mmol), DIPEA (0.053 mL, 0.304 mmol) and DMF (1 mL) were mixed in a 4 mL vial equipped with a magnetic stir bar. The resulting brown solution was stirred overnight. The reaction mixture was subsequently partitioned between water (10 mL) and EtOAc (20 mL) and the layers were separated. The aqueous layer was back-extracted with EtOAc (20 mL). The combined organic layers were concentrated to yield a dark syrup, which was dissolved in MeOH (3 mL) and treated with concentrated HCl (3 drops). The mixture was stirred overnight. The product was purified by preparative HPLC, eluting with 30-55% ACN in aqueous 10 mM NH₄HCO₃. The pure fractions were lyophilized to give the title compound as a white solid (8.3 mg, 22%). ¹H NMR (400 MHz, DMSO-d₆) δ ppm 2.19 (s, 3 H), 3.81-3.87 (m, 2 H), 4.29-4.35 (m, 2 H), 4.51 (br s, 2 H), 4.78-4.81 (m, 1 H), 5.75 (d, J=6.32 Hz, 1 H), 7.17 (dd, J=8.97, 2.65 Hz, 2 H), 7.69 (br s, 2 H), 8.09 (s, 1 H), 8.65 (s, 1 H). MS [M+H]⁺ calc'd for C$_{19}$H$_{16}$FN$_5$O$_2$, 366.14; found 366.3.

Example 95

5-(7-Fluoropyrazolo[4,3-b]indol-4(1H)-yl)-N-(2-hydroxyethyl)-4-methylpicolinamide

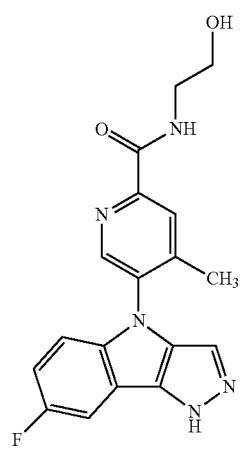 [SMILES: Cc1cc(C(=O)NCCO)ncc1-n1c2ccc(F)cc2c2[nH]ncc21]

The title compound was prepared by a method similar to EXAMPLE 94, using 2-aminoethanol in place of azetidin-3-ol hydrochloride. $^1$H NMR (400 MHz, DMSO-$d_6$) δ ppm 2.22 (s, 3 H), 3.41 (d, J=5.56 Hz, 3 H), 3.54 (d, J=5.56 Hz, 2 H), 4.83 (d, J=5.31 Hz, 1 H), 7.16 (br s, 1 H), 7.18 (d, J=2.02 Hz, 1 H), 8.18 (s, 1 H), 8.67 (s, 1 H), 8.75 (s, 2 H). MS [M+H]$^+$ calc'd for $C_{18}H_{16}FN_5O_2$, 354.14; found 354.3.

Example 96

5-(7-Fluoropyrazolo[4,3-b]indol-4(1H)-yl)-N-(2-hydroxyethyl)-6-methylpicolinamide

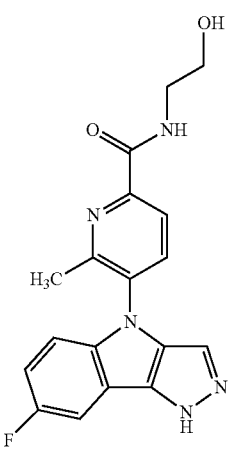 [SMILES: Cc1nc(C(=O)NCCO)ccc1-n1c2ccc(F)cc2c2[nH]ncc21]

5-(7-Fluoro-1-(tetrahydro-2H-pyran-2-yl)pyrazolo[4,3-b]indol-4(1H)-yl)-6-methylpicolinic acid (40 mg, 0.101 mmol), 2-aminoethanol (12.39 mg, 0.203 mmol), HATU (42.4 mg, 0.112 mmol), DIPEA (0.053 mL, 0.304 mmol) and DMF (1 mL) were mixed in a 4 mL vial equipped with a magnetic stir bar. The resulting brown solution was stirred overnight. The reaction mixture was subsequently partitioned between water (15 mL) and EtOAc (15 mL) and the layers were separated. The aqueous layer was back-extracted with EtOAc (15 mL). The combined organic layers were concentrated to yield a dark syrup. The residue was dissolved in MeOH (3 mL) and treated with concentrated HCl (3 drops). The product was purified by preparative HPLC, eluting with 25-50% ACN in aqueous 10 mM NH$_4$HCO$_3$. The pure fractions were lyophilized to give the title compound as a white solid (4.3 mg, 12%). $^1$H NMR (400 MHz, DMSO-$d_6$) δ ppm 2.38 (s, 3 H), 3.44 (s, 3 H), 3.56 (br s, 2 H), 7.15-7.18 (m, 2 H), 7.68 (s, 1 H), 8.05 (d, J=1.52 Hz, 2 H), 8.70 (d, J=7.33 Hz, 1 H). MS [M+H]$^+$ calc'd for $C_{18}H_{16}FN_5O_2$, 354.14; found 354.3.

Example 97

(5-(7-Fluoropyrazolo[4,3-b]indol-4(1H)-yl)-6-methylpyridin-2-yl)(3-hydroxyazetidin-1-yl)methanone

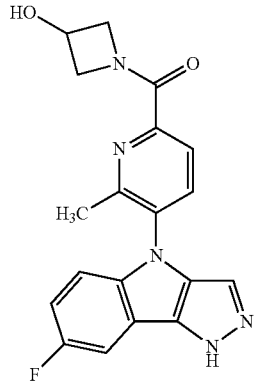 [SMILES: Cc1nc(C(=O)N2CC(O)C2)ccc1-n1c2ccc(F)cc2c2[nH]ncc21]

The title compound was prepared by a method similar to EXAMPLE 96, using azetidin-3-ol hydrochloride in place of 2-aminoethanol. MS [M+H]$^+$ calc'd for $C_{19}H_{16}FN_5O_2$, 366.14; found 366.3.

Example 98

N-Benzyl-7-fluoropyrazolo[4,3-b]indole-4(1H)-carboxamide

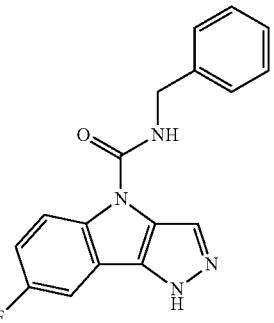

7-Fluoro-1-(tetrahydro-2H-pyran-2-yl)-1,4-dihydropyrazolo[4,3-b]indole (40 mg, 0.154 mmol), Et$_3$N (0.065 mL, 0.463 mmol), (isocyanatomethyl)benzene (20.54 mg, 0.154 mmol) and DMF (1 mL) were mixed in a 4 mL vial equipped with a magnetic stir bar to give a brown solution. The mixture was stirred overnight at 100° C. The reaction mixture was subsequently partitioned between water (15 mL) and EtOAc (15 mL). The layers were separated and the aqueous layer was back-extracted with EtOAc (15 mL). The combined organic layers were concentrated to yield a dark syrup, which was dissolved in MeOH (3 mL) and treated with concentrated HCl (3 drops). After stirring for 18 hours, the product was purified by preparative HPLC, eluting with 35-60% ACN in water (containing 0.05% TFA). The pure fractions were lyophilized to give a TFA salt of the title compound as a white solid (11.5 mg, 17.7%). $^1$H NMR (400 MHz, DMSO-$d_6$) δ ppm 4.52 (d, J=5.81 Hz, 2 H), 7.24 (td, J=9.22, 2.78 Hz, 2 H), 7.32-7.36 (m, 2 H), 7.38-7.41 (m, 2

H), 7.63 (dd, J=8.59, 2.78 Hz, 1 H), 7.77 (s, 1 H), 8.14 (s, 1 H), 8.33 (dd, J=9.22, 4.67 Hz, 1 H). MS [M+H]+ calc'd for C$_{17}$H$_{13}$FN$_4$O, 309.12; found 309.2.

Example 99

Cyclopropyl(7-fluoropyrazolo[4,3-b]indol-4(1H)-yl)methanone

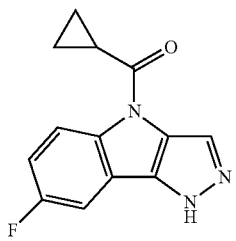 [SMILES: O=C(C1CC1)n1c2ccc(F)cc2c2[nH]ncc21]

A TFA salt of the title compound was prepared by a method similar to EXAMPLE 98, using cyclopropanecarbonyl chloride in place of (isocyanatomethyl)benzene. 1H NMR (400 MHz, DMSO-d$_6$) δ ppm 1.05-1.16 (m, 4 H), 2.53 (d, J=3.03 Hz, 1 H), 7.27 (td, J=9.35, 2.78 Hz, 1 H), 7.66 (dd, J=8.59, 2.78 Hz, 1 H), 8.17 (s, 1 H), 8.49 (dd, J=9.09, 4.80 Hz, 1 H). MS [M+H]+ calc'd for C$_{13}$H$_{10}$FN$_3$O, 244.09; found 244.1.

Example 100

5-(7-Fluoropyrazolo[4,3-b]indol-4(1H)-yl)-N-(1-(hydroxymethyl)cyclopropyl)-6-methylpicolinamide

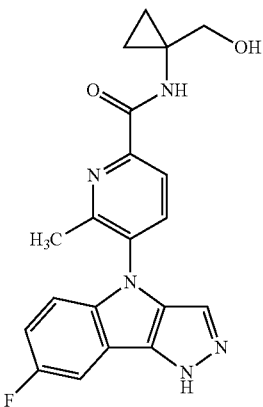 [SMILES: Cc1nc(C(=O)NC2(CO)CC2)ccc1-n1c2ccc(F)cc2c2[nH]ncc21]

5-(7-Fluoro-1-(tetrahydro-2H-pyran-2-yl)pyrazolo[4,3-b]indol-4(1H)-yl)-6-methylpicolinic acid (30 mg, 0.076 mmol), (1-aminocyclopropyl)methanol hydrochloride (18.80 mg, 0.152 mmol), HATU (34.7 mg, 0.091 mmol), DIPEA (0.040 mL, 0.228 mmol) and DMF (1 mL) were mixed in a 4 mL vial equipped with a magnetic stir bar. The resulting brown solution was stirred overnight. The reaction mixture was partitioned between water (10 mL) and EtOAc (20 mL). The layers were separated and the aqueous layer was back-extracted with EtOAc (20 mL). The combined organic layers were concentrated to yield a dark syrup, which was dissolved in MeOH (3 mL) and treated with concentrated HCl (3 drops). The mixture was stirred overnight and subsequently purified by preparative HPLC, eluting with 25-50% ACN in water (containing 0.05% TFA). The pure fractions were lyophilized to give a TFA salt of the title compound as a light yellow solid (5.3 mg, 14%). $^1$H NMR (400 MHz, DMSO-d$_6$) δ ppm 0.82 (s, 4 H), 2.37 (s, 3 H), 3.55 (s, 2 H), 7.14-7.18 (m, 2 H), 7.66 (s, 1 H), 7.70 (s, 1 H), 7.68 (s, 1 H), 8.00-8.06 (m, 2 H), 8.75 (s, 1 H). MS [M+H]+ calc'd for C$_{20}$H$_{18}$FN$_5$O$_2$, 380.15; found 380.4.

Example 101

N-Cyclopropyl-5-(7-fluoropyrazolo[4,3-b]indol-4(1H)-yl)-6-methylpicolinamide

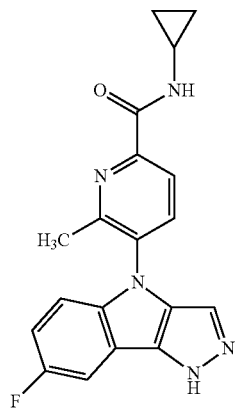 [SMILES: Cc1nc(C(=O)NC2CC2)ccc1-n1c2ccc(F)cc2c2[nH]ncc21]

A TFA salt of the title compound was prepared by a method similar to EXAMPLE 100, using cyclopropanamine in place of (1-aminocyclopropyl)methanol hydrochloride. $^1$H NMR (400 MHz, DMSO-d$_6$) δ ppm 0.70-0.75 (m, 4 H), 2.36 (s, 3 H), 2.90-2.93 (m, 1 H), 7.12-7.18 (m, 2 H), 7.66-7.71 (m, 2 H), 8.00-8.05 (m, 2 H), 8.67 (d, J=4.80 Hz, 1 H). MS [M+H]+ calc'd for C$_{19}$H$_{16}$FN$_5$O, 350.14; found 350.3.

Example 102

5-(7-Fluoropyrazolo[4,3-b]indol-4(1H)-yl)-N-(2-methoxyethyl)-6-methylpicolinamide

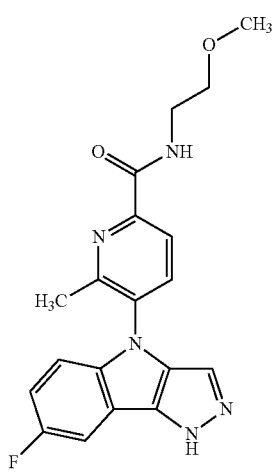 [SMILES: COCCNC(=O)c1ccc(-n2c3ccc(F)cc3c3[nH]ncc32)c(C)n1]

A TFA salt of the title compound was prepared by a method similar to EXAMPLE 100, using 2-methoxyethanamine in place of (1-aminocyclopropyl)methanol hydrochloride. $^1$H NMR (400 MHz, DMSO-$d_6$) δ ppm 2.39 (s, 3 H), 3.29 (s, 3 H), 3.51-3.52 (m, 4 H), 7.15-7.18 (m, 2 H), 7.68-7.71 (m, 2 H), 8.05 (d, J=2.27 Hz, 2 H), 8.69-8.71 (m, 1 H). MS [M+H]$^+$ calc'd for $C_{19}H_{18}FN_5O_2$, 368.15; found 368.3.

Example 103

(3S)-1-(5-(7-Fluoropyrazolo[4,3-b]indol-4(1H)-yl)-4-methylpyrimidin-2-yl)-N-(2-hydroxyethyl)pyrrolidine-3-carboxamide

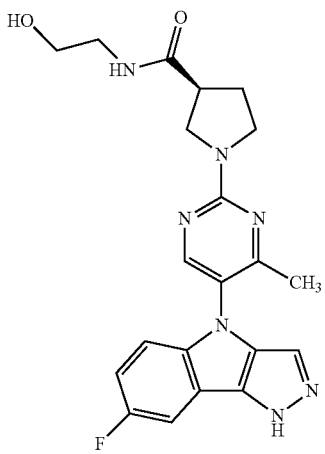 [SMILES: Cc1nc(N2CC[C@H](C(=O)NCCO)C2)ncc1-n1c2ccc(F)cc2c2[nH]ncc21]

A TFA salt of the title compound was prepared by a method similar to EXAMPLE 100, using 2-aminoethanol in place of (1-aminocyclopropyl)methanol hydrochloride. 1H NMR (400 MHz, DMSO-$d_6$) δ ppm 1.98 (s, 3 H), 2.06-2.18 (m, 2 H), 3.08-3.19 (m, 4 H), 3.42 (t, J=6.06 Hz, 2 H), 3.51-3.62 (m, 4 H), 7.07 (d, J=8.08 Hz, 1 H), 7.12 (dd, J=9.22, 2.40 Hz, 1 H), 7.60 (br s, 1 H), 7.64 (dd, J=8.97, 2.65 Hz, 1 H), 8.06 (t, J=5.68 Hz, 1 H), 8.35 (s, 1 H). MS [M+H]$^+$ calc'd for $C_{21}H_{22}FN_7O_2$, 424.19; found 424.4.

Example 104

5-(7-Fluoropyrazolo[4,3-b]indol-4(1H)-yl)-N-(1-(hydroxymethyl)cyclopropyl)-4-methylpicolinamide

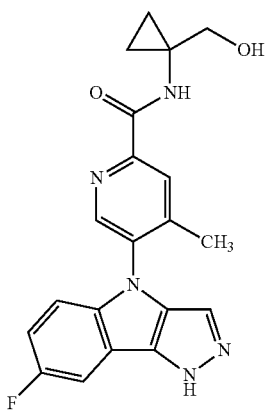 [SMILES: Cc1cc(C(=O)NC2(CO)CC2)ncc1-n1c2ccc(F)cc2c2[nH]ncc21]

5-(7-Fluoro-1-(tetrahydro-2H-pyran-2-yl)pyrazolo[4,3-b]indol-4(1H)-yl)-4-methylpicolinic acid (30 mg, 0.076 mmol), (1-aminocyclopropyl)methanol hydrochloride (18.80 mg, 0.152 mmol), HATU (34.7 mg, 0.091 mmol), DIPEA (0.040 mL, 0.228 mmol) and DMF (1 mL) were mixed in a 4 mL vial equipped with a magnetic stir bar. The resulting brown solution was stirred overnight. The reaction mixture was partitioned between water (10 mL) and EtOAc (20 mL). The layers were separated and the aqueous layer was back-extracted with EtOAc (20 mL). The combined organic layers were concentrated to yield a dark syrup, which was dissolved in MeOH (3 mL), treated with concentrated HCl (3 drops), and stirred overnight. The product was purified by preparative HPLC, eluting with 25-50% ACN in water (containing 0.05% TFA). The pure fractions were lyophilized to give a TFA salt of the title compound as a light yellow solid (12.3 mg, 32.8%). $^1$H NMR (400 MHz, DMSO-$d_6$) δ ppm 0.80 (s, 3 H), 1.01 (d, J=17.68 Hz, 1 H), 2.21 (s, 3 H), 3.54 (s, 2 H), 7.11-7.18 (m, 2 H), 7.64-7.66 (m, 1 H), 7.69 (dd, J=9.09, 2.53 Hz, 1 H), 8.16 (s, 1 H), 8.64 (s, 1H), 8.81 (s, 1 H). MS [M+H]$^+$ calc'd for $C_{20}H_{18}FN_5O_2$, 380.15; found 380.4.

Example 105

5-(7-Fluoropyrazolo[4,3-b]indol-4(1H)-yl)-N-(2-methoxyethyl)-4-methylpicolinamide

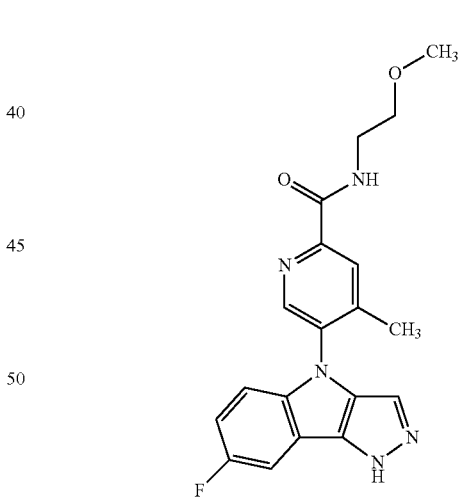

A TFA salt of the title compound was prepared by a method similar to EXAMPLE 104, using 2-methoxyethanamine in place of (1-aminocyclopropyl)methanol hydrochloride. $^1$H NMR (400 MHz, DMSO-$d_6$) δ ppm 2.21-2.24 (m, 3 H), 3.27-3.30 (m, 3 H), 3.49-3.52 (m, 4 H), 7.15-7.18 (m, 2 H), 7.67-7.71 (m, 2 H), 8.18 (s, 1 H), 8.67 (s, 1 H), 8.76 (d, J=4.55 Hz, 1 H). MS [M+H]$^+$ calc'd for $C_{19}H_{18}FN_5O_2$, 368.15; found 368.3.

Example 106

(5-(7-Fluoropyrazolo[4,3-b]indol-4(1H)-yl)-4-methylpyridin-2-yl)(morpholino)methanone

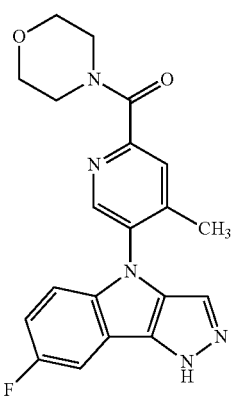 [SMILES: Cc1cc(C(=O)N2CCOCC2)ncc1-n1c2ccc(F)cc2c2[nH]ncc21]

A TFA salt of the title compound was prepared by a method similar to EXAMPLE 104, using morpholine in place of (1-aminocyclopropyl)methanol hydrochloride. $^1$H NMR (400 MHz, DMSO-d$_6$) δ ppm 2.16 (s, 3 H), 3.58 (d, J=9.60 Hz, 5 H), 3.69 (s, 4 H), 7.16-7.19 (m, 2 H), 7.69 (d, J=8.34 Hz, 2 H), 7.77 (s, 1 H), 8.62 (s, 1 H). MS [M+H]$^+$ calc'd for C$_{20}$H$_{18}$FN$_5$O$_2$, 380.15; found 380.3.

Example 107

5-(7-Fluoropyrazolo[4,3-b]indol-4(1H)-yl)-4-methylpicolinamide

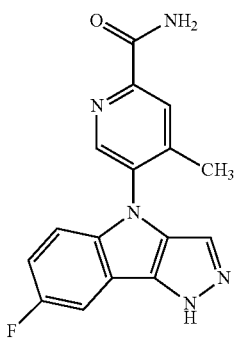 [SMILES: Cc1cc(C(N)=O)ncc1-n1c2ccc(F)cc2c2[nH]ncc21]

A TFA salt of the title compound was prepared by a method similar to EXAMPLE 104, using ammonia hydrochloride in place of (1-aminocyclopropyl)methanol hydrochloride. $^1$H NMR (400 MHz, CD$_3$OD) δ ppm 2.27 (br s, 3 H), 7.09-7.16 (m, 3 H), 7.55 (s, 1 H), 7.66 (dd, J=8.72, 2.40 Hz, 2 H), 8.23 (s, 1 H), 8.65 (br s, 1 H). MS [M+H]$^+$ calc'd for C$_{16}$H$_{12}$FN$_5$O, 310.11; found 310.2.

Example 108

5-(7-Fluoropyrazolo[4,3-b]indol-4(1H)-yl)-N,N,4-trimethylpicolinamide

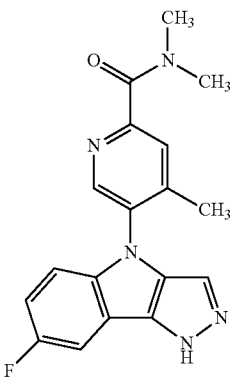 [SMILES: Cc1cc(C(=O)N(C)C)ncc1-n1c2ccc(F)cc2c2[nH]ncc21]

A TFA salt of the title compound was prepared by a method similar to EXAMPLE 104, using dimethylamine (2M in THF) in place of (1-aminocyclopropyl)methanol hydrochloride. 1H NMR (400 MHz, CD$_3$OD) δ ppm 2.22 (s, 3 H), 3.14 (s, 3 H), 3.20 (s, 3 H), 7.11-7.17 (m, 3 H), 7.64-7.68 (m, 2 H). MS [M+H]$^+$ calc'd for C$_{18}$H$_{16}$FN$_5$O, 338.14; found 338.3.

Example 109

(5-(7-Fluoropyrazolo[4,3-b]indol-4(1H)-yl)-4-methylpyridin-2-yl)((R)-3-hydroxypyrrolidin-1-yl)methanone

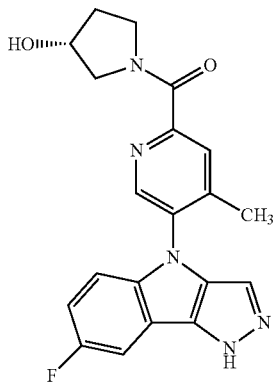 [SMILES: Cc1cc(C(=O)N2CC[C@@H](O)C2)ncc1-n1c2ccc(F)cc2c2[nH]ncc21]

A TFA salt of the title compound was prepared by a method similar to EXAMPLE 104, using (R)-pyrrolidin-3-ol in place of (1-aminocyclopropyl)methanol hydrochloride. $^1$H NMR (400 MHz, CD$_3$OD) δ ppm 2.13 (br s, 3 H), 3.88 (br s, 4 H), 4.89-4.91 (m, 1 H), 7.15 (br s, 2 H), 7.66 (d, J=8.59 Hz, 1 H). MS [M+H]$^+$ calc'd for C$_{20}$H$_{18}$FN$_5$O$_2$, 380.15; found 380.4.

Example 110

7-Fluoro-4-(7-methyl-3H-imidazo[4,5-b]pyridin-6-yl)-1,4-dihydropyrazolo[4,3-b]indole

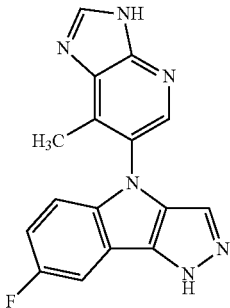 [SMILES: Cc1c(-n2c3ccc(F)cc3c3[nH]ncc32)cnc2[nH]cnc12]

7-Fluoro-1-(tetrahydro-2H-pyran-2-yl)-1,4-dihydropyrazolo[4,3-b]indole (60 mg, 0.231 mmol), 6-bromo-7-methyl-3H-imidazo[4,5-b]pyridine (83 mg, 0.393 mmol), copper(I) iodide (4.41 mg, 0.023 mmol), $Cs_2CO_3$ (226 mg, 0.694 mmol) and DMF (3 mL) were mixed in an 8 mL tube equipped with a magnetic stir bar. The resulting brown suspension was purged with nitrogen and the tube was sealed. The reaction mixture was heated in a sand bath for 18 hours at 180° C. The reaction was subsequently poured into water (25 mL) and extracted with EtOAc (2×40 mL). The combined organic layers were washed with brine (20 mL) and concentrated to yield a brown syrup, which was dissolved in MeOH (5 mL), treated with concentrated HCl (4 drops), and stirred overnight. The reaction mixture was purified by preparative HPLC, eluting with 15-40% ACN in water (containing 0.05% TFA) to yield product (26 mg) with an impurity. The product was re-purified by preparative HPLC, eluting with 40-65% ACN in aqueous 10 mM $NH_4HCO_3$. The pure fractions were lyophilized to give the title compound as a white solid (10 mg, 14%). $^1$H NMR (400 MHz, DMSO-$d_6$) δ ppm 2.26 (s, 3 H), 6.54 (s, 2 H), 7.13 (s, 2 H), 8.36 (s, 1 H), 8.54 (s, 2 H). MS [M+H]$^+$ calc'd for $C_{16}H_{11}FN_6$, 307.11; found 307.2.

Example 111

((3S)-1-(5-(7-Fluoropyrazolo[4,3-b]indol-4(1H)-yl)-4-methylpyrimidin-2-yl)pyrrolidin-3-yl)(3-hydroxyazetidin-1-yl)methanone

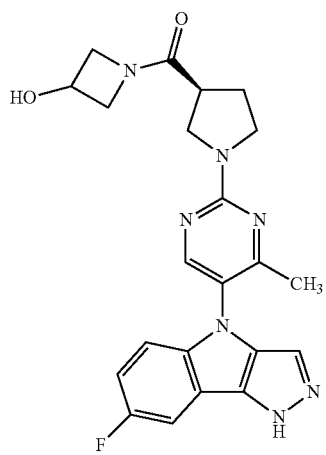 [SMILES: Cc1nc(N2CC[C@H](C(=O)N3CC(O)C3)C2)ncc1-n1c2ccc(F)cc2c2[nH]ncc21]

Step A: (S)-1-(5-Bromo-4-methylpyrimidin-2-yl)pyrrolidine-3-carboxylic acid

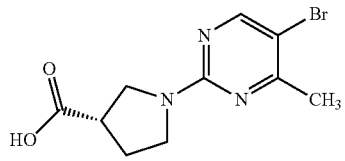 [SMILES: Cc1nc(N2CC[C@H](C(=O)O)C2)ncc1Br]

5-Bromo-2-chloro-4-methypyrimidine (300 mg, 446 mol), (S)-pyrrolidine-3-carboxylic acid hydrochloride (219 mg, 1.446 mmol), $Et_3N$ (0.605 mL, 4.34 mmol) and DMF (2 mL) were mixed in an 8 mL tube equipped with a magnetic stir bar to give an orange solution. The tube was sealed and the mixture was heated to 70° C. for 72 hours. The reaction was partitioned between water (20 mL) and EtOAc (20 mL). The layers were separated and the aqueous layer was back-extracted with EtOAc (20 mL). The combined organic layers were dried over $Na_2SO_4$, filtered, and concentrated to yield the title compound as a tan solid which was used without further purification (160 mg, 38.7%). MS [M+H]$^+$ calc'd for $C_{10}H_{12}BrN_3O_2$, 286.02; found 286.0.

Step B: (3S)-1-(5-(7-Fluoro-1-(tetrahydro-2H-pyran-2-yl)pyrazolo[4,3-b]indol-4(1H)-yl)-4-methylpyrimidin-2-yl)pyrrolidine-3-carboxylic acid

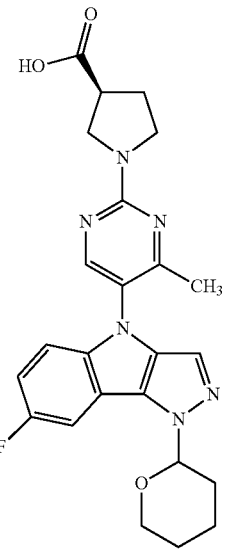

7-Fluoro-1-(tetrahydro-2H-pyran-2-yl)-1,4-dihydropyrazolo[4,3-b]indole (90 mg, 0.347 mmol), (S)-1-(5-bromo-4-methylpyrimidin-2-yl)pyrrolidine-3-carboxylic acid (159 mg, 0.555 mmol), ((thiophene-2-carbonyl)oxy)copper (6.62 mg, 0.035 mmol), $Cs_2CO_3$ (339 mg, 1.041 mmol) and DMF (2 mL) were mixed in an 8 mL tube equipped with a magnetic stir bar. The resulting brown suspension was purged with $N_2$ and the tube was sealed. The reaction mixture was heated for 48 hours at 180° C. in a sand bath. The reaction mixture was subsequently partitioned between water (20 mL) and EtOAc (20 mL) and the layers were separated. The organic layer was discarded and the aqueous layer was acidified with 1N HCl and extracted with EtOAc (2×40 mL). The combined organic layers were concentrated to yield a dark syrup, which was triturated with water. A brown solid was filtered off, washed with water, and dried. The solid residue was dissolved in MeOH and filtered. The filtrate was concentrated to give the title compound as a tan solid, which was used without further purification (50 mg, 31%).

Step C: ((3S)-1-(5-(7-Fluoro-1-(tetrahydro-2H-pyran-2-yl)pyrazolo[4,3-b]indol-4(1H)-yl)-4-methylpyrimidin-2-yl)pyrrolidin-3-yl)(3-hydroxyazetidin-1-yl)methanone

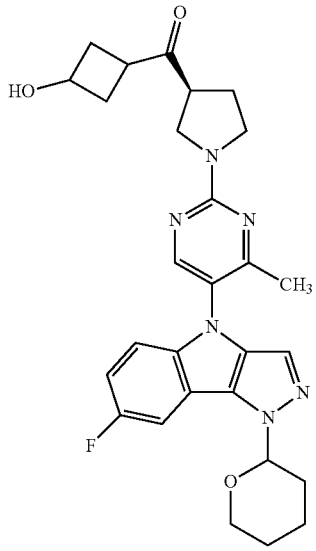 [SMILES: Cc1nc(N2CC[C@H](C(=O)C3CC(O)C3)C2)ncc1-n1c2ccc(F)cc2c2c1cnn2C1CCCCO1]

(3S)-1-(5-(7-Fluoro-1-(tetrahydro-2H-pyran-2-yl)pyrazolo[4,3-b]indol-4(1H)-yl)-4-methylpyrimidin-2-yl)pyrrolidine-3-carboxylic acid (25 mg, 0.054 mmol), azetidin-3-ol hydrochloride (5.90 mg, 0.054 mmol), HATU (24.56 mg, 0.065 mmol), DIPEA (0.028 mL, 0.161 mmol) and DMF (2 mL) were mixed in a 4 mL vial equipped with a magnetic stir bar. The resulting brown solution was stirred overnight. The reaction mixture was partitioned between water (15 mL) and EtOAc (20 mL). The layers were separated and the aqueous layer was back-extracted with EtOAc (20 mL). The combined organic layers were washed with brine (15 mL) and concentrated to yield the title compound as a brown syrup, which was used without further purification.

Step D: ((3S)-1-(5-(7-Fluoropyrazolo[4,3-b]indol-4 (1H)-yl)-4-methylpyrimidin-2-yl)pyrrolidin-3-yl)(3-hydroxyazetidin-1-yl)methanone ((3S)-1-(5-(7-Fluoro-1-(tetrahydro-2H-pyran-2-yl)pyrazolo[4,3-b]indol-4(1H)-yl)-4-methylpyrimidin-2-yl)pyrrolidin-3-yl)(3-hydroxyazetidin-1-yl)methanone was dissolved in MeOH (3 mL), treated with concentrated HCl (4 drops) and stirred for 3 hours at 70° C. The product was purified by preparative HPLC, eluting with 20-45% ACN in water (containing 0.05% TFA). The pure fractions were lyophilized to give a TFA salt of the title compound as a light yellow solid (8.2 mg, 28%). $^1$H NMR (400 MHz, DMSO-$d_6$) δ ppm 1.98 (d, J=1.52 Hz, 3 H), 2.06 (d, J=8.59 Hz, 1 H), 2.16 (d, J=5.05 Hz, 1 H), 3.13-3.20 (m, 2 H), 3.95 (d, J=9.09 Hz, 1 H), 4.04-4.09 (m, 2 H), 4.38-4.45 (m, 2 H), 4.48 (br s, 1 H), 6.96 (s, 1 H), 7.09 (s, 1 H), 7.11-7.16 (m, 1 H), 7.22 (s, 1 H), 7.59 (br s, 1 H), 7.64 (d, J=9.09 Hz, 1 H), 8.35 (d, J=1.77 Hz, 1 H). MS [M+H]$^+$ calc'd for $C_{22}H_{22}FN_7O_2$, 436.19; found 436.4.

Example 112

4-(5-Ethyl-4,5,6,7-tetrahydropyrazolo[1,5-a]pyrazin-3-yl)-7-fluoro-1,4-dihydropyrazolo[4,3-b]indole

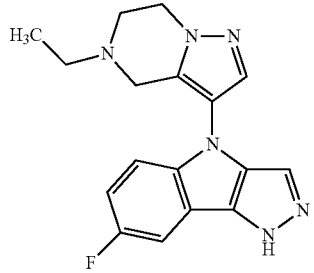 [SMILES: CCN1CCn2ncc(-n3c4ccc(F)cc4c4[nH]ncc43)c2C1]

7-Fluoro-4-(4,5,6,7-tetrahydropyrazolo[1,5-a]pyrazin-3-yl)-1,4-dihydropyrazolo[4,3-b]indole 2,2,2-trifluoroacetate (30 mg, 0.073 mmol), acetaldehyde (6.44 mg, 0.146 mmol), borane pyridine (0.091 mL, 0.731 mmol) and MeOH (2 mL) were mixed in a 4 mL vial equipped with a magnetic stir bar. The resulting yellow solution was stirred overnight. The product was purified by preparative HPLC, eluting with 35-60% ACN in aqueous 10 mM NH$_4$HCO$_3$. The pure fractions were lyophilized to give the title compound as a white solid (7.1 mg, 30%). $^1$H NMR (400 MHz, DMSO-$d_6$) δ ppm 0.97-1.02 (m, 3 H), 2.54 (s, 1 H), 2.97 (br s, 2 H), 3.45 (br s, 2 H), 4.19 (br s, 2 H), 7.14 (br s, 2 H), 7.51 (br s, 1 H), 7.68 (br s, 1 H), 7.75 (br s, 1 H). MS [M+H]$^+$ calc'd for $C_{17}H_{17}FN_6$, 325.16; found 325.3.

Example 113

5-(7-Fluoropyrazolo[4,3-b]indol-4(1H)-yl)-N,4-dimethylpicolinamide

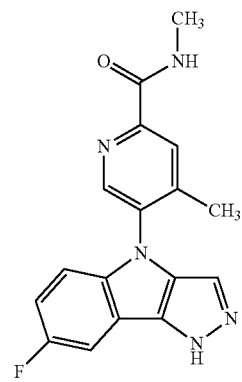 [SMILES: CNC(=O)c1cc(C)c(-n2c3ccc(F)cc3c3[nH]ncc32)cn1]

5-(7-Fluoro-1-(tetrahydro-2H-pyran-2-yl)pyrazolo[4,3-b]indol-4(1H)-yl)-4-methylpicolinic acid (35 mg, 0.089 mmol), methanamine (2M in THF) (0.089 mL, 0.177 mmol), HATU (40.5 mg, 0.106 mmol), DIPEA (0.046 mL, 0.266 mmol) and DMF (1.5 mL) were mixed in a 4 mL vial equipped with a magnetic stir bar. The resulting brown solution was stirred overnight. The reaction mixture was partitioned between water (10 mL) and EtOAc (20 mL). The layers were separated and the aqueous layer was back-extracted with EtOAc (20 mL). The combined organic layers were concentrated to yield a dark syrup, which was dissolved in MeOH (3 mL), treated with concentrated HCl (3 drops), and stirred overnight. The product was purified by preparative HPLC, eluting with a gradient of ACN in water (containing 0.05% TFA). The pure fractions were lyophilized to give a TFA salt of the title compound as a light yellow solid (13.8 mg, 35.6%). $^1$H NMR (400 MHz, DMSO-$d_6$) δ ppm 2.21 (s, 3 H), 2.85 (d, J=4.80 Hz, 3 H), 7.12-7.21 (m, 3 H), 7.67-7.71 (m, 2 H), 8.17 (s, 1 H), 8.65 (s, 1 H), 8.86 (d, J=4.29 Hz, 1 H). MS [M+H]$^+$ calc'd for $C_{17}H_{14}FN_5O$, 324.13; found 324.3.

Example 114

(3-Aminoazetidin-1-yl)(5-(7-fluoropyrazolo[4,3-b]indol-4(1H)-yl)-4-methylpyridin-2-yl)methanone

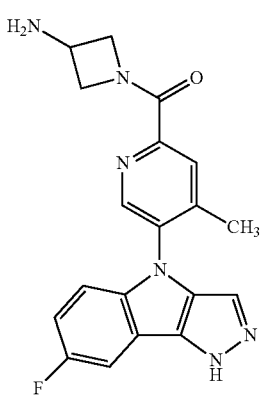 [SMILES: Cc1cc(C(=O)N2CC(N)C2)ncc1-n1c2ccc(F)cc2c2[nH]ncc21]

A TFA salt of the title compound was prepared by a method similar to EXAMPLE 113, using tert-butyl azetidin-3-ylcarbamate in place of methanamine. 1H NMR (400 MHz, CD$_3$OD) δ ppm 2.27 (s, 3 H), 4.18-4.26 (m, 4 H), 4.55-4.61 (m, 2 H), 5.13 (d, J=6.32 Hz, 1 H), 7.07-7.16 (m, 3 H), 7.51 (d, J=5.05 Hz, 1 H), 7.65 (d, J=9.09 Hz, 1 H), 8.20 (s, 1 H), 8.66 (s, 1 H). MS [M+H]$^+$ calc'd for $C_{19}H_{17}FN_6O$, 365.15; found 365.4.

Example 115

5-(7-Fluoropyrazolo[4,3-b]indol-4(1H)-yl)-N-(3-hydroxypropyl)-4-methylpicolinamide

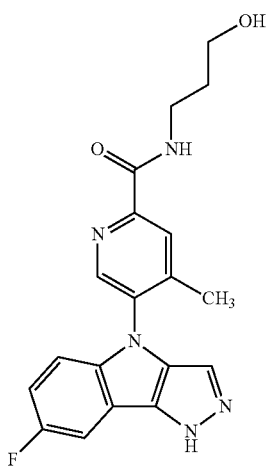 [SMILES: Cc1cc(C(=O)NCCCO)ncc1-n1c2ccc(F)cc2c2[nH]ncc21]

A TFA salt of the title compound was prepared by a method similar to EXAMPLE 113, using 3-aminopropan-1-ol in place of methanamine. 1H NMR (400 MHz, CD$_3$OD) δ ppm 1.84 (d, J=6.57 Hz, 2 H), 2.22 (br s, 3 H), 3.52 (br s, 2 H), 3.64 (t, J=6.32 Hz, 2 H), 7.05-7.12 (m, 3 H), 7.50 (br s, 1 H), 7.61 (dd, J=8.72, 2.65 Hz, 2 H), 8.16 (br s, 1 H), 8.60 (br s, 1 H). MS [M+H]$^+$ calc'd for $C_{19}H_{18}FN_5O_2$, 368.15; found 368.4.

Example 116

7-Fluoro-4-(5-methyl-3-(2-(methylsulfonyl)ethyl)-3H-imidazo[4,5-b]pyridin-6-yl)-1,4-dihydropyrazolo[4,3-b]indole

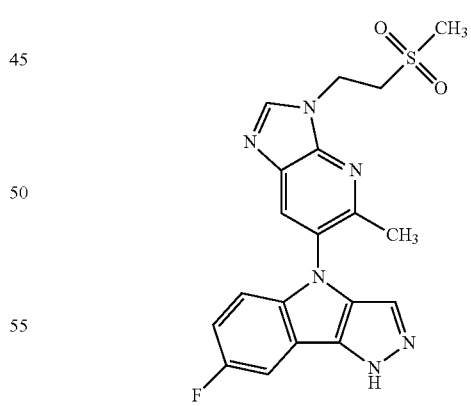

7-Fluoro-4-(5-methyl-3H-imidazo[4,5-b]pyridin-6-yl)-1-(tetrahydro-2H-pyran-2-yl)-1,4-dihydropyrazolo[4,3-b]indole (50 mg, 0.128 mmol), NaH (5.12 mg, 0.128 mmol) and DMF (2 mL) were mixed in a 20 mL vial equipped with a magnetic stir bar to give a brown solution. After stirring for a few minutes, 1-chloro-2-(methylsulfonyl)ethane (18.26 mg, 0.128 mmol) was added. The mixture was stirred overnight, then heated to 65° C. for 2 days. The reaction mixture was subsequently partitioned between water (20 mL) and EtOAc (20 mL). The layers were separated and the aqueous layer was back-extracted with EtOAc (20 mL). The combined organic layers were concentrated to yield a tan syrup, which was dissolved in MeOH (5 mL), treated with concentrated HCl (4 drops), and stirred for 3 hours at 60° C. The product was purified by preparative HPLC, eluting with 20-45% ACN in water (containing 0.05% TFA). The pure fractions were lyophilized to give a TFA salt of the title compound as a white solid (7.4 mg, 11%). $^1$H NMR (400 MHz, CD$_3$OD) δ ppm 2.36 (s, 3 H), 3.07 (s, 3 H), 3.91 (t, J=6.44 Hz, 2 H), 4.94-4.98 (m, 2 H), 6.98 (dd, J=8.97, 4.17 Hz, 1 H), 7.12 (td, J=9.16, 2.65 Hz, 1 H), 7.48 (br s, 1 H), 7.65 (dd, J=8.84, 2.53 Hz, 1 H), 8.16 (br s, 1 H). MS [M+H]$^+$ calc'd for C$_{19}$H$_{17}$FN$_6$O$_2$S, 413.12; found 413.4.

Example 117

(3-Aminoazetidin-1-yl)(5-(7-fluoropyrazolo[4,3-b]indol-4(1H)-yl)-6-methylpyridin-2-yl)methanone

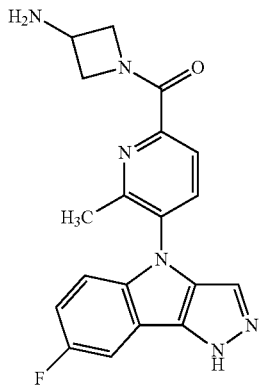 [SMILES: Cc1nc(C(=O)N2CC(N)C2)ccc1-n1c2ccc(F)cc2c2[nH]ncc21]

5-(7-Fluoro-1-(tetrahydro-2H-pyran-2-yl)pyrazolo[4,3-b]indol-4(1H)-yl)-6-methylpicolinic acid (35 mg, 0.089 mmol), tert-butyl azetidin-3-ylcarbamate (30.6 mg, 0.177 mmol), HATU (40.5 mg, 0.106 mmol), DIPEA (0.046 mL, 0.266 mmol) and DMF (1.5 mL) were mixed in a 4 mL vial equipped with a magnetic stir bar to give a brown solution. The reaction mixture was stirred overnight and then partitioned between water (10 mL) and EtOAc (20 mL). The layers were separated and the aqueous layer was back-extracted with EtOAc (20 mL). The combined organic layers were concentrated to yield a dark syrup, which was dissolved in MeOH (3 mL), treated with concentrated HCl (3 drops), and stirred overnight. The product was purified by preparative HPLC, eluting with 15-40% ACN in water (containing 0.05% TFA). The pure fractions were lyophilized to give a TFA salt of the title compound as a white solid (13.7 mg, 32.3%). $^1$H NMR (400 MHz, DMSO-d$_6$) δ ppm 2.36 (s, 3 H), 4.06-4.17 (m, 4 H), 4.37 (br s, 1 H), 7.14-7.20 (m, 2 H), 7.68 (br s, 1 H), 7.99 (d, J=8.34 Hz, 1 H), 8.07 (d, J=8.59 Hz, 1 H), 8.29 (br s, 1 H). MS [M+H]$^+$ calc'd for C$_{19}$H$_{17}$FN$_6$O, 365.15; found 365.4.

Example 118

5-(7-Fluoropyrazolo[4,3-b]indol-4(1H)-yl)-N-(3-hydroxypropyl)-6-methylpicolinamide

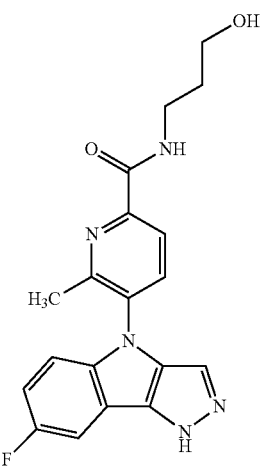 [SMILES: Cc1nc(C(=O)NCCCO)ccc1-n1c2ccc(F)cc2c2[nH]ncc21]

A TFA salt of the title compound was prepared by a method similar to EXAMPLE 117, using 3-aminopropan-1-ol in place of tert-butyl azetidin-3-ylcarbamate. 1H NMR (400 MHz, DMSO-d$_6$) δ ppm 1.69-1.76 (m, 2 H), 2.37-2.39 (m, 3 H), 3.39-3.51 (m, 5 H), 7.14-7.18 (m, 2 H), 7.67-7.71 (m, 2 H), 8.00-8.07 (m, 2 H), 8.83 (s, 1 H). MS [M+H]$^+$ calc'd for C$_{19}$H$_{18}$FN$_5$O$_2$, 368.15; found 368.4.

Example 119

5-(7-Fluoropyrazolo[4,3-b]indol-4(1H)-yl)-N,6-dimethylpicolinamide

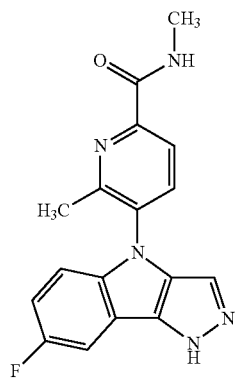 [SMILES: CNC(=O)c1ccc(-n2c3ccc(F)cc3c3[nH]ncc32)c(C)n1]

A TFA salt of the title compound was prepared by a method similar to EXAMPLE 117, using methanamine (2M in THF) in place of tert-butyl azetidin-3-ylcarbamate. $^1$H NMR (400 MHz, DMSO-d$_6$) δ ppm 2.38 (s, 3 H), 2.87 (d, J=4.80 Hz, 3 H), 7.13-7.18 (m, 2 H), 7.68-7.71 (m, 2 H), 8.03-8.04 (m, 2 H), 8.75 (d, J=5.30 Hz, 1 H). MS [M+H]$^+$ calc'd for C$_{17}$H$_{14}$FN$_5$O, 324.13; found 324.3.

Example 120

5-(7-Fluoropyrazolo[4,3-b]indol-4(1H)-yl)-N-(2-hydroxyethyl)-N,6-dimethylpicolinamide

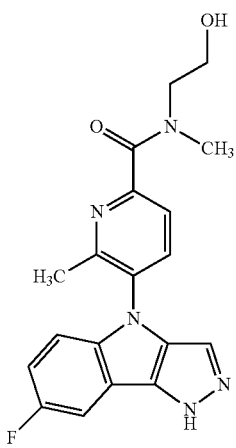 [SMILES: Cc1nc(C(=O)N(C)CCO)ccc1-n1c2ccc(F)cc2c2[nH]ncc21]

A TFA salt of the title compound was prepared by a method similar to EXAMPLE 117, using 2-(methylamino)ethanol in place of tert-butyl azetidin-3-ylcarbamate. $^1$H NMR (400 MHz, DMSO-d$_6$) δ ppm 2.29-2.31 (m, 3 H), 3.07 (d, J=8.08 Hz, 3 H), 3.47 (d, J=5.31 Hz, 2 H), 3.55-3.61 (m, 6 H), 3.66 (d, J=6.06 Hz, 4 H), 7.11-7.19 (m, 2 H), 7.55 (d, J=8.08 Hz, 1 H), 7.67-7.70 (m, 2 H), 7.98 (d, J=8.08 Hz, 1 H). MS [M+H]$^+$ calc'd for C$_{19}$H$_{18}$FN$_5$O$_2$, 368.15; found 368.3.

Example 121

N-(Cyanomethyl)-5-(7-fluoropyrazolo[4,3-b]indol-4(1H)-yl)-N,6-dimethylpicolinamide

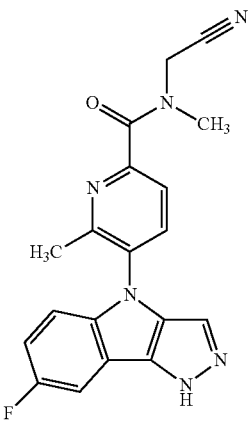 [SMILES: Cc1nc(C(=O)N(C)CC#N)ccc1-n1c2ccc(F)cc2c2[nH]ncc21]

A TFA salt of the title compound was prepared by a method similar to EXAMPLE 117, using 2-(methylamino)acetonitrile in place of tert-butyl azetidin-3-ylcarbamate. $^1$H NMR (400 MHz, DMSO-d$_6$) δ ppm 2.36 (d, J=7.07 Hz, 3 H), 3.21 (s, 2 H), 7.20 (t, J=6.32 Hz, 2 H), 7.69-7.72 (m, 2 H), 8.04 (d, J=8.08 Hz, 1 H). MS [M+H]$^+$ calc'd for C$_{19}$H$_{15}$FN$_6$O, 363.14; found 363.3.

Example 122

N-(2-Cyanoethyl)-5-(7-fluoropyrazolo[4,3-b]indol-4(1H)-yl)-6-methylpicolinamide

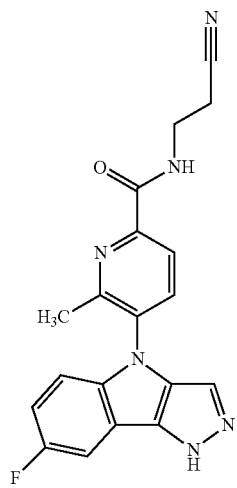 [SMILES: Cc1nc(C(=O)NCCC#N)ccc1-n1c2ccc(F)cc2c2[nH]ncc21]

A TFA salt of the title compound was prepared by a method similar to EXAMPLE 117, using 3-aminopropanenitrile in place of tert-butyl azetidin-3-ylcarbamate. $^1$H NMR (400 MHz, DMSO-d$_6$) δ ppm 2.41 (s, 3 H), 2.86 (t, J=6.57 Hz, 3 H), 3.62 (d, J=2.53 Hz, 3 H), 7.17-7.20 (m, 2 H), 7.69-7.72 (m, 2 H), 8.07 (d, J=1.01 Hz, 2 H), 9.12 (s, 1 H). MS [M+H]$^+$ calc'd for C$_{19}$H$_{15}$FN$_6$O, 363.14; found 363.3.

Example 123

5-(7-Fluoropyrazolo[4,3-b]indol-4(1H)-yl)-N—((R)-2-hydroxypropyl)-6-methylpicolinamide

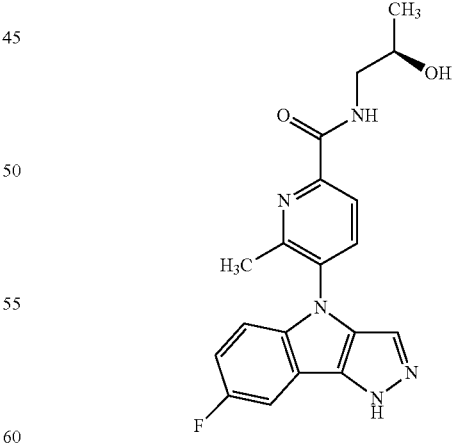

A TFA salt of the title compound was prepared by a method similar to EXAMPLE 117, using (R)-1-aminopropan-2-ol in place of tert-butyl azetidin-3-ylcarbamate. 1H NMR (400 MHz, CD$_3$OD) δ ppm 1.24 (d, J=6.32 Hz, 3 H), 2.42 (s, 3 H), 3.35-3.41 (m, 1 H), 3.52-3.59 (m, 1 H), 3.98-4.03 (m, 1 H), 4.22-4.29 (m, 1 H), 7.08-7.12 (m, 1 H), 7.12-7.18 (m, 1 H), 7.54 (d, J=2.02 Hz, 1 H), 7.65 (dd, J=8.72, 2.40 Hz, 1 H), 8.02 (d, J=8.34 Hz, 1 H), 8.11-8.15 (m, 1 H). MS [M+H]+ calc'd for C19H18FN5O2, 368.15; found 368.4.

Example 124

N-(2-Amino-2-oxoethyl)-5-(7-fluoropyrazolo[4,3-b]indol-4(1H)-yl)-6-methylpicolinamide

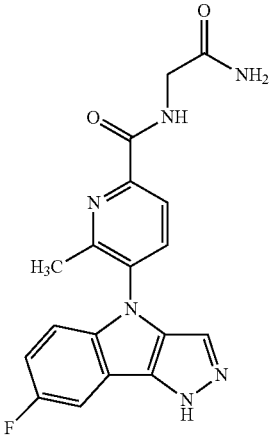 [SMILES: Cc1nc(C(=O)NCC(N)=O)ccc1-n1c2ccc(F)cc2c2[nH]ncc21]

A TFA salt of the title compound was prepared by a method similar to EXAMPLE 117, using 2-aminoacetamide hydrochloride in place of tert-butyl azetidin-3-ylcarbamate. 1H NMR (400 MHz, CD3OD) δ ppm 2.43 (s, 3 H), 4.14 (s, 2 H), 7.08-7.12 (m, 1 H), 7.14 (dd, J=9.09, 2.53 Hz, 1 H), 7.54 (s, 1 H), 7.65 (dd, J=8.72, 2.15 Hz, 1 H), 8.02 (d, J=8.34 Hz, 1 H), 8.14 (d, J=8.08 Hz, 1 H). MS [M+H]+ calc'd for C18H15FN6O2, 367.13; found 367.3.

Example 125

1-(5-(7-Fluoropyrazolo[4,3-b]indol-4(1H)-yl)-6-methylpicolinoyl)azetidine-3-carbonitrile

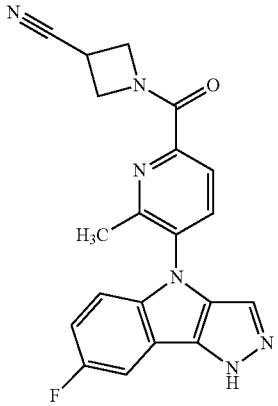 [SMILES: Cc1nc(C(=O)N2CC(C#N)C2)ccc1-n1c2ccc(F)cc2c2[nH]ncc21]

A TFA salt of the title compound was prepared by a method similar to EXAMPLE 117, using azetidine-3-carbonitrile hydrochloride in place of tert-butyl azetidin-3-ylcarbamate. 1H NMR (400 MHz, CD3OD) δ ppm 2.41 (s, 3 H),  4.36-4.41 (m, 2 H), 4.50-4.57 (m, 2 H), 7.10-7.17 (m, 2 H), 7.53 (d, J=8.08 Hz, 1 H), 7.63-7.66 (m, 1 H), 8.00 (d, J=8.34 Hz, 1 H), 8.08 (d, J=7.58 Hz, 1 H). MS [M+H]+ calc'd for C20H15FN6O, 375.14; found 375.4.

Example 126

5-(7-Fluoropyrazolo[4,3-b]indol-4(1H)-yl)-N-((2S)-2-hydroxypropyl)-6-methylpicolinamide

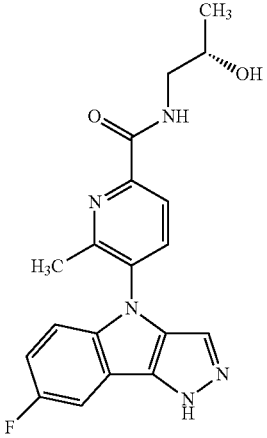 [SMILES: Cc1nc(C(=O)NC[C@H](C)O)ccc1-n1c2ccc(F)cc2c2[nH]ncc21]

A TFA salt of the title compound was prepared by a method similar to EXAMPLE 117, using (S)-1-aminopropan-2-ol in place of tert-butyl azetidin-3-ylcarbamate. 1H NMR (400 MHz, CD3OD) δ ppm 1.24 (d, J=6.32 Hz, 3 H), 2.42 (s, 3 H), 3.35-3.41 (m, 1 H), 3.53-3.59 (m, 1 H), 4.00 (dd, J=10.86, 6.82 Hz, 1 H), 7.08-7.12 (m, 1 H), 7.12-7.18 (m, 1 H), 7.55 (d, J=2.02 Hz, 1 H), 7.65 (dd, J=8.72, 2.40 Hz, 1 H), 8.02 (d, J=8.08 Hz, 1 H), 8.14 (d, J=8.08 Hz, 1 H). MS [M+H]+ calc'd for C19H18FN5O2, 368.15; found 368.4.

Example 127

1-(5-(7-Fluoropyrazolo[4,3-b]indol-4(1H)-yl)-4-methylpyrimidin-2-yl)azetidin-3-ol

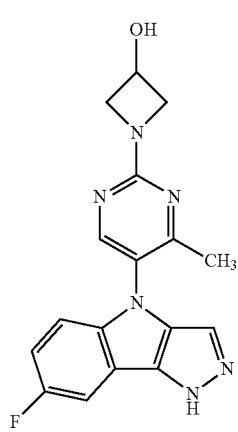 [SMILES: Cc1nc(N2CC(O)C2)ncc1-n1c2ccc(F)cc2c2[nH]ncc21]

To a 40 mL vial were added copper(I) trifluoromethanesolfonate toluene complex (14.67 mg, 0.028 mmol), 4,7-dichloro-1,10-phenanthroline (7.06 mg, 0.028 mmol)

and N-methyl-2-pyrrolidinone (1 mL). The resulting tan suspension was stirred at 125° C. under nitrogen overnight. After cooling to room temperature, 7-fluoro-1-(tetrahydro-2H-pyran-2-yl)-1,4-dihydropyrazolo[4,3-b]indole (73.5 mg, 0.284 mmol), 1-(5-bromo-4-methylpyrimidin-2-yl)azetidin-3-ol (118 mg, 0.482 mmol) and potassium 2-methylpropan-2-olate (36.8 mg, 0.312 mmol) were added. The mixture was heated at 125° C. under nitrogen for 8 days. The reaction mixture was subsequently diluted with water and extracted with EtOAc. The organic phase was washed with brine, dried over MgSO$_4$, and concentrated. The residue was dissolved in MeOH (4 mL) and treated with concentrated HCl (3 drops). The mixture was stirred at room temperature overnight and subsequently purified via preparative HPLC, eluting with 20-55% ACN (containing 0.035% TFA) in water (containing 0.05% TFA). The pure fractions were combined to give a TFA salt of the title compound (7.9 mg, 8.2%). $^1$H NMR (400 MHz, CD$_3$OD) δ ppm 2.07 (s, 3 H), 3.97-4.07 (m, 2 H), 4.41-4.51 (m, 2 H), 4.68-4.77 (m, 1 H), 6.95-7.08 (m, 1 H), 7.08-7.18 (m, 1 H), 7.50 (s, 1 H), 7.61 (dd, J=8.84, 2.53 Hz, 1 H), 8.34 (s, 1 H). MS [M+H]$^+$ calc'd for C$_{17}$H$_{15}$FN$_6$O, 339.14; found 339.3.

Example 128

6-Chloro-4-(5-methyl-3H-imidazo[4,5-b]pyridin-6-yl)-1,4-dihydropyrazolo[4,3-b]indole

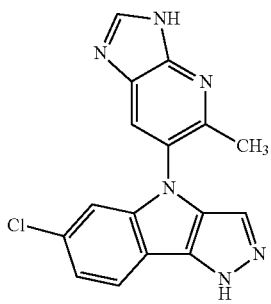 [SMILES: Cc1nc2[nH]cnc2cc1-n1c2cc(Cl)ccc2c2[nH]ncc21]

Step A: 2-Azido-1-bromo-4-chlorobenzene

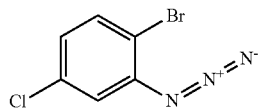 [SMILES: [N-]=[N+]=Nc1cc(Cl)ccc1Br]

To a 500 mL round-bottom flask were added 2-bromo-5-chloroaniline (8.83 g, 43.08 mmol, 1.0 eq), concentrated HCl (7.54 mL) and water (80 mL) and the resulting mixture was stirred at 0° C. for 20 minutes. A solution of NaNO$_2$ (2.97 g, 1.0 eq) in water (20 mL) was added dropwise while maintaining the temperature below 5° C. Following the addition, the mixture was stirred at this temperature for 20 minutes. Next, a solution of NaN$_3$ (2.80 g, 1.0 eq) in water (35 mL) was added dropwise while maintaining the internal temperature of the reaction below 5° C. The reaction mixture was stirred at 0° C. for 30 minutes and then at room temperature for 3 hours. The reaction mixture was extracted into EtOAc and the organic layer was separated, dried over Na$_2$SO$_4$, filtered, and concentrated to give crude title compound, which was used without further purification (9 g, 90%). $^1$HNMR (300 MHz, CDCl$_3$) δ ppm 7.48 (d, 1H, J=8.4 Hz), 7.17 (d, 1H, J=2.1 Hz), 7.01 (dd, 1H, J=8.4 Hz, 2.4 Hz).

Step B: 5-(2-Azido-4-chlorophenyl)-1-(tetrahydro-2H-pyran-2-yl)-1H-pyrazole

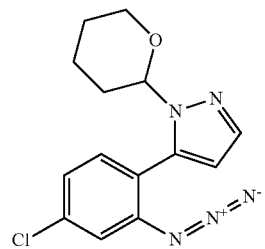 [SMILES: [N-]=[N+]=Nc1cc(Cl)ccc1-c1ccnn1C1CCCCO1]

To a three-neck flask were added 2-azido-1-bromo-4-chlorobenzene (2 g, 4.63 mmol, 1.0 eq), 2-(1-(2H-3,4,5,6-tetrahydropyran-2-yl)pyrazol-5-yl)-4,4,5,5-tetramethyl-1,3,2-dioxaborolane (2.88 g, 1.2 eq), (Ph$_3$P)$_4$Pd (0.50 g, 0.05 eq), Na$_2$CO$_3$ (2.20 g, 2.4 eq), DME (40 mL), and water (2 mL). The reaction mixture was refluxed overnight and then cooled to room temperature, concentrated, and partitioned between water and EtOAc. The layers were separated and the organic layer was washed with brine, dried over Na$_2$SO$_4$, filtered, and concentrated to an oil, which was purified via flash chromatography, eluting with EtOAc and petroleum ether (1:10) to give the title compound as an oil (1 g). [M+H]$^+$ calc'd for C$_{14}$H$_{14}$ClN$_5$O, 304.10; found 304.

Step C: 6-Chloro-1-(tetrahydro-2H-pyran-2-yl)-1,4-dihydropyrazolo[4,3-b]indole

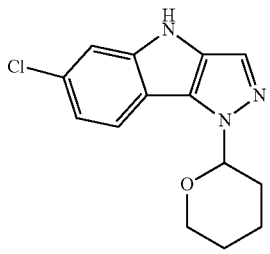 [SMILES: Clc1ccc2c(c1)[nH]c1cnn(C3CCCCO3)c12]

A solution of 5-(2-azido-4-chlorophenyl)-1-(tetrahydro-2H-pyran-2-yl)-1H-pyrazole in 1,2-dichlorobenzene was heated to 170° C. for 2 hours. The reaction mixture was cooled to room temperature and concentrated to an oil, which was purified via flash chromatography, eluting with EtOAc and petroleum ether (1:5) to give the title compound (0.3 g). $^1$HNMR (400 MHz, DMSO-d$_6$) δ ppm 10.83 (s, 1H), 7.84 (d, 1H, J=8.4 Hz), 7.53 (s, 1H), 7.45 (d, 1H, J=2.0 Hz), 7.11 (dd, 1H, J=8.4 Hz, 2.0 Hz), 5.74 (dd, 1H, J=9.2 Hz, 2.4 Hz), 3.98-3.95 (m, 1H), 3.82-3.75 (m, 1H), 2.21-2.16 (m, 1H), 2.00-1.97 (m, 2H), 1.79-1.75 (m, 1H), 1.67-1.61 (m, 2H).

Step D: 6-Chloro-4-(5-methyl-3-((2-(trimethylsilyl) ethoxy)methyl)-3H-imidazo[4,5-b]pyridin-6-yl)-1-(tetrahydro-2H-pyran-2-yl)-1,4-dihydropyrazolo[4,3-b]indole

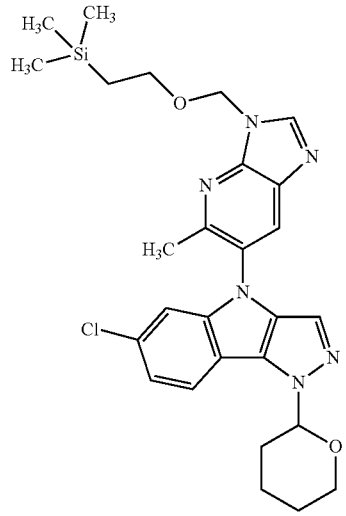 [SMILES: Cc1nc2c(cc1-n1c3cc(Cl)ccc3c3c1cnn3C1CCCCO1)ncn2COCC[Si](C)(C)C]

A mixture of 6-chloro-1-(tetrahydro-2H-pyran-2-yl)-1,4-dihydropyrazolo[4,3-b]indole (160 mg, 0.58 mmol, 1.0 eq), 6-bromo-5-methyl-3-((2-(trimethylsilyl)ethoxy)methyl)-3H-imidazo[4,5-b]pyridine (595 mg, 1.0 eq), (1S,2S)—N1,N2-dimethylcyclohexane-1,2-diamine (868 mg, 3 eq), CuI (222 mg, 2 eq), Cs$_2$CO$_3$ (569 mg, 3 eq) and DMA (6 mL) was stirred at 180° C. under N$_2$ for 16 hours. The reaction mixture was subsequently diluted with water (6 mL), extracted with EtOAc (3×15 mL), and washed with brine. The organic layer was dried over Na$_2$SO$_4$, concentrated, and purified by preparative HPLC to give the title compound (30 mg, 9.6%). [M+H]$^+$ calc'd for C$_{27}$H$_{33}$ClN$_6$O$_2$Si, 537.22; found 537.

Step E: 6-Chloro-4-(5-methyl-3H-imidazo[4,5-b] pyridin-6-yl)-1,4-dihydropyrazolo[4,3-b]indole To a solution of 6-chloro-4-(5-methyl-3-((2-(trimethylsilyl)ethoxy)methyl)-3H-imidazo[4,5-b]pyridin-6-yl)-1-(tetrahydro-2H-pyran-2-yl)-1,4-dihydropyrazolo[4,3-b]indole (30 mg) in ethanol (4 mL) was added concentrated aqueous HCl (1 mL). The reaction mixture was heated at 40° C. for 3 hours, concentrated, and its pH adjusted to 8 by saturated aqueous NaHCO$_3$. The mixture was subsequently extracted with EtOAc (3×20 mL), washed with brine, and concentrated to give the title compound as a white solid (15 mg, 83%). $^1$HNMR (400 MHz, CD$_3$OD) δ ppm 9.12 (s, 1H), 8.26 (s, 1H), 7.84-7.82 (m, 1H), 7.42 (s, 1H), 7.15-7.13 (m, 1H), 6.98 (s, 1H), 2.30 (s, 3H). [M+H]$^+$ calc'd for C$_{16}$H$_{11}$ClN$_6$, 323.08; found 323.

Example 129

6-Chloro-7-fluoro-4-(5-methyl-3H-imidazo[4,5-b] pyridin-6-yl)-1,4-dihydropyrazolo[4,3-b]indole

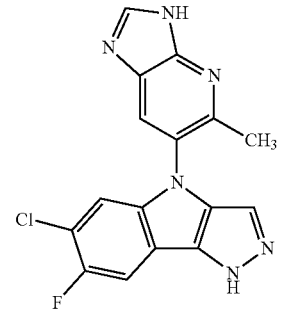 [SMILES: Cc1nc2[nH]cnc2cc1-n1c2cc(Cl)c(F)cc2c2[nH]ncc21]

The title compound was prepared by a method similar to EXAMPLE 128, using 2-bromo-5-chloro-4-fluoroaniline in place of 2-bromo-5-chloroaniline. $^1$H NMR (400 MHz, CD$_3$OD) δ ppm 9.53 (s, 1H), 8.45 (s, 1H), 7.91 (s, 1H), 7.82 (d, 1H, J=8.8 Hz), 7.28 (d, 1H, J=6.0 Hz), 2.35 (s, 3H). MS [M+H]$^+$ calc'd for C$_{16}$H$_{10}$ClFN$_6$, 341.07; found 341.0.

Example 130

6,7-Difluoro-4-(5-methyl-3H-imidazo[4,5-b]pyridin-6-yl)-1,4-dihydropyrazolo[4,3-b]indole

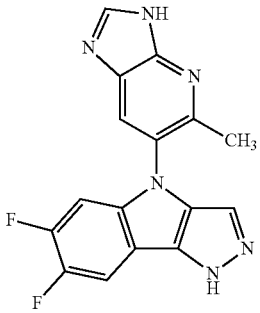 [SMILES: Cc1nc2[nH]cnc2cc1-n1c2cc(F)c(F)cc2c2[nH]ncc21]

The title compound was prepared by a method similar to EXAMPLE 128, using 2-bromo-4,5-difluoroaniline in place of 2-bromo-5-chloroaniline. $^1$H NMR (400 MHz, CD3OD) δ ppm 9.53 (s, 1H), 8.48 (s, 1H), 7.90-7.85 (m, 1H), 7.62 (s, 1H), 7.13-7.09 (m, 1H), 2.46 (s, 3H). MS [M+H]$^+$ calc'd for C$_{16}$H$_{10}$F$_2$N$_6$, 325.10; found 325.1.

Example 131

7-Fluoro-6-methyl-4-(5-methyl-1H-imidazo[4,5-b] pyridin-6-yl)-1,4-dihydropyrazolo[4,3-b]indole

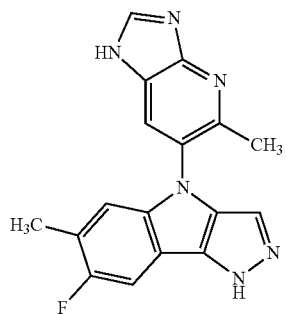 [SMILES: Cc1cc2c(cc1F)c1[nH]ncc1n2-c1cc2[nH]cnc2nc1C]

The title compound was prepared by a method similar to EXAMPLE 128, using 2-bromo-4-fluoro-5-methylaniline in place of 2-bromo-5-chloroaniline. $^1$H NMR (400 MHz, CD$_3$OD) δ ppm 8.45 (s, 1H), 8.07 (s, 1H), 7.56-7.58 (m, 1H), 7.41 (s, 1H), 6.80-6.82 (m, 1H), 2.30 (s, 6H). MS [M+H]$^+$ calc'd for C$_{17}$H$_{13}$FN$_6$, 321.13; found 321.1.

Example 132

7-Fluoro-4-(1-phenylethyl)-1,4-dihydropyrazolo[4,3-b]indole

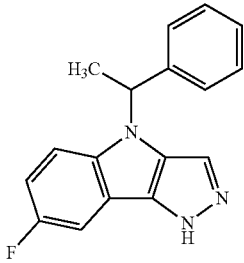 [SMILES: CC(c1ccccc1)n1c2ccc(F)cc2c2[nH]ncc21]

To an 8 mL vial was added 7-fluoro-1-(tetrahydro-2H-pyran-2-yl)-1,4-dihydropyrazolo[4,3-b]indole (50 mg, 0.193 mmol) and sodium hydride (4.63 mg, 0.193 mmol) in DMF (1 mL) to give a red solution. The solution was stirred for 30 minutes. (1-Bromoethyl)benzene (35.7 mg, 0.193 mmol) was added, and the reaction mixture was heated at 80° C. overnight. LC/MS showed the reaction was partially complete with some starting material remaining. The reaction mixture was partitioned between EtOAc and water. The layers were separated and the aqueous layer was back-extracted with EtOAc. The organic layers were combined, washed with brine, and concentrated. Methanol (3 mL) and HCl (2 drops) were added, and the reaction mixture was heated at 60° C. for 3 hours. LC/MS showed the reaction was complete. The crude product was purified by preparative HPLC and eluted with 65-90% ACN in 0.05% aqueous TFA. The pure fractions were lyophilized to yield a TFA salt of the title compound as a clear semisolid (27.1 mg, 50.3%). $^1$H NMR (400 MHz, CD$_3$OD) δ ppm 1.98 (d, J=7.07 Hz, 3 H), 5.77 (s, 1 H), 7.11 (d, J=2.78 Hz, 1 H), 7.23-7.30 (m, 5 H), 7.35 (d, J=4.04 Hz, 1 H), 7.50 (s, 1 H), 7.52-7.57 (m, 1 H). MS [M+H]$^+$ calc'd for C$_{17}$H$_{14}$FN$_3$, 280.13; found 280.3.

Example 133

7-Fluoro-4-(2-methyl-6-(2-(methylsulfonyl)ethyl)pyridin-3-yl)-1,4-dihydropyrazolo[4,3-b]indole

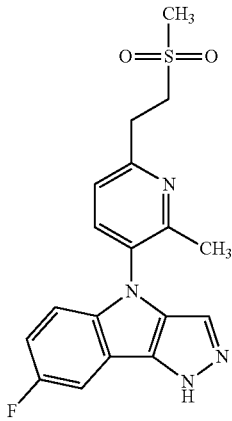 [SMILES: Cc1nc(CCS(C)(=O)=O)ccc1-n1c2ccc(F)cc2c2[nH]ncc21]

Step A: 4-(6-(benzyloxy)-2-methylpyridin-3-yl)-7-fluoro-1-(tetrahydro-2H-pyran-2-yl)-1,4-dihydropyrazolo[4,3-b]indole

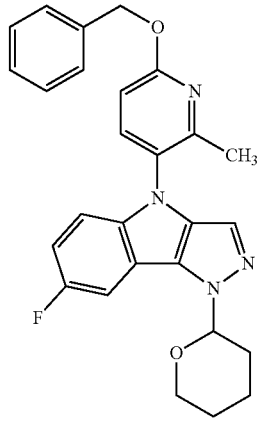 [SMILES: Cc1nc(OCc2ccccc2)ccc1-n1c2ccc(F)cc2c2c1cnn2C1CCCCO1]

A 50 mL round-bottom flask equipped with reflux condenser and magnetic stir bar was charged with 7-fluoro-1-(tetrahydro-2H-pyran-2-yl)-1,4-dihydropyrazolo[4,3-b]indole (1.695 g, 6.54 mmol), 6-(benzyloxy)-3-bromo-2-methylpyridine (2 g, 7.19 mmol), ((thiophene-2-carbonyl)oxy)copper (0.125 g, 0.654 mmol) and Cs$_2$CO$_3$ (6.39 g, 19.61 mmol) in DMF (15 mL) to give a brown suspension. The solvent was purged with N$_2$ and the reaction mixture was heated in an oil bath for 18 hours at 160° C. The mixture was subsequently partitioned between water (100 mL) and ethyl acetate (100 mL). The organic layer was washed with water, dried over Na$_2$SO$_4$, concentrated, and purified by flash chromatography. The product-containing fractions were combined and concentrated to give the title compound (0.96 g, 32%).

Step B: 5-(7-Fluoro-1-(tetrahydro-2H-pyran-2-yl)pyrazolo[4,3-b]indol-4(1H)-yl)-6-methylpyridin-2(1H)-one

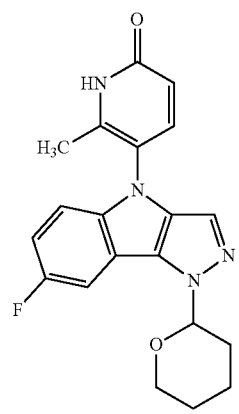 [SMILES: Cc1[nH]c(=O)ccc1-n1c2ccc(F)cc2c2c1cnn2C1CCCCO1]

To 4-(6-(benzyloxy)-2-methylpyridin-3-yl)-7-fluoro-1-(tetrahydro-2H-pyran-2-yl)-1,4-dihydropyrazolo[4,3-b]indole (0.96 g, 2.103 mmol) in a mixture of MeOH and THF (4:1, 15 mL) was added Pd (10%) on activated carbon (0.4 g, 2.103 mmol). The reaction mixture was stirred for 18 hours at room temperature under hydrogen atmosphere using a balloon. The reaction mixture was filtered through a pad of Celite. The volatiles were evaporated and purified by flash chromatography (120 g silica column) eluting with 10-80% EtOAc in heptane for 30 minutes and then 15% MeOH in DCM. The product-containing fractions were combined and concentrated to give the title compound as an off-white solid (0.594 g, 77%).

Step C: 4-(6-Chloro-2-methylpyridin-3-yl)-7-fluoro-1,4-dihydropyrazolo[4,3-b]indole

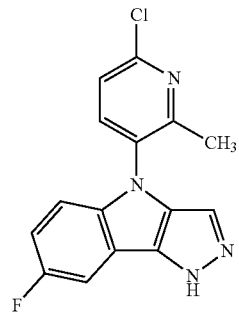

To 5-(7-fluoro-1-(tetrahydro-2H-pyran-2-yl)pyrazolo[4,3-b]indol-4(1H)-yl)-6-methylpyridin-2(1H)-one (0.39 g, 1.064 mmol) in POCl₃ (10 mL) was added pentachlorophosphorane (0.443 g, 2.129 mmol). The reaction mixture was heated at 120° C. for 3 days. The reaction mixture was subsequently cooled to RT and poured on to ice containing saturated aq NaHCO₃ (100 mL) and EtOAc (100 mL). Solid NaHCO₃ (10 g) was added to the solution, which was allowed to warm to room temperature. The organic layer was separated, washed with saturated aq NaHCO₃, water, and brine, dried over Na₂SO₄, and then concentrated. The product was purified by preparative HPLC, eluting with ACN (containing 10 mM NH₄HCO₃) in water). The product-containing fractions were combined and the volatiles evaporated to give the title compound (0.03 g, 9%).

Step D: 7-Fluoro-4-(2-methyl-6-(2-(methylsulfonyl)ethyl)pyridin-3-yl)-1,4-dihydropyrazolo[4,3-b]indole A sealable tube was charged with 4-(6-chloro-2-methylpyridin-3-yl)-7-fluoro-1,4-dihydropyrazolo[4,3-b]indole (0.03 g, 0.1 mmol), potassium vinyl trifluoroborate (0.029 g, 0.219 mmol), Et₃N (0.028 mL, 0.200 mmol) and PdCl₂(dppf) (7.30 mg, 9.98 μmol) in IPA (3 mL) to give a light-brown suspension. The mixture was bubbled with nitrogen and heated at 100° C. for 30 minutes in an oil bath. Sodium methanesulfinate (0.051 g, 0.499 mmol) and acetic acid (0.057 mL, 0.998 mmol) were added to the reaction mixture, which was subsequently stirred at 60° C. for 18 hours. The reaction mixture was cooled and the volatiles evaporated. The crude residue was dissolved in EtOAc, washed with brine, water, and again with brine, dried over Na₂SO₄, and concentrated. The crude residue was purified by LCMS eluting with 35% acetonitrile (containing 10 mM NH₄HCO₃) in water. The product-containing fractions were combined and the volatiles evaporated to give the title compound (0.0148 g, 39.8%). ¹H NMR (400 MHz, CD₃OD) δ ppm 2.31 (s, 3 H), 3.06 (s, 3 H), 3.35-3.44 (m, 2 H), 3.60-3.72 (m, 2 H), 7.01 (dd, J=8.97, 4.17 Hz, 1 H), 7.13 (td, J=9.09, 2.78 Hz, 1 H), 7.39-7.51 (m, 2 H), 7.64 (d, J=7.33 Hz, 1 H), 7.80 (d, J=8.08 Hz, 1 H). MS [M+H]⁺ calc'd for C₁₈H₁₇FN₄O₂S, 373.11; found 373.43.

Example 134

(1-(Difluoromethyl)-4-(7-fluoropyrazolo[4,3-b]indol-4(1H)-yl)-1H-pyrazol-3-yl)methanol

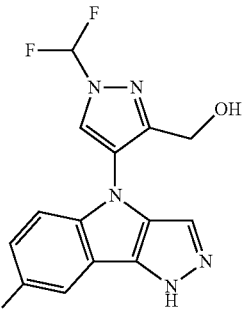

Step A: Ethyl 4-bromo-1H-pyrazole-5-carboxylate

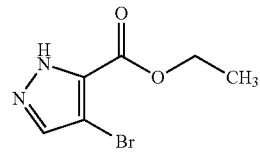

To a solution of 4-bromo-1H-pyrazole-5-carboxylic acid (1 g, 5.2 mmol) in EtOH (20 mL) was added concentrated H₂SO₄ (1 mL). The mixture was refluxed for 12 hours. The solvent was removed on a rotary evaporator. The resulting residue was neutralized with saturated aq NaHCO₃ and extracted with EtOAc (2×50 mL). The organic layers were combined, washed with brine (50 mL), dried, and concentrated to give the title compound, which was used directly in the next step (900 mg, 79%). ¹H NMR (400 MHz, DMSO-d₆) δ ppm 13.85 (br, 1H), 8.14 (br, 1H), 4.30 (t, J=7.2 Hz, 1H), 1.30 (t, J=7.2 Hz, 1H).

Step B: Ethyl 4-bromo-1-(difluoromethyl)-1H-pyrazole-3-carboxylate

To a solution of ethyl 4-bromo-1H-pyrazole-5-carboxylate (740 mg, 3.38 mmol) in acetonitrile (15 mL) were added sodium 2-chloro-2,2-difluoroacetate (1.03 g, 6.76 mmol), 18-crown-6 (50 mg) and K₂CO₃ (932 mg, 6.76 mmol). The reaction mixture was refluxed for 2 hours, then quenched with water (30 mL) and extracted with EtOAc (2×30 mL). The organic layers were combined, washed with brine (50 mL), dried, and concentrated. The crude product was purified by silica gel column chromatography, eluting with EtOAc/Hexane (1:50 to 1:10) to give the title compound and a regioisomer, ethyl 4-bromo-1-(difluoromethyl)-1H-pyrazole-5-carboxylate. $^1$H NMR (400 MHz, DMSO-d$_6$) δ ppm 8.77 (s, 1H), 7.91 (t, J=18.4 Hz, 1H), 4.34 (t, J=7.2 Hz, 1H), 1.32 (t, J=7.2 Hz, 1H) (title compound); $^1$H NMR (400 MHz, DMSO-d$_6$) δ ppm 8.15 (s, 1H), 8.08 (t, J=18.0 Hz, 1H), 4.40 (t, J=7.2 Hz, 1H), 1.35 (t, J=7.2 Hz, 1H) (regioisomer).

Step C: (4-Bromo-1-(difluoromethyl)-1H-pyrazol-3-yl)methanol

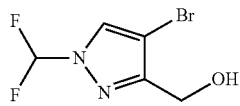

To a stirred solution of ethyl 4-bromo-1-(difluoromethyl)-1H-pyrazole-3-carboxylate (500 mg, 1.86 mmol) in MeOH (50 mL) was added NaBH$_4$ (3.53 g, 93 mmol) in portions. The reaction mixture was stirred at room temperature for 2 hours, then quenched with water (50 mL), and extracted into DCM (2×100 mL). The organic layers were combined, washed with brine (50 mL), dried, and concentrated to give the title compound (400 mg, 95%). $^1$H NMR (400 MHz, DMSO-d$_6$) δ ppm 8.50 (s, 1H), 7.75 (t, J=18.8 Hz, 1H), 5.31 (t, J=5.6 Hz, 1H), 4.44 (t, J=5.6 Hz, 2H).

Step D: (1-(Difluoromethyl)-4-(7-fluoro-1-(tetrahydro-2H-pyran-2-yl)pyrazolo[4,3-b]indol-4(1H)-yl)-1H-pyrazol-3-yl)methanol

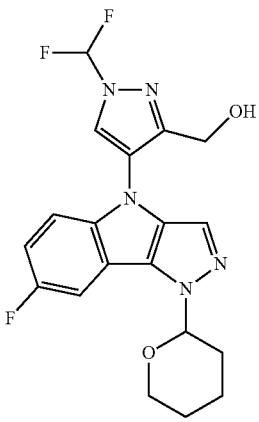 [SMILES: OCc1nn(C(F)F)cc1-n1c2ccc(F)cc2c2c1cnn2C1CCCCO1]

To a solution of (4-bromo-1-(difluoromethyl)-1H-pyrazol-3-yl)methanol (159 mg, 0.7 mmol) and 7-fluoro-1-(tetrahydro-2H-pyran-2-yl)-1,4-dihydropyrazolo[4,3-b]indole (181 mg, 0.7 mmol) in DMSO (3 mL) were added K$_2$CO$_3$ (193 mg, 1.4 mmol), CuI (17 mg, 0.14 mmol), and L-Proline (16 mg, 0.14 mmol) under N$_2$ at room temperature. The reaction vessel was sealed and heated in microwave at 150° C. for 3 hours. The reaction was subsequently quenched with water (20 mL) and the mixture extracted with EtOAc (2×30 mL). The organic layers were combined, washed with brine (50 mL), dried, and concentrated. The crude product was purified by preparative TLC (PE/EtOAc=5:1) to give the title compound (105 mg, 45%).

Step E: (1-(Difluoromethyl)-4-(7-fluoropyrazolo[4,3-b]indol-4(1H)-yl)-1H-pyrazol-3-yl)methanol To a solution of (1-(difluoromethyl)-4-(7-fluoro-1-(tetrahydro-2H-pyran-2-yl)pyrazolo[4,3-b]indol-4(1H)-yl)-1H-pyrazol-3-yl)methanol (105 mg, 0.26 mmol) in dioxane (5 mL) was added HCl/dioxane (5 mL) at 0° C. The reaction mixture was stirred at room temperature for 2 hours, then concentrated and purified by preparative HPLC to give the title compound (24.75 mg). $^1$H NMR (400 MHz, DMSO-d$_6$) δ ppm 13.14 (br, 1H), 8.69 (s, 1H), 7.85 (t, J=18.8 Hz, 1H), 7.84-7.70 (m, 2H), 7.20-7.15 (m, 2H), 5.15 (t, J=5.2 Hz, 1H), 4.39 (t, J=5.2 Hz, 2H). MS [M+H]$^+$ calc'd for C$_{14}$H$_{10}$F$_3$N$_5$O, 322.09; found 322.1.

Example 135

(1R,2R,5S)-3-(5-(7-Fluoropyrazolo[4,3-b]indol-4 (1H)-yl)-4-methylpyrimidin-2-yl)-3-azabicyclo [3.1.0]hexane-2-carboxamide

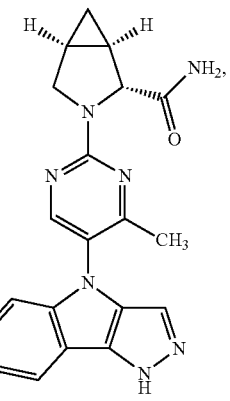

Example 136

(1R,2S,5S)-3-(5-(7-Fluoropyrazolo[4,3-b]indol-4 (1H)-yl)-4-methylpyrimidin-2-yl)-3-azabicyclo [3.1.0]hexane-2-carboxamide

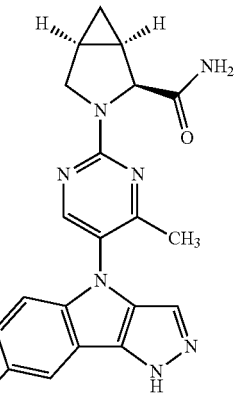

Step A: (1R,5S)-3-(5-bromo-4-methylpyrimidin-2-yl)-3-azabicyclo[3.1.0]hexane-2-carboxylic acid

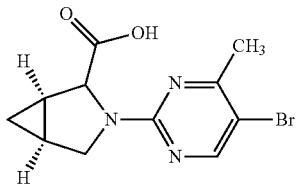 [SMILES: Cc1nc(N2C[C@H]3C[C@H]3C2C(=O)O)ncc1Br]

A 100 mL round-bottom flask was charged with 5-bromo-2-chloro-4-methylpyrimidine (3.09 g, 14.87 mmol), (1R,5S)-3-azabicyclo[3.1.0]hexane-2-carboxylic acid (2.08 g, 16.36 mmol), and Et$_3$N (6.22 mL, 44.6 mmol) in EtOH (70 mL) to give a yellow solution. The reaction mixture was stirred at 75° C. for 18 hours and then partitioned between 1N HCl (40 mL) and ethyl acetate (40 mL). The organic and aqueous layers were separated, and the aqueous layer was back-extracted with ethyl acetate (75 mL). The organic layers were combined, washed with brine (40 mL), dried over Na$_2$SO$_4$, filtered, and concentrated to give the title compound as a tan solid which was used without further purification (2.85 g, 64.3%).

Step B: (1R,5S)-3-(5-Bromo-4-methylpyrimidin-2-yl)-3-azabicyclo[3.1.0]hexane-2-carboxamide

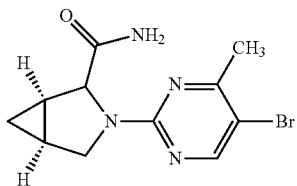 [SMILES: Cc1nc(N2C[C@H]3C[C@H]3C2C(N)=O)ncc1Br]

In a 100 mL round-bottom flask equipped with a magnetic stir bar were mixed (1R,5S)-3-(5-bromo-4-methylpyrimidin-2-yl)-3-azabicyclo[3.1.0]hexane-2-carboxylic acid (2.85 g, 9.56 mmol), ammonium chloride (0.767 g, 14.34 mmol), EDC (2.016 g, 10.52 mmol), HOBt (1.610 g, 10.52 mmol), and Et$_3$N (4.00 mL, 28.7 mmol) in DMF (20 mL). The resulting yellow suspension was left to stir over the weekend. Following reaction, a white solid was filtered off, washed with DMF (10 mL) and water (10 mL) and dried to give the title compound (900 mg, 31.7%).

Step C: (1R,2R,5S)-3-(5-(7-fluoropyrazolo[4,3-b]indol-4(1H)-yl)-4-methylpyrimidin-2-yl)-3-azabicyclo[3.1.0]hexane-2-carboxamide, and (1R,2S,5S)-3-(5-(7-fluoropyrazolo[4,3-b]indol-4(1H)-yl)-4-methylpyrimidin-2-yl)-3-azabicyclo[3.1.0]hexane-2-carboxamide In a 100 mL round-bottom flask equipped with a magnetic stir bar were mixed 7-fluoro-1-(tetrahydro-2H-pyran-2-yl)-1,4-dihydropyrazolo[4,3-b]indole (524 mg, 2.019 mmol), (1R,5S)-3-(5-bromo-4-methylpyrimidin-2-yl)-3-azabicyclo[3.1.0]hexane-2-carboxamide (900 mg, 3.03 mmol), ((thiophene-2-carbonyl)oxy)copper (38.5 mg, 0.202 mmol), and K$_2$CO$_3$ (837 mg, 6.06 mmol) in DMSO (20 mL). The resulting brown suspension was purged with nitrogen and stirred at 150° C. overnight under N$_2$. The reaction was then cooled and water (125 mL) was added. A light brown solid was filtered off and was washed with water (40 mL) and dried. The solid was dissolved in MeOH (30 mL), treated with concentrated HCl (1 mL), and heated to 70° C. for 2 hours. The reaction mixture was partitioned between saturated aq NaHCO$_3$ (50 mL) and ethyl acetate (150 mL). The organic and aqueous layers were separated, and the aqueous layer was back-extracted with ethyl acetate (125 mL). The organic layers were combined, washed with brine (100 mL), dried over Na$_2$SO$_4$, filtered, and concentrated to yield a brown solid. The solid was suspended in DCM (10 mL), filtered off, washed with DCM (5 mL), dried, and purified by preparative HPLC, eluting with a gradient of 25-50% ACN in water (containing 0.1% formic acid). The pure fractions were combined and concentrated. The diastereomers were separated using chiral chromatography to give the (1R,2R,5S)-stereoisomer (30.4 mg, 3.85%) and the (1R,2S,5S)-stereoisomer (28.3 mg, 3.58%). $^1$H NMR (400 MHz, CD$_3$OD) δ ppm 0.76-0.86 (m, 2 H), 1.85 (ddd, J=12.13, 7.58, 4.80 Hz, 1 H), 1.99-2.06 (m, 3 H), 2.10 (ddd, J=12.38, 7.96, 4.17 Hz, 1 H), 3.81 (dd, J=10.36, 5.31 Hz, 1 H), 3.94 (d, J=10.86 Hz, 1 H), 4.56 (d, J=5.31 Hz, 1 H), 6.98 (br s, 1 H), 7.11 (td, J=9.09, 2.78 Hz, 1 H), 7.44 (br s, 1 H), 8.29 (d, J=1.26 Hz, 1 H) ((1R,2R,5S)-stereoisomer); $^1$H NMR (400 MHz, CD$_3$OD) δ ppm 0.76-0.91 (m, 2 H), 1.82-1.89 (m, 1 H), 2.03 (d, J=1.52 Hz, 3 H), 2.05-2.13 (m, 1 H), 3.81 (dd, =11.12, 5.05 Hz, 1 H), 3.93 (d, J=11.12 Hz, 1 H), 4.56 (d, J=5.56 Hz, 1 H), 6.98 (br s, 1 H), 7.10 (td, J=9.09, 2.53 Hz, 1 H), 7.44 (br s, 1 H), 7.63 (br s, 1 H), 8.28 (d, J=1.26 Hz, 1 H) ((1R,2S,5S)-stereoisomer). MS [M+H]$^+$ calc'd for C$_{20}$H$_{18}$FN$_7$O, 392.16; found 392.4.

Example 137

7-Fluoro-4-(4-methyl-2-((S)-3-(methylsulfonyl)pyrrolidin-1-yl)pyrimidin-5-yl)-1,4-dihydropyrazolo[4,3-b]indole

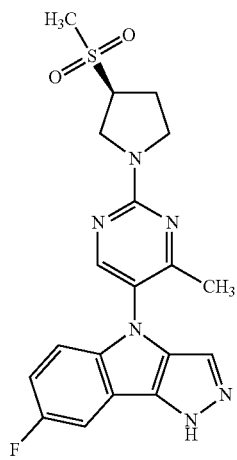 [SMILES: Cc1nc(N2CC[C@H](S(C)(=O)=O)C2)ncc1-n1c2ccc(F)cc2c2[nH]ncc21]

Step A: (S)-5-Bromo-4-methyl-2-(3-(methylsulfonyl)pyrrolidin-1-yl)pyrimidine

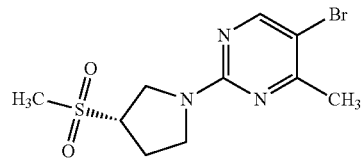

A 40 mL vial was charged with 5-bromo-2-chloro-4-methylpyrimidine (348 mg, 1.675 mmol), (S)-3-(methylsulfonyl)pyrrolidine (250 mg, 1.675 mmol), and Et₃N (0.701 mL, 5.03 mmol) in EtOH (90 mL). The resulting yellow solution was stirred at 75° C. for 3 days. The reaction mixture was partitioned between water (40 mL) and ethyl acetate (40 mL). The organic and aqueous layers were separated, and the aqueous layer was back-extracted with ethyl acetate (75 mL). The organic layers were combined, washed with brine (40 mL), dried over Na₂SO₄, filtered, and concentrated to give the title compound as a white solid, which was used without further purification (430 mg, 80%).

Step B: 7-Fluoro-4-(4-methyl-2-((S)-3-(methylsulfonyl)pyrrolidin-1-yl)pyrimidin-5-yl)-1,4-dihydropyrazolo[4,3-b]indole In a 25 mL tube equipped with a magnetic stir bar were mixed 7-fluoro-1-(tetrahydro-2H-pyran-2-yl)-1,4-dihydropyrazolo[4,3-b]indole (167 mg, 0.645 mmol), (S)-5-bromo-4-methyl-2-(3-(methylsulfonyl)pyrrolidin-1-yl)pyrimidine (310 mg, 0.968 mmol), ((thiophene-2-carbonyl)oxy)copper (12.31 mg, 0.065 mmol) and Cs₂CO₃ (631 mg, 1.936 mmol) in DMF (10 mL). The resulting brown suspension was purged with N₂, capped, and heated for 180° C. for 3 days. The reaction mixture was partitioned between water (50 mL) and ethyl acetate (50 mL). The organic and aqueous layers were separated and the aqueous layer was back-extracted with ethyl acetate (50 mL). The organic layers were combined, washed with brine (30 mL), dried over Na₂SO₄, filtered, and concentrated to yield a dark syrup. The residue was dissolved in MeOH, treated with concentrated HCl (10 drops), and left to stir overnight. The product was purified by preparative HPLC, eluting with a gradient of 25-50% ACN in water (containing 0.05% TFA). The pure fractions were lyophilized to give a TFA salt of the title compound as a tan solid (66.5 mg, 19.5%). ¹H NMR (400 MHz, CD₃OD) δ ppm 2.09 (s, 3 H), 2.49-2.65 (m, 2 H), 3.07 (s, 3 H), 3.78 (ddd, J=10.99, 7.96, 5.81 Hz, 1 H), 3.92 (dt, J=10.67, 7.42 Hz, 1 H), 4.01-4.13 (m, 2 H), 4.16-4.22 (m, 1 H), 7.03-7.07 (m, 1 H), 7.15 (td, J=9.09, 2.53 Hz, 1 H), 7.57 (br s, 1 H), 7.63 (dd, J=8.84, 2.53 Hz, 1 H), 8.36 (s, 1 H). MS [M+H]⁺ calc'd for $C_{19}H_{19}FN_6O_2S$, 415.14; found 415.3.

Example 138

(4-(7-Fluoropyrazolo[4,3-b]indol-4(1H)-yl)-1-methyl-1H-pyrazol-3-yl)methanol

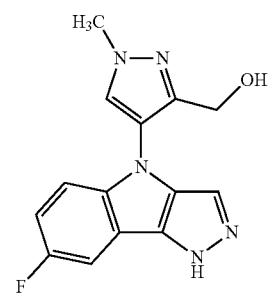 [SMILES: Cn1cc(-n2c3ccc(F)cc3c3[nH]ncc32)c(CO)n1]

Step A: 4-(7-Fluoro-1-(tetrahydro-2H-pyran-2-yl)pyrazolo[4,3-b]indol-4(1H)-yl)-1-methyl-1H-pyrazole-3-carboxylic acid

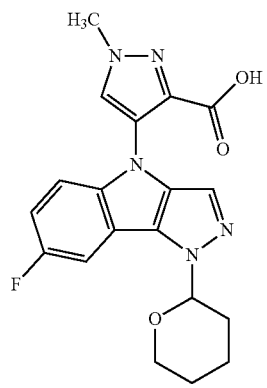 [SMILES: Cn1cc(-n2c3ccc(F)cc3c3c2cnn3C2CCCCO2)c(C(=O)O)n1]

In a 20 mL vial were mixed 7-fluoro-1-(tetrahydro-2H-pyran-2-yl)-1,4-dihydropyrazolo[4,3-b]indole (64 mg, 0.247 mmol), methyl 4-bromo-1-methyl-1H-pyrazole-3-carboxylate (92 mg, 0.420 mmol), ((thiophene-2-carbonyl)oxy) copper (4.71 mg, 0.025 mmol), and cesium carbonate (241 mg, 0.741 mmol) in DMF (6 mL). The resulting tan suspension was purged with nitrogen for 3 minutes. The vial was sealed and heated at 150° C. for 1 day. The mixture was partitioned between water (30 ml) and ethyl acetate (30 ml). The organic and aqueous layers were separated and the aqueous layer was back-extracted with ethyl acetate. The organic layers were combined, washed with brine, dried over MgSO₄, and concentrated to give the title compound, which was used without further purification.

Step B: (4-(7-Fluoropyrazolo[4,3-b]indol-4(1H)-yl)-1-methyl-1H-pyrazol-3-yl)methanol A mixture of 4-(7-fluoro-1-(tetrahydro-2H-pyran-2-yl)pyrazolo[4,3-b]indol-4(1H)-yl)-1-methyl-1H-pyrazole-3-carboxylic acid (95 mg, 0.247 mmol) and THF (8 mL) was cooled to 0° C. A 1M solution of lithium aluminum hydride (0.321 mL, 0.321 mmol) in ether was added dropwise. The mixture was stirred at room temperature overnight. More lithium aluminum hydride (0.321 mL, 0.321 mmol) was added, and the mixture was again stirred at room temperature overnight. The reaction was quenched with ethyl acetate, washed with water and brine, dried over MgSO$_4$, and concentrated. The residue was dissolved in methanol (3 mL). Concentrated HCl (4 drops) was added, and the mixture was stirred at room temperature for 3 hours. The crude product was purified by preparative HPLC, eluting with 25% ACN (containing 0.035% TFA) in water (containing 0.05% TFA) to give the title compound (5.4 mg, 7.7%). $^1$H NMR (400 MHz, CD$_3$OD) δ ppm 3.96 (s, 3 H), 4.43 (s, 2 H), 7.04-7.13 (m, 1 H), 7.16-7.25 (m, 1 H), 7.51 (s, 1 H), 7.53-7.60 (m, 1 H), 7.89 (s, 1 H). MS [M+H]$^+$ calc'd for C$_{14}$H$_{12}$FN$_5$O, 286.11; found 286.1.

TABLE 1 lists MetAP2 inhibition data for many of the compounds described in the examples, where larger pIC$_{50}$ values represent higher potency. The compounds were tested in accordance with the enzyme assay described on page 34 of the specification in which the MetAP2 enzyme is complexed with cobalt or manganese ions.

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

TABLE 1

MetAP2 Inhibition (pIC$_{50}$) for Example Compounds

| Example No. | MetAP2 Co pIC$_{50}$ | MetAP2 Mn pIC$_{50}$ |
| --- | --- | --- |
| 1 | 7.4 | 7.5 |
| 2 | 7.0 | 7.3 |
| 3 | 7.6 | 7.9 |
| 4 | 7.6 | 8.0 |
| 5 | 8.1 | 7.9 |
| 6 | 8.2 | 8.2 |
| 7 | 7.8 | 7.9 |
| 8 | 7.6 | 8.3 |
| 9 | 8.0 | 8.2 |
| 10 | 7.9 | 8.1 |
| 11 | 7.0 | 8.2 |
| 12 | 7.9 | 8.3 |
| 13 | 7.9 | 8.4 |
| 14 | 8.1 | 8.1 |
| 15 | 8.0 | 8.0 |
| 16 | 8.1 | 8.2 |
| 17 | 8.1 | 8.2 |
| 18 | 7.0 | 7.2 |
| 19 | 7.9 | 7.9 |
| 20 | 7.9 | 8.2 |
| 21 | 7.8 | 8.1 |
| 22 | 7.5 | 8.0 |
| 23 | 8.0 | 7.8 |
| 24 | 8.2 | 8.4 |
| 25 | 7.6 | 7.9 |
| 26 | 8.0 | 8.1 |
| 27 | 8.2 | 8.4 |
| 28 | 8.2 | 8.3 |
| 29 | 8.2 | 8.1 |
| 30 | 8.4 | 8.2 |
| 31 | 8.1 | 8.0 |
| 32 | 8.1 | 8.0 |
| 33 | 8.1 | 8.0 |
| 34 | 7.2 | 7.1 |
| 35 | 7.4 | 7.1 |
| 36 | 7.4 | 7.2 |
| 37 | 8.2 | 8.2 |
| 38 | 8.2 | 8.1 |
| 39 | 8.2 | 8.1 |
| 40 | 7.8 | 7.8 |
| 41 | 7.9 | 7.9 |
| 42 | 8.0 | 7.8 |
| 43 | 7.9 | 7.9 |
| 44 | 8.1 | 8.0 |
| 45 | 8.2 | 7.9 |
| 46 | 7.7 | 7.7 |
| 47 | 8.1 | 7.9 |
| 48 | 7.8 | 7.9 |
| 49 | 7.2 | 7.5 |
| 50 | 8.1 | 8.2 |
| 51 | 7.9 | 8.0 |
| 52 | 7.5 | 7.3 |
| 53 | 7.3 | 7.1 |
| 54 | 7.5 | 7.4 |
| 55 | 7.6 | 7.8 |
| 56 | 7.9 | 8.1 |
| 57 | 7.6 | 7.9 |
| 58 | 7.8 | 7.9 |
| 59 | 7.9 | 8.0 |
| 60 | 8.5 | 8.0 |
| 61 | 7.8 | 7.9 |
| 62 | 7.6 | 7.5 |
| 63 | 7.8 | 7.8 |
| 64 | 7.8 | 7.9 |
| 65 | 7.9 | 8.0 |
| 66 | 8.0 | 8.5 |
| 67 | 8.1 | 8.0 |
| 68 | 8.0 | 8.5 |
| 69 | 7.7 | 8.3 |
| 70 | 7.7 | 8.0 |
| 71 | 7.9 | 8.0 |
| 72 | 8.1 | 8.5 |
| 73 | 8.2 | 8.5 |
| 74 | 8.0 | 8.1 |
| 75 | 8.1 | 8.3 |
| 76 | 8.0 | 8.2 |
| 77 | 8.1 | 8.0 |
| 78 | 7.8 | 8.0 |
| 79 | 7.8 | 7.6 |
| 80 | 7.7 | 7.5 |
| 81 | 8.3 | 8.2 |
| 82 | 8.1 | 8.0 |
| 83 | 8.2 | 8.1 |
| 84 | 7.7 | 8.0 |
| 85 | 7.8 | 7.9 |
| 86 | 8.1 | 7.9 |
| 87 | 8.1 | 8.0 |
| 88 | 7.6 | 8.0 |
| 89 | 7.7 | 8.0 |
| 90 | 7.8 | 8.3 |
| 91 | 8.2 | 7.9 |
| 92 | 8.0 | 8.1 |
| 93 | 8.1 | 8.2 |
| 94 | 8.0 | 8.1 |
| 95 | 7.5 | 7.7 |
| 96 | 7.7 | 7.9 |
| 97 | 8.0 | 8.2 |
| 98 | 6.3 | 6.8 |
| 99 | 6.1 | 6.5 |
| 100 | 7.9 | 7.9 |
| 101 | 8.0 | 8.0 |
| 102 | 7.5 | 7.4 |
| 103 | 8.2 | 8.0 |
| 104 | 8.0 | 7.9 |
| 105 | 7.3 | 7.2 |

TABLE 1-continued

MetAP2 Inhibition (pIC$_{50}$) for Example Compounds

| Example No. | MetAP2 Co pIC$_{50}$ | MetAP2 Mn pIC$_{50}$ |
|---|---|---|
| 106 | 7.0 | 7.0 |
| 107 | 7.7 | 7.9 |
| 108 | 7.7 | 7.6 |
| 109 | 7.6 | 7.6 |
| 110 | 8.0 | 7.7 |
| 111 | 8.1 | 7.9 |
| 112 | 7.9 | 7.7 |
| 113 | 7.9 | 8.0 |
| 114 | 7.6 | 7.9 |
| 115 | 7.9 | 8.0 |
| 116 | 7.9 | 8.4 |
| 117 | 7.7 | 8.1 |
| 118 | 7.6 | 8.0 |
| 119 | 7.7 | 8.0 |
| 120 | 7.8 | 7.8 |
| 121 | 7.7 | 7.8 |
| 122 | 8.1 | 8.1 |
| 123 | 8.1 | 8.2 |
| 124 | 8.0 | 7.9 |
| 125 | 7.9 | 8.0 |
| 126 | 8.0 | 8.0 |
| 127 | 8.1 | 7.8 |
| 128 | 7.1 | 7.2 |
| 129 | 7.6 | 7.3 |
| 130 | 8.0 | 7.9 |
| 131 | 7.9 | 8.1 |
| 132 | 7.3 | 7.3 |
| 133 | 8.0 | 8.2 |
| 134 | 7.8 | 8.2 |
| 135 | 8.3 | 8.3 |
| 136 | 8.3 | 8.3 |
| 137 | 8.0 | 8.2 |
| 138 | 8.0 | 8.3 |

What is claimed is:

1. A compound of Formula 1,

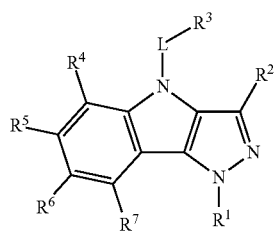

1 or a pharmaceutically acceptable salt thereof, wherein:

L is selected from a direct bond, $C_{1-4}$ alkanediyl, —C(O)—, —C(O)NH—, and —C(O)NHCH$_2$—;

$R^1$ is hydrogen;

$R^2$ is selected from hydrogen, —OH, chloro, fluoro, —CN, methyl, and hydroxymethyl;

$R^3$ is selected from $C_{6-14}$ aryl, $C_{1-9}$ heteroaryl, $C_{2-6}$ heterocyclyl, and $C_{3-8}$ cycloalkyl, each optionally substituted with from one to five substituents independently selected from halo, oxo, —CN, $R^8$, and $R^9$;

each $R^4$, $R^5$, $R^6$, and $R^7$ is independently selected from hydrogen, —OH, —NH$_2$, halo, $C_{1-4}$ alkyl, and $C_{1-4}$ haloalkyl;

each $R^8$ is independently selected from —OR$^{10}$, —N(R$^{10}$)R$^{11}$, —NR$^{10}$C(O)R$^{11}$, —NHC(O)NR$^{10}$R$^{11}$, —NR$^{10}$C(O)NHR$^{11}$, —C(O)R$^{10}$, —C(O)OR$^{10}$, —C(O)N(R$^{10}$)R$^{11}$, —C(O)N(R$^{10}$)OR$^{11}$, —C(O)N(R$^{10}$)S(O)$_2$R$^9$, —N(R$^{10}$)S(O)$_2$R$^9$, —SR$^{10}$, —S(O)R$^9$, —S(O)$_2$R$^9$, and —S(O)$_2$N(R$^{10}$)R$^{11}$;

each $R^9$ is independently selected from
(a) $C_{1-6}$ alkyl, $C_{2-6}$ alkenyl, and $C_{2-6}$ alkynyl, each optionally substituted with from one to five substituents independently selected from halo, oxo, —CN, and $R^{12}$; and
(b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, $R^{12}$, and $C_{1-6}$ alkyl optionally substituted with from one to five substituents independently selected from halo, oxo, —CN, and $R^{12}$;

each $R^{10}$ and $R^{11}$ is independently selected from
(a) hydrogen;
(b) $C_{1-6}$ alkyl, $C_{2-6}$ alkenyl, and $C_{2-6}$ alkynyl, each optionally substituted with from one to five substituents independently selected from halo, oxo, —CN, and $R^{12}$; and
(c) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, $R^{12}$, and $C_{1-6}$ alkyl optionally substituted with from one to five substituents independently selected from halo, oxo, —CN, and $R^{12}$;

each $R^{12}$ is independently selected from —OR$^{13}$, —N(R$^{13}$)R$^{14}$, —N(R$^{13}$)C(O)R$^{14}$, —NHC(O)NR$^{13}$R$^{14}$, —NR$^{13}$C(O)NHR$^{14}$, —C(O)R$^{13}$, —C(O)OR$^{13}$, —C(O)N(R$^{13}$)R$^{14}$, —C(O)N(R$^{13}$)OR$^{14}$, —C(O)N(R$^{13}$)S(O)$_2$R$^{15}$, —NR$^{13}$S(O)$_2$R$^{15}$, —SR$^{13}$, —S(O)R$^{15}$, —S(O)$_2$R$^{15}$, and —S(O)$_2$N(R$^{13}$)R$^{14}$;

each $R^{13}$ and $R^{14}$ is independently selected from
(a) hydrogen; and
(b) $C_{1-6}$ alkyl, $C_{3-8}$ cycloalkyl-(CH$_2$)$_m$—, and $C_{2-6}$ heterocyclyl-(CH$_2$)$_m$—, each optionally substituted with from one to five substituents independently selected from halo, oxo, —CN, —OH, and —NH$_2$;

each $R^{15}$ is independently selected from $C_{1-6}$ alkyl, $C_{3-8}$ cycloalkyl-(CH$_2$)$_m$—, and $C_{2-6}$ heterocyclyl-(CH$_2$)$_m$—, each optionally substituted with from one to five substituents independently selected from halo, oxo, —CN, —OH, and —NH$_2$; and each m is independently selected from 0, 1, 2, 3, and 4;

wherein each heteroaryl and heterocyclyl moiety has from one to four heteroatoms independently selected from N, O, and S.

2. A compound or pharmaceutically acceptable salt according to claim 1, wherein L is a direct bond.

3. A compound or pharmaceutically acceptable salt according to claim 1, wherein $R^3$ is selected from $C_{6-14}$ aryl and $C_{1-9}$ heteroaryl, each optionally substituted with from one to five substituents independently selected from halo, oxo, —CN, $R^8$, and $R^9$.

4. A compound or pharmaceutically acceptable salt according to claim 1, wherein $R^3$ is selected from phenyl, naphthalenyl, fluorenyl, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, benzofuranyl, isobenzofuranyl, benzothiophenyl, benzo[c]thiophenyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl,

149

3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, oxiranyl, thiiranyl, aziridinyl, oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, 1,2-dihydropyrazolo[1,5-d][1,2,4]triazinyl, and 4,5,6,7-tetrahydropyrazolo[1,5-a]pyrazinyl, each optionally substituted with from one to five substituents independently selected from halo, oxo, —CN, $R^8$, and $R^9$.

5. A compound or pharmaceutically acceptable salt according to claim 1, wherein $R^3$ is selected from phenyl, pyridinyl, pyrimidinyl, pyridazinyl, pyrazinyl, 1,2-dihydropyridinyl, 1,6-dihydropyrimidinyl, 1,2,3,4-tetrahydropyrimidinyl, imidazolyl, pyrazolyl, tetrazolyl, thiazolyl, isoxazolyl, quinolinyl, isoquinolinyl, 1,7-naphthyridinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 1H-indolyl, indolinyl, isoindolinyl, benzimidazolyl, 1H-indazolyl, 2H-indazolyl, 3H-imidazo[4,5-b]pyridinyl, 2,3-dihydro-1H-benzo[d]imidazolyl, benzo[d]thiazolyl, 1H-pyrrolo[2,3-b]pyridinyl, 1H-pyrrolo[2,3-c]pyridinyl, imidazo[1,2-a]pyridinyl, pyrazolo[1,5-a]pyridinyl, 2,3-dihydro-1H-pyrrolo[2,3-b]pyridinyl, 3H-imidazo[4,5-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, 1,2-dihydropyrazolo[1,5-d][1,2,4]triazinyl, and 4,5,6,7-tetrahydropyrazolo[1,5-a]pyrazinyl, each optionally substituted with from one to five substituents independently selected from halo, oxo, —CN, $R^8$, and $R^9$.

6. A compound or pharmaceutically acceptable salt according to claim 1, wherein $R^3$ is selected from phenyl, pyridinyl, pyrimidinyl, 1,2-dihydropyridinyl, 1,6-dihydropyrimidinyl, pyrazolyl, 1H-indazolyl, 1H-indazolyl, 2H-indazolyl, 3H-imidazo[4,5-b]pyridinyl, [1,2,4]triazolo[1,5-a]pyridinyl, 2,3-dihydro-1H-imidazo[4,5-b]pyridinyl, and 4,5,6,7-tetrahydropyrazolo[1,5-a]pyrazinyl, each optionally substituted with from one to five substituents independently selected from halo, oxo, —CN, $R^8$, and $R^9$.

7. A compound or pharmaceutically acceptable salt according to claim 1, wherein $R^2$ is hydrogen.

8. A compound or pharmaceutically acceptable salt according to claim 1, wherein $R^4$ is hydrogen.

9. A compound or pharmaceutically acceptable salt according to claim 1, wherein $R^5$ and $R^6$ are each independently selected from hydrogen, chloro, fluoro, and methyl.

10. A compound or pharmaceutically acceptable salt according to claim 1, wherein $R^5$ is hydrogen.

11. A compound or pharmaceutically acceptable salt according to claim 1, wherein $R^6$ is fluorine.

12. A compound or pharmaceutically acceptable salt according to claim 1, wherein $R^7$ is hydrogen.

13. A compound according to claim 1, which is selected from the following compounds:
 4-Benzyl-7-fluoro-1,4-dihydropyrazolo[4,3-b]indole;
 4-Benzyl-6,7-difluoro-1,4-dihydropyrazolo[4,3-b]indole;
 7-Fluoro-4-(pyridin-3-yl)-1,4-dihydropyrazolo[4,3-b]indole;
 6,7-Difluoro-4-(pyridin-3-yl)-1,4-dihydropyrazolo[4,3-b]indole;
 7-Fluoro-4-(5-methyl-3H-imidazo[4,5-b]pyridin-6-yl)-1,4-dihydropyrazolo[4,3-b]indole;
 (3R)-1-(5-(7-Fluoropyrazolo[4,3-b]indol-4(1H)-yl)-6-methylpyridin-2-yl)pyrrolidin-3-ol;
 7-Fluoro-4-(2-methyl-6-(4-methylpiperazin-1-yl)pyridin-3-yl)-1,4-dihydropyrazolo[4,3-b]indole;
 7-Fluoro-4-(2-(4-methylpiperazin-1-yl)pyridin-4-yl)-1,4-dihydropyrazolo[4,3-b]indole;
 4-(2,4-Dimethyl-2H-indazol-5-yl)-7-fluoro-1,4-dihydropyrazolo[4,3-b]indole;
 4-(2,6-Dimethylpyridin-3-yl)-7-fluoro-1,4-dihydropyrazolo[4,3-b]indole;
 7-Fluoro-4-(6-methylpyridin-2-yl)-1,4-dihydropyrazolo[4,3-b]indole;
 (2R)-1-((5-(7-Fluoropyrazolo[4,3-b]indol-4(1H)-yl)-6-methylpyridin-2-yl)amino)propan-2-ol;
 4-(3,5-Dimethyl-3H-imidazo[4,5-b]pyridin-6-yl)-7-fluoro-1,4-dihydropyrazolo[4,3-b]indole;
 4-(1,5-Dimethyl-1H-indazol-6-yl)-7-fluoro-1,4-dihydropyrazolo[4,3-b]indole;
 4-(2,6-Dimethyl-2H-indazol-5-yl)-7-fluoro-1,4-dihydropyrazolo[4,3-b]indole;
 4-(2,5-Dimethyl-2H-indazol-6-yl)-7-fluoro-1,4-dihydropyrazolo[4,3-b]indole;
 4-(1,4-Dimethyl-1H-indazol-5-yl)-7-fluoro-1,4-dihydropyrazolo[4,3-b]indole;
 6-Amino-5-(7-fluoropyrazolo[4,3-b]indol-4(1H)-yl)nicotinic acid;
 7-Fluoro-4-(6-methyl-1H-indazol-5-yl)-1,4-dihydropyrazolo[4,3-b]indole;
 (3R)-1-(5-(7-Fluoropyrazolo[4,3-b]indol-4(1H)-yl)-4-methylpyrimidin-2-yl)pyrrolidine-3-carboxamide;
 (3S)-1-(5-(7-Fluoropyrazolo[4,3-b]indol-4(1H)-yl)-4-methylpyrimidin-2-yl)pyrrolidine-3-carboxamide;
 4-(7-Fluoropyrazolo[4,3-b]indol-4(1H)-yl)-1H-pyrazole-5-carbonitrile;
 4-(1-Ethyl-3,5-dimethyl-1H-pyrazol-4-yl)-7-fluoro-1,4-dihydropyrazolo[4,3-b]indole;
 (3R)-1-(5-(7-Fluoropyrazolo[4,3-b]indol-4(1H)-yl)-4-methylpyrimidin-2-yl)piperidin-3-ol;
 7-Fluoro-4-(4,5,6,7-tetrahydropyrazolo[1,5-a]pyrazin-3-yl)-1,4-dihydropyrazolo[4,3-b]indole;

7-Fluoro-4-(5-methyl-1H-indazol-6-yl)-1,4-dihydropyrazolo[4,3-b]indole;
(3S)-1-(5-(7-Fluoropyrazolo[4,3-b]indol-4(1H)-yl)-6-methylpyridin-2-yl)pyrrolidin-3-ol;
6-(7-Fluoropyrazolo[4,3-b]indol-4(1H)-yl)-7-methyl-1H-imidazo[4,5-b]pyridin-2(3H)-one;
1-(5-(7-Fluoropyrazolo[4,3-b]indol-4(1H)-yl)-4-methylpyrimidin-2-yl)piperidin-4-ol;
4-(3-Ethyl-5-methyl-3H-imidazo[4,5-b]pyridin-6-yl)-7-fluoro-1,4-dihydropyrazolo[4,3-b]indole;
7-Fluoro-4-(3-(2-methoxyethyl)-5-methyl-3H-imidazo[4,5-b]pyridin-6-yl)-1,4-dihydropyrazolo[4,3-b]indole;
6-(7-Fluoropyrazolo[4,3-b]indol-4(1H)-yl)-1-(2-hydroxyethyl)-5-methyl-1H-imidazo[4,5-b]pyridin-2(3H)-one;
3-((S)-2,3-Dihydroxypropyl)-6-(7-fluoropyrazolo[4,3-b]indol-4(1H)-yl)-5-methyl-1H-imidazo[4,5-b]pyridin-2(3H)-one;
7-Fluoro-4-(2-((S)-3-fluoropyrrolidin-1-yl)-4-methylpyrimidin-5-yl)-1,4-dihydropyrazolo[4,3-b]indole;
(3R)-1-(5-(7-Fluoropyrazolo[4,3-b]indol-4(1H)-yl)-4-methylpyrimidin-2-yl)-N,N-dimethylpyrrolidin-3-amine;
7-Fluoro-4-(2-((R)-3-fluoropyrrolidin-1-yl)-4-methylpyrimidin-5-yl)-1,4-dihydropyrazolo[4,3-b]indole;
(3S)-1-(5-(7-Fluoropyrazolo[4,3-b]indol-4(1H)-yl)-4-methylpyrimidin-2-yl)piperidin-3-ol;
(2S)-1-(5-(7-Fluoropyrazolo[4,3-b]indol-4(1H)-yl)-4-methylpyrimidin-2-yl)-N-methylpyrrolidine-2-carboxamide;
4-(5-(7-Fluoropyrazolo[4,3-b]indol-4(1H)-yl)-4-methylpyrimidin-2-yl)-1-methylpiperazin-2-one;
5-(7-Fluoropyrazolo[4,3-b]indol-4(1H)-yl)-6-methylpyridin-2(1H)-one;
5-(7-Fluoropyrazolo[4,3-b]indol-4(1H)-yl)-4-methylpyridin-2-amine;
5-(7-Fluoropyrazolo[4,3-b]indol-4(1H)-yl)-6-methylpyridin-2-amine;
4-(2-(3,3-Difluoroazetidin-1-yl)-4-methylpyrimidin-5-yl)-7-fluoro-1,4-dihydropyrazolo[4,3-b]indole;
4-(5-(7-Fluoropyrazolo[4,3-b]indol-4(1H)-yl)-4-methylpyrimidin-2-yl)piperazin-2-one;
5-(7-Fluoropyrazolo[4,3-b]indol-4(1H)-yl)-N,4-dimethylpyridin-2-amine;
7-Fluoro-4-(1-methyl-1H-pyrazol-5-yl)-1,4-dihydropyrazolo[4,3-b]indole;
(1-(5-(7-Fluoropyrazolo[4,3-b]indol-4(1H)-yl)-4-methylpyrimidin-2-yl)azetidin-3-yl)methanol;
5-(7-Fluoropyrazolo[4,3-b]indol-4(1H)-yl)-1-methyl-1H-pyrazole-3-carboxamide;
7-Fluoro-4-(4-methylpyrimidin-5-yl)-1,4-dihydropyrazolo[4,3-b]indole;
4-(7-Fluoropyrazolo[4,3-b]indol-4(1H)-yl)-N-(2-hydroxyethyl)benzamide;
4-(7-Fluoropyrazolo[4,3-b]indol-4(1H)-yl)-N-(2-hydroxyethyl)-3-methylbenzamide;
3-((7-Fluoropyrazolo[4,3-b]indol-4(1H)-yl)methyl)-N-(2-hydroxyethyl)benzamide;
(4-((7-Fluoropyrazolo[4,3-b]indol-4(1H)-yl)methyl)phenyl)(morpholino)methanone;
(4-((7-Fluoropyrazolo[4,3-b]indol-4(1H)-yl)methyl)phenyl)(4-methylpiperazin-1-yl)methanone;
(S)-1-(5-(7-Fluoropyrazolo[4,3-b]indol-4(1H)-yl)-4-methylpyrimidin-2-yl)pyrrolidin-3-ol;
1-(5-(7-Fluoropyrazolo[4,3-b]indol-4(1H)-yl)-4-methylpyrimidin-2-yl)piperidine-4-carbonitrile;
7-Fluoro-4-(2-(4-fluoropiperidin-1-yl)-4-methylpyrimidin-5-yl)-1,4-dihydropyrazolo[4,3-b]indole;
(3R)-1-(5-(7-Fluoropyrazolo[4,3-b]indol-4(1H)-yl)-4-methylpyrimidin-2-yl)pyrrolidin-3-ol;
(1-(5-(7-Fluoropyrazolo[4,3-b]indol-4(1H)-yl)-4-methylpyrimidin-2-yl)piperidin-4-yl)methanol;
7-Fluoro-4-(4-methyl-2-(4-methylpiperazin-1-yl)pyrimidin-5-yl)-1,4-dihydropyrazolo[4,3-b]indole;
7-Fluoro-4-(2-methylpyridin-3-yl)-1,4-dihydropyrazolo[4,3-b]indole;
7-Fluoro-4-(1,3,5-trimethyl-1H-pyrazol-4-yl)-1,4-dihydropyrazolo[4,3-b]indole;
2-((5-(7-Fluoropyrazolo[4,3-b]indol-4(1H)-yl)-4-methylpyrimidin-2-yl)(methyl)amino)ethanol;
7-Fluoro-4-(2-methyl-6-(piperazin-1-yl)pyridin-3-yl)-1,4-dihydropyrazolo[4,3-b]indole;
7-Fluoro-4-(5-(methoxymethyl)-1H-pyrazol-4-yl)-1,4-dihydropyrazolo[4,3-b]indole;
4-(5-(7-Fluoropyrazolo[4,3-b]indol-4(1H)-yl)-6-methylpyridin-2-yl)morpholine;
6-(7-Fluoropyrazolo[4,3-b]indol-4(1H)-yl)-1-(2-hydroxyethyl)-5-methyl-1H-imidazo[4,5-b]pyridin-2(3H)-one;
5-(7-Fluoropyrazolo[4,3-b]indol-4(1H)-yl)-3,4-dimethylpyridin-2-amine;
7-Fluoro-4-(6-methoxy-2-methylpyridin-3-yl)-1,4-dihydropyrazolo[4,3-b]indole;
7-Fluoro-4-(5-methyl-[1,2,4]triazolo[1,5-a]pyridin-6-yl)-1,4-dihydropyrazolo[4,3-b]indole;
7-Fluoro-4-(4-methyl-1H-indazol-5-yl)-1,4-dihydropyrazolo[4,3-b]indole;
(2S)-1-(5-(7-Fluoropyrazolo[4,3-b]indol-4(1H)-yl)-4-methylpyrimidin-2-yl)pyrrolidine-2-carboxamide;
(2R)-1-(5-(7-Fluoropyrazolo[4,3-b]indol-4(1H)-yl)-4-methylpyrimidin-2-yl)pyrrolidine-2-carboxamide;
2-((5-(7-Fluoropyrazolo[4,3-b]indol-4(1H)-yl)-4-methylpyrimidin-2-yl)amino)ethanol;
(2R)-2-((5-(7-Fluoropyrazolo[4,3-b]indol-4(1H)-yl)-4-methylpyrimidin-2-yl)amino)propan-1-ol;
(3R,4R)-1-(5-(7-Fluoropyrazolo[4,3-b]indol-4(1H)-yl)-4-methylpyrimidin-2-yl)pyrrolidine-3,4-diol;
((2R)-4-(5-(7-Fluoropyrazolo[4,3-b]indol-4(1H)-yl)-4-methylpyrimidin-2-yl)morpholin-2-yl)methanol;
1-(5-(7-Fluoropyrazolo[4,3-b]indol-4(1H)-yl)-4-methylpyrimidin-2-yl)piperidin-4-ol;
(2S)-3-(6-(7-Fluoropyrazolo[4,3-b]indol-4(1H)-yl)-5-methyl-3H-imidazo[4,5-b]pyridin-3-yl)propane-1,2-diol;
3-(6-(7-Fluoropyrazolo[4,3-b]indol-4(1H)-yl)-5-methyl-3H-imidazo[4,5-b]pyridin-3-yl)propan-1-ol;
6-(7-Fluoropyrazolo[4,3-b]indol-4(1H)-yl)-3-(3-hydroxypropyl)-5-methyl-1H-imidazo[4,5-b]pyridin-2(3H)-one;
2-(6-(7-Fluoropyrazolo[4,3-b]indol-4(1H)-yl)-5-methyl-3H-imidazo[4,5-b]pyridin-3-yl)ethanol;
((2S)-4-(5-(7-Fluoropyrazolo[4,3-b]indol-4(1H)-yl)-4-methylpyrimidin-2-yl)morpholin-2-yl)methanol;
(R)-5-(7-Fluoropyrazolo[4,3-b]indol-4(1H)-yl)-2-(3-hydroxypyrrolidin-1-yl)pyrimidin-4(3H)-one;
5-(7-Fluoropyrazolo[4,3-b]indol-4(1H)-yl)-4-methylpyrimidin-2-amine;
(2R)-3-((5-(7-Fluoropyrazolo[4,3-b]indol-4(1H)-yl)-4-methylpyrimidin-2-yl)amino)propane-1,2-diol;
6-(7-Fluoropyrazolo[4,3-b]indol-4(1H)-yl)-5-methyl-1H-imidazo[4,5-b]pyridin-2(3H)-one;
5-(7-Fluoropyrazolo[4,3-b]indol-4(1H)-yl)-N-(2-hydroxyethyl)-1-methyl-1H-pyrazole-3-carboxamide;

1-(5-(7-Fluoropyrazolo[4,3-b]indol-4(1H)-yl)-4-methylpyrimidin-2-yl)azetidine-3-carboxamide;
(2R)-3-(6-(7-Fluoropyrazolo[4,3-b]indol-4(1H)-yl)-5-methyl-3H-imidazo[4,5-b]pyridin-3-yl)propane-1,2-diol;
(2S)-2-((5-(7-Fluoropyrazolo[4,3-b]indol-4(1H)-yl)-4-methylpyrimidin-2-yl)amino)propan-1-ol;
(2S)-1-((5-(7-Fluoropyrazolo[4,3-b]indol-4(1H)-yl)-4-methylpyrimidin-2-yl)amino)propan-2-ol;
(2R)-1-((5-(7-Fluoropyrazolo[4,3-b]indol-4(1H)-yl)-4-methylpyrimidin-2-yl)amino)propan-2-ol;
(5-(7-Fluoropyrazolo[4,3-b]indol-4(1H)-yl)-4-methylpyridin-2-yl)(3-hydroxyazetidin-1-yl)methanone;
5-(7-Fluoropyrazolo[4,3-b]indol-4(1H)-yl)-N-(2-hydroxyethyl)-4-methylpicolinamide;
5-(7-Fluoropyrazolo[4,3-b]indol-4(1H)-yl)-N-(2-hydroxyethyl)-6-methylpicolinamide;
(5-(7-Fluoropyrazolo[4,3-b]indol-4(1H)-yl)-6-methylpyridin-2-yl)(3-hydroxyazetidin-1-yl)methanone;
N-Benzyl-7-fluoropyrazolo[4,3-b]indole-4(1H)-carboxamide;
Cyclopropyl(7-fluoropyrazolo[4,3-b]indol-4(1H)-yl)methanone;
5-(7-Fluoropyrazolo[4,3-b]indol-4(1H)-yl)-N-(1-(hydroxymethyl)cyclopropyl)-6-methylpicolinamide;
N-Cyclopropyl-5-(7-fluoropyrazolo[4,3-b]indol-4(1H)-yl)-6-methylpicolinamide;
5-(7-Fluoropyrazolo[4,3-b]indol-4(1H)-yl)-N-(2-methoxyethyl)-6-methylpicolinamide;
(3S)-1-(5-(7-Fluoropyrazolo[4,3-b]indol-4(1H)-yl)-4-methylpyrimidin-2-yl)-N-(2-hydroxyethyl)pyrrolidine-3-carboxamide;
5-(7-Fluoropyrazolo[4,3-b]indol-4(1H)-yl)-N-(1-(hydroxymethyl)cyclopropyl)-4-methylpicolinamide;
5-(7-Fluoropyrazolo[4,3-b]indol-4(1H)-yl)-N-(2-methoxyethyl)-4-methylpicolinamide;
(5-(7-Fluoropyrazolo[4,3-b]indol-4(1H)-yl)-4-methylpyridin-2-yl)(morpholino)methanone;
5-(7-Fluoropyrazolo[4,3-b]indol-4(1H)-yl)-4-methylpicolinamide;
5-(7-Fluoropyrazolo[4,3-b]indol-4(1H)-yl)-N,N,4-trimethylpicolinamide;
(5-(7-Fluoropyrazolo[4,3-b]indol-4(1H)-yl)-4-methylpyridin-2-yl)((R)-3-hydroxypyrrolidin-1-yl)methanone;
7-Fluoro-4-(7-methyl-3H-imidazo[4,5-b]pyridin-6-yl)-1,4-dihydropyrazolo[4,3-b]indole;
((3 S)-1-(5-(7-Fluoropyrazolo[4,3-b]indol-4(1H)-yl)-4-methylpyrimidin-2-yl)pyrrolidin-3-yl)(3-hydroxyazetidin-1-yl)methanone;
4-(5-Ethyl-4,5,6,7-tetrahydropyrazolo[1,5-a]pyrazin-3-yl)-7-fluoro-1,4-dihydropyrazolo[4,3-b]indole;
5-(7-Fluoropyrazolo[4,3-b]indol-4(1H)-yl)-N,4-dimethylpicolinamide;
(3-Aminoazetidin-1-yl)(5-(7-fluoropyrazolo[4,3-b]indol-4(1H)-yl)-4-methylpyridin-2-yl)methanone;
5-(7-Fluoropyrazolo[4,3-b]indol-4(1H)-yl)-N-(3-hydroxypropyl)-4-methylpicolinamide;
7-Fluoro-4-(5-methyl-3-(2-(methylsulfonyl)ethyl)-3H-imidazo[4,5-b]pyridin-6-yl)-1,4-dihydropyrazolo[4,3-b]indole;
(3-Aminoazetidin-1-yl)(5-(7-fluoropyrazolo[4,3-b]indol-4(1H)-yl)-6-methylpyridin-2-yl)methanone;
5-(7-Fluoropyrazolo[4,3-b]indol-4(1H)-yl)-N-(3-hydroxypropyl)-6-methylpicolinamide;
5-(7-Fluoropyrazolo[4,3-b]indol-4(1H)-yl)-N,6-dimethylpicolinamide;
5-(7-Fluoropyrazolo[4,3-b]indol-4(1H)-yl)-N-(2-hydroxyethyl)-N,6-dimethylpicolinamide;
N-(Cyanomethyl)-5-(7-fluoropyrazolo[4,3-b]indol-4(1H)-yl)-N,6-dimethylpicolinamide;
N-(2-Cyanoethyl)-5-(7-fluoropyrazolo[4,3-b]indol-4(1H)-yl)-6-methylpicolinamide;
5-(7-Fluoropyrazolo[4,3-b]indol-4(1H)-yl)-N—((R)-2-hydroxypropyl)-6-methylpicolinamide;
N-(2-Amino-2-oxoethyl)-5-(7-fluoropyrazolo[4,3-b]indol-4(1H)-yl)-6-methylpicolinamide;
1-(5-(7-Fluoropyrazolo[4,3-b]indol-4(1H)-yl)-6-methylpicolinoyl)azetidine-3-carbonitrile;
5-(7-Fluoropyrazolo[4,3-b]indol-4(1H)-yl)-N-((2S)-2-hydroxypropyl)-6-methylpicolinamide;
1-(5-(7-Fluoropyrazolo[4,3-b]indol-4(1H)-yl)-4-methylpyrimidin-2-yl)azetidin-3-ol;
6-Chloro-4-(5-methyl-3H-imidazo[4,5-b]pyridin-6-yl)-1,4-dihydropyrazolo[4,3-b]indole;
6-Chloro-7-fluoro-4-(5-methyl-3H-imidazo[4,5-b]pyridin-6-yl)-1,4-dihydropyrazolo[4,3-b]indole;
6,7-Difluoro-4-(5-methyl-3H-imidazo[4,5-b]pyridin-6-yl)-1,4-dihydropyrazolo[4,3-b]indole;
7-Fluoro-6-methyl-4-(5-methyl-1H-imidazo[4,5-b]pyridin-6-yl)-1,4-dihydropyrazolo[4,3-b]indole;
7-Fluoro-4-(1-phenylethyl)-1,4-dihydropyrazolo[4,3-b]indole;
7-Fluoro-4-(2-methyl-6-(2-(methylsulfonyl)ethyl)pyridin-3-yl)-1,4-dihydropyrazolo[4,3-b]indole;
(1-(Difluoromethyl)-4-(7-fluoropyrazolo[4,3-b]indol-4(1H)-yl)-1H-pyrazol-3-yl)methanol;
(1R,2R,5S)-3-(5-(7-Fluoropyrazolo[4,3-b]indol-4(1H)-yl)-4-methylpyrimidin-2-yl)-3-azabicyclo[3.1.0]hexane-2-carboxamide;
(1R,2S,5S)-3-(5-(7-Fluoropyrazolo[4,3-b]indol-4(1H)-yl)-4-methylpyrimidin-2-yl)-3-azabicyclo[3.1.0]hexane-2-carboxamide;
7-Fluoro-4-(4-methyl-2-((S)-3-(methylsulfonyl)pyrrolidin-1-yl)pyrimidin-5-yl)-1,4-dihydropyrazolo[4,3-b]indole;
(4-(7-Fluoropyrazolo[4,3-b]indol-4(1H)-yl)-1-methyl-1H-pyrazol-3-yl)methanol;
a stereoisomer of any one of the aforementioned compounds; and
a pharmaceutically acceptable salt of any of the aforementioned compounds or stereoisomers.

14. A pharmaceutical composition comprising:
a compound or pharmaceutically acceptable salt as defined in claim 1; and
a pharmaceutically acceptable excipient.

15. A method of treating a disease, disorder or condition in a subject, the method comprising administering to the subject an effective amount of a compound or a pharmaceutically acceptable salt as defined in claim 1, wherein the disease or condition is selected from obesity, overweight, cardiovascular disease, hypertension, diabetes, hyperglycemia, insulin resistance, metabolic syndrome X, impaired glucose tolerance, non-alcoholic liver steatosis, dyslipidemia, atherosclerosis, stroke, sleep apnea, osteoarthritis, infertility, and polycystic ovary syndrome.

16. A combination comprising an effective amount of a compound or pharmaceutically acceptable salt as defined in claim 1, and at least one additional pharmacologically active agent.

17. A combination according to claim 16, wherein the additional pharmacologically active agent is selected from insulin, buformin, metformin, phenformin, pioglitazone, rosiglitazone, acetohexamide, chlorpropamide, tolazamide, tolbutamide, gliclazide, glimepiride, glipizide, glyburide, nateglinide, repaglinide, acarbose, miglitol, exenatide, liraglutide, taspoglutide, alogliptin, linagliptin, saxagliptin, sitagliptin, vildagliptin, pramlinitide, orlistat, atorvastatin, fluvastatin, lovastatin, mevastatin, pitavastatin, pravastatin, rosuvastatin, simvastatin, niacin, bezafibrate, ciprofibrate, clofibrate, fenofibrate, gemfibrozil, cholestyramine, colesevelam, colestipol, and ezetimibe.

* * * * *